US012144875B2

(12) United States Patent
Chen et al.

(10) Patent No.: US 12,144,875 B2
(45) Date of Patent: *Nov. 19, 2024

(54) COMPOSITIONS AND METHODS FOR IMAGING

(71) Applicant: Tayu Huaxia Biotech Medical Group Co., Ltd., Beijing (CN)

(72) Inventors: Lieping Chen, Beijing (CN); Liqun Luo, Beijing (CN); Zhenguo Wen, Beijing (CN); Qianyong Liu, Beijing (CN)

(73) Assignee: Tayu Huaxia Biotech Medical Group Co., Ltd., Beijing (CN)

( * ) Notice: Subject to any disclaimer, the term of this patent is extended or adjusted under 35 U.S.C. 154(b) by 888 days.

This patent is subject to a terminal disclaimer.

(21) Appl. No.: 15/733,835

(22) PCT Filed: May 31, 2019

(86) PCT No.: PCT/CN2019/089571
§ 371 (c)(1),
(2) Date: Nov. 30, 2020

(87) PCT Pub. No.: WO2019/228509
PCT Pub. Date: Dec. 5, 2019

(65) Prior Publication Data
US 2021/0213145 A1    Jul. 15, 2021

(30) Foreign Application Priority Data
Jun. 1, 2018  (WO) ................ PCT/CN2018/089672

(51) Int. Cl.
*A61K 9/00*       (2006.01)
*A61K 51/04*      (2006.01)
(Continued)

(52) U.S. Cl.
CPC ...... *A61K 51/1027* (2013.01); *A61K 51/0497* (2013.01); *C07K 16/2827* (2013.01);
(Continued)

(58) Field of Classification Search
CPC .. A61K 51/00; A61K 51/027; A61K 51/0497; A61K 2039/505; A61K 51/1027;
(Continued)

(56) References Cited

U.S. PATENT DOCUMENTS 4,816,567 A    3/1989  Cabilly
5,500,362 A    3/1996  Robinson
(Continued)

FOREIGN PATENT DOCUMENTS

CN    1315967 A    10/2001
CN    1905900 A    1/2007
(Continued)

OTHER PUBLICATIONS

Steiner and Neri, Clin. Cancer Res., vol. 17, No. 20, pp. 6406-6416 (Year: 2011).*

(Continued)

*Primary Examiner* — Paul W Dickinson
(74) *Attorney, Agent, or Firm* — MORRISON & FOERSTER LLP

(57) ABSTRACT

Provided are methods, imaging agents and kits for determination of the distribution and expression levels of an immune checkpoint ligand (such as PD-L1 or a PD-L1 like ligand) in an individual having a disease or condition. Anti-PD-L1 antibody agents are also provided.

21 Claims, 21 Drawing Sheets

Specification includes a Sequence Listing.

(51) Int. Cl.
  *A61K 51/10* (2006.01)
  *C07K 16/28* (2006.01)
  *A61K 39/00* (2006.01)
(52) U.S. Cl.
  CPC .... *A61K 2039/505* (2013.01); *C07K 2317/33* (2013.01); *C07K 2317/622* (2013.01); *C07K 2317/92* (2013.01); *C07K 2317/94* (2013.01)
(58) Field of Classification Search
  CPC ............ C07K 16/2827; C07K 2317/33; C07K 2317/622; C07K 2317/92; C07K 2317/94; C07K 2317/24
  USPC ........ 424/1.11, 1.49, 1.65, 1.69, 1, 85, 1.89, 424/9.1, 9.2, 9.3, 9.4, 9.5, 9.6; 530/300; 514/1, 1.1
  See application file for complete search history.

(56) References Cited

U.S. PATENT DOCUMENTS

| | | |
|---|---|---|
| 5,591,828 A | 1/1997 | Bosslet |
| 5,624,821 A | 4/1997 | Winter |
| 5,648,260 A | 7/1997 | Winter |
| 5,750,373 A | 5/1998 | Garrard |
| 5,753,206 A | 5/1998 | Mcbride et al. |
| 5,770,429 A | 6/1998 | Lonberg et al. |
| 5,821,333 A | 10/1998 | Carter |
| 5,821,337 A | 10/1998 | Carter |
| 6,075,181 A | 6/2000 | Kucherlapati |
| 6,150,584 A | 11/2000 | Kucherlapati |
| 6,194,551 B1 | 2/2001 | Idusogie |
| 6,602,684 B1 | 8/2003 | Umana |
| 6,737,056 B1 | 5/2004 | Presta |
| 6,953,567 B2 | 10/2005 | Griffiths |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,849 B2 | 5/2008 | Honda |
| 7,521,541 B2 | 4/2009 | Eigenbrot |
| 7,527,791 B2 | 5/2009 | Adams |
| 7,642,228 B2 | 1/2010 | Carter |
| 8,313,913 B2 | 11/2012 | Nakamura |
| 8,679,491 B2 | 3/2014 | Hanai |
| 8,754,287 B2 | 6/2014 | Macdonald |
| 8,945,862 B2 | 2/2015 | Wu et al. |
| 9,884,131 B2 | 2/2018 | Kjaer et al. |
| 10,465,007 B2 | 11/2019 | Chen et al. |
| 11,161,904 B2 | 11/2021 | Li et al. |
| 11,987,629 B2 | 5/2024 | Chen et al. |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0216958 A1 | 9/2005 | Yamane et al. |
| 2005/0266000 A1 | 12/2005 | Bond |
| 2006/0270045 A1 | 11/2006 | Cregg |
| 2007/0061900 A1 | 3/2007 | Murphy |
| 2007/0117126 A1 | 5/2007 | Sidhu |
| 2007/0134759 A1 | 6/2007 | Nishiya |
| 2007/0160598 A1 | 7/2007 | Dennis |
| 2007/0237764 A1 | 10/2007 | Birtalan |
| 2007/0292936 A1 | 12/2007 | Barthelemy |
| 2008/0241884 A1 | 10/2008 | Shitara |
| 2009/0002360 A1 | 1/2009 | Chen |
| 2009/0307787 A1 | 12/2009 | Grosveld |
| 2010/0122358 A1 | 5/2010 | Brueggemann |
| 2010/0329977 A1 | 12/2010 | Hengerer et al. |
| 2011/0287009 A1 | 11/2011 | Scheer |
| 2015/0289489 A1 | 10/2015 | Macdonald |
| 2015/0346208 A1 | 12/2015 | Couto |
| 2016/0009805 A1 | 1/2016 | Kowanetz |
| 2016/0052990 A1 | 2/2016 | Ring et al. |
| 2016/0331852 A1 | 11/2016 | Zeglis |
| 2017/0157265 A1 | 6/2017 | Junutula et al. |
| 2017/0218066 A1 | 8/2017 | Zhou |
| 2018/0071413 A1 | 3/2018 | Olive |
| 2018/0305464 A1 | 10/2018 | Li et al. |
| 2019/0077867 A1 | 3/2019 | Zhu et al. |
| 2019/0144543 A1 | 5/2019 | Chen et al. |
| 2019/0330348 A1 | 10/2019 | Qian |
| 2020/0115454 A1 | 4/2020 | Chen et al. |
| 2020/0407447 A1 | 12/2020 | Nicosia |
| 2021/0214444 A1 | 7/2021 | Chen et al. |
| 2021/0261665 A1 | 8/2021 | Chen et al. |
| 2021/0309745 A1 | 10/2021 | Chen et al. |
| 2022/0088232 A1 | 3/2022 | Chen et al. |

FOREIGN PATENT DOCUMENTS

| | | |
|---|---|---|
| CN | 101927007 A | 12/2010 |
| CN | 106146663 A | 11/2016 |
| CN | 106459200 A | 2/2017 |
| CN | 107118767 | 9/2017 |
| CN | 107205979 | 9/2017 |
| CN | 107311941 A | 11/2017 |
| CN | 107847574 A | 3/2018 |
| CN | 107921131 A | 4/2018 |
| CN | 107922503 A | 4/2018 |
| EP | 0404097 A2 | 12/1990 |
| EP | 3309177 A1 | 4/2018 |
| WO | 198704462 A1 | 7/1987 |
| WO | 199311161 A1 | 6/1993 |
| WO | 199429351 A2 | 12/1994 |
| WO | 199429351 A3 | 2/1995 |
| WO | 199704801 A1 | 2/1997 |
| WO | 199730087 A1 | 8/1997 |
| WO | 199858964 A1 | 12/1998 |
| WO | 199922764 A1 | 5/1999 |
| WO | 199951642 A1 | 10/1999 |
| WO | 200061739 A1 | 10/2000 |
| WO | 200129246 A1 | 4/2001 |
| WO | 2002031140 A1 | 4/2002 |
| WO | 2003011878 A2 | 2/2003 |
| WO | 2003048731 A2 | 6/2003 |
| WO | 2003084570 A1 | 10/2003 |
| WO | 2003085107 A1 | 10/2003 |
| WO | 2003011878 A3 | 11/2003 |
| WO | 2003048731 A3 | 1/2004 |
| WO | 2004049794 A2 | 6/2004 |
| WO | 2004056312 A2 | 7/2004 |
| WO | 2004049794 A3 | 12/2004 |
| WO | 2005035586 A1 | 4/2005 |
| WO | 2005035778 A1 | 4/2005 |
| WO | 2004056312 A3 | 5/2005 |
| WO | 2005053742 A1 | 6/2005 |
| WO | 2003085119 A1 | 8/2005 |
| WO | 2005100402 A1 | 10/2005 |
| WO | 2006029879 A2 | 3/2006 |
| WO | 2006067376 A2 | 6/2006 |
| WO | 2006029879 A3 | 9/2006 |
| WO | 2006121168 A1 | 11/2006 |
| WO | 2007005874 A2 | 1/2007 |
| WO | 2007005874 A3 | 7/2007 |
| WO | 2008077546 A1 | 7/2008 |
| WO | 2011068965 A1 | 6/2011 |
| WO | 2012082618 A2 | 6/2012 |
| WO | 2012153254 A1 | 11/2012 |
| WO | 2013055958 A1 | 4/2013 |
| WO | 2013173223 A1 | 11/2013 |
| WO | 2015012904 A2 | 1/2015 |
| WO | 2015048520 A1 | 4/2015 |
| WO | 2015143382 A1 | 9/2015 |

(56) References Cited

FOREIGN PATENT DOCUMENTS

| | | |
|---|---|---|
| WO | 2016079049 A1 | 5/2016 |
| WO | 2016086021 A1 | 6/2016 |
| WO | 2016089873 A1 | 6/2016 |
| WO | 2016130819 A2 | 8/2016 |
| WO | 2016149188 A1 | 9/2016 |
| WO | 2016162368 A1 | 10/2016 |
| WO | 2017019846 A1 | 2/2017 |
| WO | 2017020291 A1 | 2/2017 |
| WO | 2017020858 A1 | 2/2017 |
| WO | 2017034916 A1 | 3/2017 |
| WO | 2017059397 A1 | 4/2017 |
| WO | 2017079112 A1 | 5/2017 |
| WO | 2017118321 A1 | 7/2017 |
| WO | 2017134305 A1 | 8/2017 |
| WO | 2017148424 A1 | 9/2017 |
| WO | 2017161976 A1 | 9/2017 |
| WO | 2017210302 A1 | 12/2017 |
| WO | 2017210335 A1 | 12/2017 |
| WO | 2017215590 A1 | 12/2017 |
| WO | 2018017673 A1 | 1/2018 |
| WO | 2018054940 A1 | 3/2018 |
| WO | 2018080812 A1 | 5/2018 |
| WO | 2018102682 A1 | 6/2018 |
| WO | 2018133837 A1 | 7/2018 |
| WO | 2019228514 A1 | 12/2019 |
| WO | 2020015722 A1 | 1/2020 |
| WO | 2020019232 A1 | 1/2020 |
| WO | 2020151572 A1 | 7/2020 |

OTHER PUBLICATIONS

Abhinandan, K.R et al. (Aug. 2008, e-pub. Jul. 9, 2008). "Analysis and Improvements to Kabat and Structurally Correct Numbering of Antibody Variable Domain," Molecular Immunology 45(14):3832-3839.
Adolf-Bryfogle, J. et al. (2015, e-pub. Nov. 11, 2014). "PyIgClassify: A Database of Antibody CDR Structural Classifications," Nucleic Acids Res. 43:D432-D438.
Al-Lazikani, B. et al. (1997). "Standard Conformations for the Canonical Structures of Immunoglobulins," J. Mol. Biol. 273:927-948.
Almagro, J. et al. (Jan. 1, 2008). "Humanization of Antibodies," Frontiers in Bioscience 13:1619-1633.
Baca, M. et al. (Apr. 18, 1997). "Antibody Humanization Using Monovalent Phage Display," J. Biol. Chem. 272(16):10678-10684.
Boerner, P. et al. (Jul. 1, 1991). "Production of Antigen-Specific Human Monoclonal Antibodies From in Vitro-Primed Human Splenocytes," J. Immunol. 147(1):86-95.
Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Burton, D.R. (1985). "Immunoglobulin G: Functional Sites," Molec. Immunol. 22(3):161-206.
Burvenich, I.G.J. et al. (Mar. 8, 2018). "Receptor Occupancy Imaging Studies in Oncology Drug Development," The AAPS Journal 20(2):1-16.
Butte, M.J. et al. (Jul. 2007). "Programmed Death-1 Ligand 1 Interacts Specifically with the B7-1 Costimulatory Molecule to Inhibit T Cell Responses," Immunity 27:111-122, 12 pages.
Capel, P.J. et al. (Feb. 1994). "Heterogeneity of Human IgG Fc Receptors," Immunomethods 4(1):25-34.
Carter, P. et al. (May 1992). "Humanization of an Anti-p185HER2 Antibody for Human Cancer Therapy," Proc. Natl. Acad. Sci. USA 89:4285-4289.
Chen, L. et al. (2015, e-pub. Sep. 1, 2015). "Anti-PD-1/PD-L1 Therapy of Human Cancer: Past, Present, and Future," The Journal of Clinical Investigation 125(9)3384-3391.
Chen, W. et al. (Jan. 2010). "A Large Human Domain Antibody Library Combining Heavy and Light Chain CDR3 Diversity," Mol. Immunol. 47(4):912-921, 23 pages.
Chothia, C. et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.
Cierna, Z. et al. (Feb. 2016, e-pub. Nov. 23, 2015). "Prognostic Value of Programmed-Death-1 Receptor (PD-1) and Its Ligand 1 (PD-L1) In Testicular Germ Cell Tumors," Annals of Oncology 27(2):300-305.
Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Cole, S.P.C. et al. (1985). "The EBV-Hybridoma Technique and Its Applicaton to Human Lung Cancer," in Monoclonal Antibodies and Cancer Therapy, Alan R. Liss, p. 77-96.
Cragg, M.S. et al. (Apr. 1, 2004). "Antibody Specificity Controls In Vivo Effector Mechanisms of Anti-CD20 Reagents," Blood 103(7):2738-2743.
Cragg, M.S. et al. (Feb. 1, 2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'acqua, W. et al. (2005). "Antibody Humanization by Framework Shuffling," Methods 36:43-60.
Daëron, M. (1997). "Fc Receptor Biology," Ann. Rev. Immunol. 15:203-234.
De Haas, M. et al. (1995). "Fcγ Receptor of Phagocytes," J. Lab. Clin. Med. 126(4):330-341.
Dong, H. et al. (Dec. 1999). "B7-H1, A Third Member of the B7 Family, Co-Stimulates T-Cell Proliferation and Interleukin-10 Secretion," Nature Med. 5(12):1365-1369.
Dong, H. et al. (2002). "Tumor-Associated B7-HI Promotes T-Cell Apoptosis: A Potential Mechanism of Immune Evasion," Nature Medicine 8(8):793-800.
Dong, H. et al. (Mar. 2004). "B7-H1 Determines Accumulation and Deletion of Intrahepatic CD8+ T Lymphocytes," Immunity 20(3):327-336.
Du, Y. et al. (2018). "Liposomal Nanohybrid Cerasomes Targeted to PD-L1 Enable Dual-modality Imaging and Improve Antitumor Treatments," Cancer Letters 414:230-238.
Duncan, A.R. et al. (Apr. 21, 1988), "The Binding Site for C1q on IgG," Nature 322:738-740.
Edgar, R.C. (2004, e-pub. Mar. 19, 2004). "MUSCLE: Multiple Sequence Alignment With High Accuracy and High Throughput," Nucleic Acids Research 32(5):1792-1797.
Edgar, R.C. (Aug. 19, 2004). "MUSCLE: A Multiple Sequence Alignment Method With Reduced Time and Space Complexity," BMC Bioinformatics 5(113):1-19.
Ehrenmann, F. et al. (Jan. 2010, e-pub. Nov. 9, 2009), "IMGT/3Dstructure-DB and IMGT/DomainGapAlign: A Database and a Tool for Immunoglobulins or Antibodies, T Cell Receptors, MHC, IgSF and MhcSF," Nucleic Acids Res. 38:D301-D307.
Endo, Y. et al. (2003). "High-Throughput, Genome-Scale Protein Production Method Based on the Wheat Germ Cell-Free Expression System," Biotechnol. Adv. 21:695-713.
Extended European Search Report, dated Feb. 8, 2022, for European Patent Application No. 18927730.4, 17 pages.
Extended European Search Report, dated Feb. 9, 2022, for European Patent Application No. 19810897.9, 14 pages.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.

(56) References Cited

OTHER PUBLICATIONS

Gandini, S. et al. (Apr. 2016, e-pub. Feb. 10, 2016). "PD-L1 Expression In Cancer Patients Receiving Anti PD-1/PD-L1 Antibodies: A Systematic Review and Meta-Analysis," Critical Reviews in Oncology/Hematology 100:88-98.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Goding, J.W. (1983). "Production of Monoclonal Antibodies," Chapter 3 in Monoclonal Antibodies: Principles and Practice, Academic Press, pp. 59-103.
Granier, C. et al. (Jul. 1, 2017). "Mechanisms of Action and Rationale for the Use of Checkpoint Inhibitors in Cancer," ESMO Open 2(2):e000213, 9 pages.
Griffiths, A.D. et al. (1993). "Human Anti-Self Antibodies with High Specificity from Phage Display Libraries," EMBO J. 12(2):725-734.
Guyer, R.L. et al. (Aug. 1976). "Immunoglobulin Binding By Mouse Intestinal Epithelial Cell Receptors," J. Immunol. 117(2):587-593.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Scl. USA 83:7059-7063.
Hettich, M. et al. (Jun. 18, 2016). "High-Resolution PET Imaging With Therapeutic Antibody-Based PD-1/PD-L1 Checkpoint Tracers," Theranostics 6(10):1629-1640.
Hirano, F. et al. (Feb. 1, 2005). "Blockade of B7-H1 and PD-1 By Monoclonal Antibodies Potentiates Cancer Therapeutic Immunity," Cancer Research 65(3):1089-1096.
Hollinger, P. et al. (Jul. 1993). "Diabodies: Small Bivalent And Bispecific Antibody Fragments," Proc. Natl. Acad. Sci. USA 90:6444-6448.
Honegger, A. et al. (2001). "Yet Another Numbering Scheme for Immunoglobulin Variable Domains: An Automatic Modeling and Analysis Tool," J Mol Biol. 309(3):657-670.
Hoogenboom, H.R et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability, Issued Dec. 1, 2020, for PCT Application No. PCT/CN2018/089672, filed Jun. 1, 2018, 6 pages.
International Preliminary Report on Patentability, issued December 1. 2020, for PCT Application No. PCT/CN2019/08606, filed May 31, 2019, 5 pages.
International Preliminary Report on Patentability, issued December 1. 2020, for PCT Application No. PCT/CN2019/089571, filed May 31, 2019, 6 pages.
International Preliminary Report on Patentability, issued Jan. 26, 2021, for PCT Application No. PCT/CN2018/097175, filed Jul. 26, 2018, 7 pages.
International Preliminary Report on Patentability, issued Jul. 27, 2021, for PCT Application No. PCT/CN2020/072572, filed Jan. 17, 2020, 9 pages.
International Search Report and Written Opinion, mailed Feb. 25, 2019, for PCT Application No. PCT/CN2018/089672, filed Jun. 1, 2018, 14 pages.
International Search Report and Written, mailed Apr. 16, 2020, for PCT Application No. PCT/CN2020/072572, filed Jan. 17, 2020, 16 pages,.
International Search Report and Written, mailed Aug. 27, 2019, for PCT Application No. PCT/CN2019/089571, filed May 31, 2019, 14 pages.
International Search Report and Written, mailed Sep. 10, 2019, for PCT Application No. PCT/CN2019/08606, filed May 31, 2019, 12 pages.
International Search Report, mailed Apr. 30, 2019, for PCT Application No. PCT/CN2018/09715, filed Jul. 26, 2018, 12 pages.
Ishida, Y. et al. (1992). "Induced Expression Of PD-1. A Novel Member of the immunoglobulin Gene Superfamily. Upon Programmed Cell Death," EMBO J. 11(11):3887-3895.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
Kabat, E.A. et al. (Oct. 10, 1977). "Unusual Distribution of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bloeng. 94(4):680-688.
Kashmiri, S.V. et al. (2005). "SDR grafting—A New Approach to Antibody Humanization," Methods 36:25-34.
Keir, M.E. et al. (2008, e-pub. Jan. 2, 2008). "PD-1 and Its Ligands in Tolerance and Immunity," Annu. Rev. Immunol. 26:677-704.
Kenanova, V. et al. (Jan. 1, 2010). "Chapter 27: Engineering of the Fe Region for Improved PK (FcRn Interaction)," Antibody Engineering pp. 411-430.
Kenanova, V. et al. (Jan. 15, 2005). "Tailoring the Pharmacokinetics and Positron Emission Tomography Imaging Properties of Anti-Carcinoembryonic Antigen Single-Chain Fv-Fc Antibody Fragments," Cancer Research 65(2):622-631, 23 pages.
Kim, H.-Y. et al. (2018, e-pub. Mar. 12, 2018). "RAGE-Specific Single Chain Fv for PET Imaging of Pancreatic Cancer," PLoS ONE 13(3):e0192821, 14 pages.
Kim, J-K. et al. (1994). "Localization of the Site of the Murine IgGI Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kohler, G. et al. (Aug. 7, 1975) "Continuous Cultures of Fused Cells Secreting Antibody of Predefined Specificity," Nature 256:495-497.
Kozbor, D. (Dec. 1984). "A Human Hybrid Myeloma for Production of Human Monoclonal Antibodies," J. Immunol. 133(6):3001-3005.
Latchman, Y. et al. (Mar. 2001). "PD-L2 Is a Second Ligand for PD-1 and Inhibits T Cell Activation," Nature Immunol. 2(3):261-268.
Lee, C.V. et al. (2004). "Bivalent Antibody Phage Display Mimics Natural Immunoglobulin," .J. Immunol. Methods 284 (1-2):119-132.
Lee, C.V. et al. (2004). "High-Affinity Human Antibodies From Phage-Displayed Synthetic Fab Libraries With a Single Framework Scaffold," J. Mol. Biol. 340:1073-1093.
Lefranc, M.-P. et al. (2015, e-pub. Nov. 5, 2014). "IMGT®, The International ImMunoGeneTics Information System® 25 Years On," Nucleic Acids Res. 43:D413-D422.
Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.
Li, D. et al. (Mar. 5, 2018). "Immuno-PET Imaging of 89Zr Labeled Anti-PD-L1 Domain Antibody," Mol. Pharmaceutics 15(4):1674-1681.
Li, J. et al. (Mar. 7, 2006). "Human Antibodies for Immunotherapy Development Generated via a Human B Cell Hybridoma Technology," Proc. Natl. Acad. Sci. USA 103(10):3557-3562.
Lonberg, N. (Sep. 2005). "Human Antibodies From Transgenic Animals," Nat. Biotech. 23(9):1117-1125.

(56) References Cited

OTHER PUBLICATIONS

Lonberg, N. et al. (2008, e-pub. Jul. 21, 2008). "Fully Human Antibodies From Transgenic Mouse and Phage Display Platforms," Curr. Opin. Immunol. 20:450-459.
Maccallum, R.M. et al. (1996). "Antibody-Antigen Interactions: Contact Analysis and Binding Site Topography," J. Mol. Biol. 262:732-745.
Maggi, A. et al. (Aug. 21, 2016). "Development of a Novel Antibody-Tetrazine Conjugate for Bioorthogonal Pretargeting," Organic & Biomolecular Chemistry 14(31):7544-7551.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
Mccafferty, J. et al. (Dec. 6, 1990). "Phage Antibodies: Filamentous Phage Displaying Antibody Variable Domains," Nature 348:552-554.
Meyer, J.-P. et al. (2018). "Bioorthogonal Masking of Circulation Antibody-TCO Groups Using Tetrazine-Functionalized Dextran Polymers," Bioconjugate Chemistry 29(2):538-545, 17 pages.
Mordenti, J. et al. (1989). "The Use of Interspecies Scaling in Toxicokinetics," Chapter 4 in Toxicokinetics and New Drug Development, Yacobi A. ed et al.; Pergamon Press, New York, pp. 42-96.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Munson, P.J. et al. (1980). "Ligand: A Versatile Computerized Approach for Characterization of Ligand-Binding Systems," Anal. Biochem. 107:220-239.
Ni, J. (2006). "Research Progress and Future Perspectives in Antibodomics and Antibodomic Drugs," Xiandai Mianyixue 26(4):265-268.(Translation of the Abstract 3 pages.).
Nigam, S. et al. (May 1, 2018). "Development of High Affinity Engineered Antibody Fragments Targeting PD-L1 for immunoPET," J. Nucl. Med. 59(1):1101, 3 pages, Abstract.
Nishimura, H. et al. (Jan. 12, 2001). "Autoimmune Dilated Cardiomyopathy in PD-1 Receptor-Deficient Mice," Science 291(5502):319-322.
Nishimura, H. et al. (Aug. 1999). "Development of Lupus-Like Autoimmune Diseases by Disruption of the PD-1 Gene Encoding an ITIM Motif-Carrying Immunoreceptor," Immunity 11(2):141-151.
Nishimura, H. et al. (May 2001). "PD-1: An Inhibitory Immunoreceptor Involved in Peripheral Tolerance," Trends in Immunology 22(5):265-268.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.
Okazaki, T, et al. (Dec. 2003, e-pub. Nov. 2, 2003). "Autoantibodies Against Cardiac Troponin I Are Responsible for Dilated Cardiomyopathy in PD-1-Deficient Mice," Nature Medicine 9(12):1477-1483.
Osbourn, J. et al. (2005). "From Rodent Regents to Human Therapeutics Using Antibody Guided Selection," Methods 36:61-68.
Padlan, E.D. (1991). "A Possible Procedure for Reducing the Immunogenicity of Antibody Variable Domains While Preserving Their Ligand-Binding Properties," Mol. Immunol. 28(4/5):489-498.
Park, J.-J. et al. (Aug. 2010). "B7-HI/CD80 Interaction is Required for the Induction and Maintenance of Peripheral T-2 cell Tolerance," Blood 116(8):1291-1298.
Partial Supplementary European Search Report, dated Mar. 11, 2022, for European Patent Application No. 19811993.5, 19 pages.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Petroff, M.G. et al. (Apr. 2002). "B7 Family Molecules: Novel Immunomodulators at the Maternal-Fetal Interface," Placenta 23(Suppl A):S95-S101.
Plockthun, A. (1992) "Mono- and Bivalent Antibody Fragments Produced in *Escherichia Coli*: Engineering, Folding and Antigen Binding," Immunological Reviews No. 130:151-189.
Plückthun, A. (1994) "Antibodies from *Escherichia coli*," Chapter 11 in Handbook of Experimental Pharmacology 113:269-315.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151(5):2623-2632.
Queen, C. et al. (Dec. 1989). "A Humanized Antibody That Binds to the Interleukin 2 Receptor," Proc. Natl Acad. Sci. USA 86:10029-10033.
Ravetch, J.V. et al. (1991). "Fc Receptors," Annu. Rev. Immunol. 9:457-492.
Remington's Pharmaceutical Sciences. (1980). 16th edition, Osol, A. Ed, pp. 1-2, (Table of Contents Only).
Riechmann, L. et al. (Mar. 24, 1988). "Reshaping Human Antibodies for Therapy," Nature 332:323-327.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Romano, E. et al. (2015, e-pub. Apr. 21, 2015). "The Therapeutic Promise of Disrupting the PD-1/PD-L1 Immune Checkpoint in Cancer: Unleashing The CD8 T Cell Mediated Anti-Tumor Activity Results in Significant, Unprecedented Clinical Efficacy in Various Solid Tumors," Journal for Immunotherapy of Cancer 3:15, 5 pages.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Running Deer, J. et al. (May-Jun. 2004, e-pub. Mar. 10, 2004). "High-Level Expression of Proteins in Mammalian Cells Using Transcription Regulatory Sequences From the Chinese Hamster EF-1Alpha Gene," Biotechnol. Prog. 20(3):880-889.
Sambrook, J. et al. (2001). Molecular Cloning: A Laboratory Manual Cold Spring Harbor Laboratory Press, Cold Spring Harbor,N. Y., 3rd ed., 1 page, Table of Contents.
Shields, R.L. et al. (Mar. 2, 2001), "High Resolution Mapping of the Binding Site on Human IgG1 for FcγRI, FcγRII. FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries of Synthetic Heavy Chain Complementarity Determining Regions," J. Mol. Biol. 338(2):299-310.
Sims, M.J. et al. (Aug. 15, 1993). "A Humanized CD18 Antibody Can Block Function Without Cell Destruction," J. Immunol. 151(4):2296-2308.
Sitaraman, K. et al. (2009). "High-Throughput Protein Expression Using Cell-Free System," Methods Mol. Biol. 498:229-244.
Skerra, A. (1993) "Bacterial Expression of Immunoglobulin Fragments," Current Opinion in Immunology 5:256-262.
Spirin, A.S. (Oct. 2004). "High-Throughput Cell-Free Systems for Synthesis of Functionally Active Proteins," Trends Biotechnol. 22(10):538-545.
Spranger, S. et al. (Aug. 28, 2013). "Up-Regulation of PD-L1, Ido, and Tregs in the Melanoma Tumor Microenvironment Is Driven by CD8+ T Cells," Science Translational Medicine 5(200):200ra116, 21 pages.
Suarez, E.R. et al. (Apr. 29, 2016). "Chimeric Antigen Receptor T Cells Secreting Anti-PD-L1 Antibodies More Effectively Regress Renal Cell Carcinoma in a Humanized Mouse Model," Oncotarget 7(23):34341-34355.
Taube, J.M. et al. (Mar. 28, 2012). "Colocalization of Inflammatory Response With B7-H1 Expression in Human Melanocytic Lesions Supports an Adaptive Resistance Mechanism of Immune Escape," Science Translational Medicine 4(127):127ra137, 22 pages.
Taube, J.M. et al. (Oct. 1, 2015, e-pub. Apr. 8, 2014). "Association of PD-1, PD-1 Ligands, and Other Features of the Tumor Immune

(56) References Cited

OTHER PUBLICATIONS

Microenvironment With Response to Anti-PD-1 Therapy," Clinical Cancer Research 20(19):5064-5074, 23 pages.

Thierauf, J. et al. (Dec. 2015). "Identification and Clinical Relevance of PD-L1 Expression in Primary Mucosal Malignant Melanoma of the Head and Neck," Melanoma Research 25(6):503-509.

Trotter, D.E.G. et al. (2017, e-pub. Jun. 6, 2017). "In Vivo Imaging of the Programmed Death Ligand 1 by 18F PET," J. Nucl. Med. 58(11):1852-1858.

Truillet, C. et al. (2018). "Imaging PD-L1 Expression With ImmunoPET." Bioconjugate Chemistry 29(1):96-103.

Tseng, S.-Y. et al. (Apr. 2, 2001). "B7-Dc, A New Dendritic Cell Molecule with Potent Costimulatory Properties for T Cells," J. Exp. Med. 193(7):839-846.

Van Dijk, M.A. et al. (Aug. 2001). "Human Antibodies as Next Generation Therapeutics," Curr. Opin. Che. Biology 5(4):368-374.

Vollmers, H.P. et al. (2005). "Death by Stress: Natural IgM-Induced Apoptosis," Methods and Findings in Experimental and Clinical Pharmacology 27(3):185-191.

Vollmers, H.P. et al. (2005). "The "Early Birds": Natural igM Antibodies and Immune Surveillance," Histology and Histopathology, 20(3):927-937.

Wang, A. et al. (Apr. 2015, e-pub. Jan. 31, 2015). "The Prognostic Value of PD-L1 Expression For Non-Small Cell Lung Cancer Patients: A Meta-Analysis," European Journal of Surgical Oncology 41(4):450-456.

Waterhouse, P. et al. (1993). "Combinatorial Infection and in Vivo Recombination: a Strategy for Making Large Phage Antibody Repertoires," Nucl. Acids Res. 21(9):2265-2266.

Wei, W. et al. (Apr. 22, 2020). "ImmunoPet: Concept, Design, and Applications," 120(8):3787-3851, 145 pages.

Winter, G. et al. (1994). "Making Antibodies by Phage Display Technology," Ann. Rev. Immunol. 12:433-455.

Wright, A. et al. (Jan. 1997). "Effect of Glycosylation on Antibody Function: Implications for Genetic Engineering," Trends Biotech. 15:26-32.

Xiao, Y. et al. (May 5, 2014). "RGMb Is a Novel Binding Partner for PD-L2 and Its Engagement With PD-L2 Promotes Respiratory Tolerance," The Journal of Experimental Medicine 211(5):943-959.

Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.

Yantha, J. et al. (Oct. 2010, e-pub. Jun. 3, 2010). "Unexpected Acceleration of Type 1 Diabetes by Transgenic Expression of B7-H1 in NOD Mouse Peri-Islet Glia," Diabetes 59(10):2588-2596.

Yao, S. et al. (Aug. 18, 2014, e-pub. Feb. 4, 2013). "Adaptive Resistance: A Tumor Strategy to Evade Immune Attack," European Journal of Immunology 43(3):576-579, 7 pages.

Yao, S. et al. (Jun. 2006, e-pub. May 2, 2006). "Reviving Exhausted T Lymphocytes During Chronic Virus Infection By B7-H1 Blockade," Trends in Molecular Medicine 12(6):244-246.

Zhang, W. et al. (Apr. 2016). "Role of PD-1/PD-L1 Signaling Pathway in Immune Treatment of Malignant Tumors," China Medical Herald 13(12):57-60. English Translation Abstract.

Zou, W. et al. (Jun. 2008). "Inhibitory B7-Family Molecules in the Tumour Microenvironment," Nature reviews Immunology 8(6):467-477.

Alsaab, H. O. et al. (Aug. 23, 2017). "PD-1 and PD-L1 Checkpoint Signaling Inhibition for Cancer Immunotherapy: Mechanism, Combinations, and Clinical Outcome," Frontiers in Pharmacology 561(8):1-15.

Chen, C. et al. (Jun. 15, 1995). "Enhancement and Destruction of Antibody Function by Somatic Mutation: Unequal Occurrence is Controlled by V Gene Combinatorial Associations," The EMBO Journal 14(12):2784-2794.

Extended European Search Report, dated Jun. 14, 2022, for European Patent Application No. 19811993.5, 16 pages.

Extended European Search Report, dated Oct. 25, 2022, for European Patent Application No. 20745563.5, 8 pages.

FDA (Jan. 31, 2018). "Compilation Series of Foreign Laws and Regulations on Foods and Drugs," FDA with English Translation, 10 pages.

Kussie, P.H. et al. (1994). "A Single Engineered Amino Acid Substitution Changes Antibody Fine Specificity ," J. Immunol. 152:146-152.

Yang, D. et al. (Feb. 1, 2018, e-pub. Nov. 24, 2017). "Liposomal Nanohybrid Cerasomes Targeted to PD-L1 Enable Dual-Modality Imaging and Improve Antitumor Treatments," Cancer Letter 414:230-238.

Edwards, B.M. et al. (Nov. 14, 2003). "The Remarkable Flexibility of the Human Antibody Repertoire; Isolation of Over One Thousand Different Antibodies to a Single Protein, BLyS," J. Mol. Biol. 334(1):103-118.

Forsström, B. et al. (Mar. 27, 2015). "Dissecting Antibodies with Regards to Linear and Conformational Epitopes," PLoS One 10(3):e0121673, 11 pages.

Kwon, N.-Y. et al. (2019). "Structural Diversity and Flexibility of Diabodies," Methods 154:136-142.

Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.

Schroeder, H.W. et al. (Feb. 2010). "Structure and Function of Immunolglobulins," Journal of Allergy and Clinical Immunology 125(2, Suppl. 2):S41-S52.

Sela-Culang, I. et al. (2013). "The Structural Basis of Antibody-Antigen Recognition," Frontiers in Immunology 4:302, 13 pages.

Winkler, K. et al. (2000). "Changing the Antigen Binding Specificity by Single Point Mutations of an Anti-p24 (HIV-1 antibody)", J. Immunol. 165(16):4505-4514.

* cited by examiner

CHO/hPD-L1

Lane1. Reduced parental humanized IgG1 control
Lane2. Reduced scFv(PD-L1)
Lane3. Reduced scFv(irrelevant control)
Lane4. Non-reduced parental humanized IgG1 control
Lane5. Non-reduced scFv(PD-L1)
Lane6. Non-reduced scFv(irrelevant control)

60 minutes after injection 120 minutes after injection

SEQUENCE LISTING

```
<160> NUMBER OF SEQ ID NOS: 66

<210> SEQ ID NO 1
<211> LENGTH: 119
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Cys Ile
        35                  40                  45

Gly Arg Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Val Gln Leu Ala Ser Leu Thr Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110
```

Thr Thr Leu Thr Val Ser Ser
        115

<210> SEQ ID NO 2
<211> LENGTH: 357
<212> TYPE: DNA
<213> ORGANISM: Artificial Sequence
<220> FEATURE:
<223> OTHER INFORMATION: Synthetic Construct

<400> SEQUENCE: 2
gaggttcagc tgcagcagtc tggggcagag cttgtgaagc caggggcctc agtcaagttg      60
tcctgcacag cttctggctt caacattaaa gacacctata tgtactgggt gaagcagagg     120
cctgaacagg gcctggagtg cattggaagg attgatcctg cgaatgataa tactaaatat     180
gacccgaagt tccagggcaa ggccactata acagcagaca catcctccaa cacagcctac     240
gtgcagctcg ccagtctgac atctgaggac actgccgtct attactgtgc tagagcgaag     300
aatttgttaa attactttga ctactggggc caaggcacca ctctcacagt ctcctca       357

<210> SEQ ID NO 3
<211> LENGTH: 108
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Leu Gly
1               5                   10                  15

Glu Arg Val Thr Leu Ser Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ile Tyr Pro Leu
                85                  90                  95

Thr Phe Gly Ala Gly Thr Lys Leu Glu Leu Lys Arg
            100                 105

<210> SEQ ID NO 4
<211> LENGTH: 324
<212> TYPE: DNA
<213> ORGANISM: Artificial Sequence
<220> FEATURE:
<223> OTHER INFORMATION: Synthetic Construct

<400> SEQUENCE: 4
gacatccaga tgacccagtc tccatcctcc ttatctgcct ctctgggaga aagagtcact      60
ctcagttgtc gggcaagtca ggaaattagt ggttacttaa gctggcttca gcagaaacca     120
gatggaacta ttaaacgcct gatctacgcc acatcgactt tagattctgg tgtcccaaaa     180
aggttcagtg gcagtaggtc tgggtcagat tattctctca ccatcagcag ccttgagtct     240
gaagattttg cagactatta ctgtctacaa tatgctattt atccgctcac gttcggtgct     300
gggaccaagc tggagctgaa acgg                                           324

```
<210> SEQ ID NO 5
<211> LENGTH: 448
<212> TYPE: PRT
<213> ORGANISM: Artificial Sequence
<220> FEATURE:
<223> OTHER INFORMATION: Synthetic Construct

<400> SEQUENCE: 5
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Cys Ile
        35                  40                  45

Gly Arg Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Val Gln Leu Ala Ser Leu Thr Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu

```
                  370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 6
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 6
gaggttcagc tgcagcagtc tggggcagag cttgtgaagc caggggcctc agtcaagttg      60
tcctgcacag cttctggctt caacattaaa gacacctata tgtactgggt gaagcagagg     120
cctgaacagg gcctggagtg cattggaagg attgatcctg cgaatgataa tactaaatat     180 gaccccgaagt tccagggcaa ggccactata acagcagaca catcctccaa cacagcctac     240
gtgcagctcg ccagtctgac atctgaggac actgccgtct attactgtgc tagagcgaag     300
aatttgttaa attactttga ctactggggc caaggcacca ctctcacagt ctcctcagct     360
agcaccaagg gcccagcgt gttccctctg gcccccagca gcaagagcac cagcggcgga     420
accgccgccc tgggctgcct ggtgaaggac tacttccccg agcccgtgac cgtgtcctgg     480
aacagcggcg ctctgaccag cggagtgcac accttccctg ccgtgctgca gagcagcggc     540
ctgtactccc tgagcagcgt ggtgaccgtg ccagcagca gcctgggcac ccagacctac     600
atctgcaacg tgaaccacaa gcccctccaac accaaggtgg acaagaaggt ggagcctaag     660
agctgcgaca gacccacac ctgccctccc tgccccgccc cgagctgct gggcggaccc      720 agcgtgttcc tgttccctcc caagcccaag gacaccctga tgatcagccg cacccccgag     780
gtgacctgcg tggtggtgga cgtgagccac gaggaccccg aggtgaagtt caactggtac     840
gtggacggcg tggaggtgca caacgccaag accaagcctc gggaggagca gtacaactcc     900
acctaccgcg tggtgagcgt gctgaccgtg ctgcaccagg actggctgaa cggcaaggag     960
tacaagtgca aggtgagcaa caaggccctg cccgctccca tcgagaagac catcagcaag    1020
gccaagggcc agccccggga gcctcaggtg tacaccctgc cccccagccg cgacgagctg    1080
accaagaacc aggtgagcct gacctgcctg gtgaagggct tctacccctc cgacatcgcc    1140
gtggagtggg agagcaacgg ccagcctgag aacaactaca gaccacccc tcccgtgctg    1200 gacagcgacg gcagcttctt cctgtacagc aagctgaccg tggacaagtc ccggtggcag    1260
cagggcaacg tgttcagctg cagcgtgatg cacgaggccc tgcacaacca ctacacccag    1320
aagagcctga gcctgagccc cggatagtaa                                      1350

<210> SEQ ID NO 7
<211> LENGTH: 214
<212> TYPE: PRT
<213> ORGANISM: Artificial Sequence
<220> FEATURE:
<223> OTHER INFORMATION: Synthetic Construct

<400> SEQUENCE: 7
```

Asp Ile Gln Met Thr Gln Ser Pro Ser Ser Leu Ser Ala Ser Leu Gly
1               5                   10                  15

Glu Arg Val Thr Leu Ser Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Thr Ser Thr Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ile Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 645
<212> TYPE: DNA
<213> ORGANISM: Artificial Sequence
<220> FEATURE:
<223> OTHER INFORMATION: Synthetic Construct

<400> SEQUENCE: 8
gacatccaga tgacccagtc tccatcctcc ttatctgcct ctctgggaga aagagtcact    60
ctcagttgtc gggcaagtca ggaaattagt ggttacttaa gctggcttca gcagaaacca   120
gatggaacta ttaaacgcct gatctacgcc acatcgactt tagattctgg tgtcccaaaa   180
aggttcagtg gcagtaggtc tgggtcagat tattctctca ccatcagcag ccttgagtct   240
gaagattttg cagactatta ctgtctacaa tatgctattt atccgctcac gttcggtgct   300
gggaccaagc tggagctgaa acggaccgtg gccgccccca gcgtgttcat cttccctccc   360
agcgacgagc agctgaagtc tggcaccgcc agcgtggtgt gcctgctgaa caacttctac   420
ccccgcgagg ccaaggtgca gtggaaggtg gacaacgccc tgcagagcgg caacagccag   480
gagagcgtga ccgagcagga ctccaaggac agcacctaca gcctgagcag caccctgacc   540
ctgagcaagg ccgactacga aagcacaag gtgtacgcct gcgaggtgac ccaccaggga   600
ctgtctagcc ccgtgaccaa gagcttcaac cggggcgagt gctaa               645

<210> SEQ ID NO 9
<211> LENGTH: 119
<212> TYPE: PRT

<213> ORGANISM: Artificial Sequence
<220> FEATURE:
<223> OTHER INFORMATION: Synthetic Construct

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115
```

<210> SEQ ID NO 10
<211> LENGTH: 357
<212> TYPE: DNA
<213> ORGANISM: Artificial Sequence
<220> FEATURE:
<223> OTHER INFORMATION: Synthetic Construct

<400> SEQUENCE: 10

```
caggttcagc tggtgcagtc tggggcagag gttaagaagc caggggcctc agtcaaggtg      60
tcctgcaaag cttctggctt caacattaaa gacacctata tgtactgggt gaggcaggca     120
cctggacagg gcctggagtg gatgggaagg attgatcctg cgaatgataa tactaaatat     180
gcccagaagt tccagggcag ggtcactata acagcagaca catccaccag cacagcctac     240
atggagctct ccagtctgag atctgaggac actgccgtct attactgtgc tagagcgaag     300
aatttgttaa attactttga ctactggggc caaggcaccc ttgtcacagt ctcctca        357
```

<210> SEQ ID NO 11
<211> LENGTH: 119
<212> TYPE: PRT
<213> ORGANISM: Artificial Sequence
<220> FEATURE:
<223> OTHER INFORMATION: Synthetic Construct

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Ile
        35                  40                  45

Gly Arg Ile Asp Pro Ala Asn Asp Asn Thr Lys Tyr Ala Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 12
<211> LENGTH: 357
<212> TYPE: DNA
<213> ORGANISM: Artificial Sequence
<220> FEATURE:
<223> OTHER INFORMATION: Synthetic Construct

<400> SEQUENCE: 12
caggttcagc tggtgcagtc tggggcagag gttaagaagc caggggcctc agtcaaggtg      60
tcctgcaaag cttctggctt caacattaaa gacacctata tgtactgggt gaggcaggca     120
cctggacagg gcctggagtg gattggaagg attgatcctg cgaatgataa tactaaatat     180
gccccgaagt tccagggcag ggtcactata acagcagaca catccaccaa cacagcctac     240
atggagctct ccagtctgag atctgaggac actgccgtct attactgtgc tagagcgaag     300
aatttgttaa attactttga ctactggggc caaggcaccc ttgtcacagt ctcctca       357

<210> SEQ ID NO 13
<211> LENGTH: 119
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser
        115

<210> SEQ ID NO 14
<211> LENGTH: 357
<212> TYPE: DNA
<213> ORGANISM: Artificial Sequence
<220> FEATURE:
<223> OTHER INFORMATION: Synthetic Construct

<400> SEQUENCE: 14
gaggttcagc tggtgcagtc tggggcagag gttaagaagc caggggcctc agtcaaggtg      60
tcctgcaaag cttctggctt caacattaaa gacacctata tgtactgggt gaggcaggca     120
cctggacagg gcctggagtg gatgggaagg attgatcctg cgaatgataa tactaaatat     180

```
gcccagaagt tccagggcag ggtcactata acagcagaca catccaccaa cacagcctac      240
atggagctct ccagtctgag atctgaggac actgccgtct attactgtgc tagagcgaag      300
aatttgttaa attactttga ctactggggc caaggcaccc ttgtcacagt ctcctca         357
```

<210> SEQ ID NO 15
<211> LENGTH: 108
<212> TYPE: PRT
<213> ORGANISM: Artificial Sequence
<220> FEATURE:
<223> OTHER INFORMATION: Synthetic Construct

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Thr Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ile Tyr Pro Leu
                85                  90                  95

Thr Phe Gly Gln Gly Thr Lys Leu Glu Ile Lys Arg
            100                 105
```

<210> SEQ ID NO 16
<211> LENGTH: 309
<212> TYPE: DNA
<213> ORGANISM: Artificial Sequence
<220> FEATURE:
<223> OTHER INFORMATION: Synthetic Construct

<400> SEQUENCE: 16

```
gacatccaga tgacccagtc tccatcctcc ttatctgcct ctgtgggaga tagagtcact      60
atcacttgtc gggcaagtca ggaaattagt ggttacttaa gctggtatca gcagaaaaaa     120
cgcctgatct acgccacatc gactttagat tctggtgtcc caagtaggtt cagtggcagt     180
gggtctggga cagattttac tctcaccatc agcagcctca gcctgaaga ttttgcaacc      240 tattactgtc tacaatatgc tatttatccg ctcacgttcg gtcaggggac caagctggag     300
atcaaacgg                                                             309
```

<210> SEQ ID NO 17
<211> LENGTH: 108
<212> TYPE: PRT
<213> ORGANISM: Artificial Sequence
<220> FEATURE:
<223> OTHER INFORMATION: Synthetic Construct

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Lys Arg Leu Ile
        35                  40                  45

Tyr Ala Thr Ser Thr Leu Gln Ser Gly Val Pro Ser Arg Phe Ser Gly
```

```
                    50                  55                  60
Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Gln Gly Thr Lys Leu Glu Ile Lys Arg
            100                 105

<210> SEQ ID NO 18
<211> LENGTH: 324
<212> TYPE: DNA
<213> ORGANISM: Artificial Sequence
<220> FEATURE:
<223> OTHER INFORMATION: Synthetic Construct

<400> SEQUENCE: 18
gacatccaga tgacccagtc tccatcctcc ttatctgcct ctgtgggaga tagagtcact    60
atcacttgtc gggcaagtca ggaaattagt ggttacttaa gctggcttca gcagaaacca   120
ggtaaggctc ctaaacgcct gatctacgcc acatcgactt acagtctggg tgtcccaagt   180
aggttcagtg gcagtaggtc tgggacagat tatactctca ccatcagcag ccttcagcct   240
gaagattttg caacctatta ctgtctacaa tatgctattt atccgctcac gttcggtcag   300
gggaccaagc tggagatcaa acgg                                          324

<210> SEQ ID NO 19
<211> LENGTH: 108
<212> TYPE: PRT
<213> ORGANISM: Artificial Sequence
<220> FEATURE:
<223> OTHER INFORMATION: Synthetic Construct

<400> SEQUENCE: 19

Asp Ile Gln Met Thr Gln Ser Pro Ser Leu Ser Ala Ser Val Gly
  1               5                  10                  15

Asp Arg Val Thr Ile Thr Cys Arg Ala Ser Gln Glu Ile Ser Gly Tyr
                 20                  25                  30

Leu Ser Trp Tyr Gln Gln Lys Pro Gly Lys Ala Pro Lys Arg Leu Ile
             35                  40                  45

Tyr Ala Thr Ser Thr Leu Asp Ser Gly Val Pro Ser Arg Phe Ser Gly
         50                  55                  60

Ser Arg Ser Gly Ser Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Gln Gly Thr Lys Leu Glu Ile Lys Arg
            100                 105

<210> SEQ ID NO 20
<211> LENGTH: 324
<212> TYPE: DNA
<213> ORGANISM: Artificial Sequence
<220> FEATURE:
<223> OTHER INFORMATION: Synthetic Construct

<400> SEQUENCE: 20
gacatccaga tgacccagtc tccatcctcc ttatctgcct ctgtgggaga tagagtcact    60
atcacttgtc gggcaagtca ggaaattagt ggttacttaa gctggtatca gcagaaacca   120
ggtaaggctc ctaaacgcct gatctacgcc acatcgactt tagattctgg tgtcccaagt   180
```

-continued

```
aggttcagtg gcagtaggtc tgggtcagat tatactctca ccatcagcag ccttcagcct    240
gaagattttg caacctatta ctgtctacaa tatgctattt atccgctcac gttcggtcag    300
gggaccaagc tggagatcaa acgg                                           324
```

<210> SEQ ID NO 21
<211> LENGTH: 471
<212> TYPE: PRT
<213> ORGANISM: Artificial Sequence
<220> FEATURE:
<223> OTHER INFORMATION: Synthetic Construct

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Gly Ser Thr Ser Gly Ser Gly Lys Pro
        115                 120                 125

Gly Ser Gly Glu Gly Ser Thr Lys Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Glu Ile Ser Gly Tyr Leu Ser Trp Leu Gln Gln Lys
                165                 170                 175

Pro Gly Lys Ala Pro Lys Arg Leu Ile Tyr Ala Thr Ser Thr Leu Gln
            180                 185                 190

Ser Gly Val Pro Ser Arg Phe Ser Gly Ser Arg Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Leu Gln Tyr Ala Ile Tyr Pro Leu Thr Phe Gly Gln Gly Thr Lys
225                 230                 235                 240

Leu Glu Ile Lys Arg Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335
```

```
Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly
465                 470

<210> SEQ ID NO 22
<211> LENGTH: 1419
<212> TYPE: DNA
<213> ORGANISM: Artificial Sequence
<220> FEATURE:
<223> OTHER INFORMATION: Synthetic Construct

<400> SEQUENCE: 22
caggttcagc tggtgcagtc tggggcagag gttaagaagc caggggcctc agtcaaggtg      60
tcctgcaagg cttctggctt caacattaaa gacacctata tgtactgggt gaggcaggca     120
cctggacagg gcctggagtg gatgggaagg attgatcctg cgaatgataa tactaaatat     180
gcccagaagt tccagggcag ggtcactata acagcagaca catccaccag cacagcctac     240
atggagctct ccagtctgag atctgaggac actgccgtct attactgtgc tagagcgaag     300
aatttgttaa attactttga ctactggggc caaggcaccc ttgtcacagt ctcctcaggc     360
agcacctccg gcagcggcaa gctggcagc ggcgagggca gcaccaaggg cgacatccag     420
atgacccagt ctccatcctc cttatctgcc tctgtgggag atagagtcac tatcacttgt     480
cgggcaagtc aggaaattag tggttactta agctggcttc agcagaaacc aggtaaggct     540
cctaaacgcc tgatctacgc cacatcgact ttacagtctg gtgtcccaag taggttcagt     600
ggcagtaggt ctgggacaga ttatactctc accatcagca gccttcagcc tgaagatttt     660
gcaacctatt actgtctaca atatgctatt tatccgctca cgttcggtca ggggaccaag     720
ctggagatca acgggacaa gacccacacc tgccctccct gccccgcccc cgagctgctg     780
ggcggaccca gcgtgttcct gttccctccc aagcccaagg acaccctgat gatcagccgc     840
acccccgagg tgacctgcgt ggtggtggac gtgagccacg aggaccccga ggtgaagttc     900
aactggtacg tggacggcgt ggaggtgcac aacgccaaga ccaagcctcg ggaggagcag     960
tacaactcca cctaccgcgt ggtgagcgtg ctgaccgtgc tgcaccagga ctggctgaac    1020
ggcaaggagt acaagtgcaa ggtgagcaac aaggccctgc cgctcccat cgagaagacc    1080
atcagcaagg ccaagggcca gccccgggag cctcaggtgt acaccctgcc cccagccgc    1140
gacgagctga ccaagaacca ggtgagcctg acctgcctgg tgaagggctt ctaccctcc    1200
gacatcgccg tggagtggga gagcaacggc cagcctgaga caactacaa gaccacccct    1260
```

-continued

```
cccgtgctgg acagcgacgg cagcttcttc ctgtacagca agctgaccgt ggacaagtcc      1320
cggtggcagc agggcaacgt gttcagctgc agcgtgatgc acgaggccct gcacaaccac      1380
tacacccaga agagcctgag cctgagcccc ggataataa                             1419
```

<210> SEQ ID NO 23
<211> LENGTH: 471
<212> TYPE: PRT
<213> ORGANISM: Artificial Sequence
<220> FEATURE:
<223> OTHER INFORMATION: Synthetic Construct

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Gly Ser Thr Ser Gly Ser Gly Lys Pro
        115                 120                 125

Gly Ser Gly Glu Gly Ser Thr Lys Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Glu Ile Ser Gly Tyr Leu Ser Trp Leu Gln Gln Lys
                165                 170                 175

Pro Gly Lys Ala Pro Lys Arg Leu Ile Tyr Ala Thr Ser Thr Leu Gln
            180                 185                 190

Ser Gly Val Pro Ser Arg Phe Ser Gly Ser Arg Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Leu Gln Tyr Ala Ile Tyr Pro Leu Thr Phe Gly Gln Gly Thr Lys
225                 230                 235                 240

Leu Glu Ile Lys Arg Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu Ala Gln
                325                 330                 335
```

```
Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn Gln Tyr Thr Gln Lys
            450                 455                 460

Ser Leu Ser Leu Ser Pro Gly
465                 470

<210> SEQ ID NO 24
<211> LENGTH: 1419
<212> TYPE: DNA
<213> ORGANISM: Artificial Sequence
<220> FEATURE:
<223> OTHER INFORMATION: Synthetic Construct

<400> SEQUENCE: 24
caggttcagc tggtgcagtc tggggcagag gttaagaagc caggggcctc agtcaaggtg     60
tcctgcaagg cttctggctt caacattaaa gacacctata tgtactgggt gaggcaggca    120
cctggacagg gcctggagtg gatgggaagg attgatcctg cgaatgataa tactaaatat    180
gcccagaagt tccagggcag ggtcactata acagcagaca catccaccag cacagcctac    240
atggagctct ccagtctgag atctgaggac actgccgtct attactgtgc tagagcgaag    300
aatttgttaa attactttga ctactggggc caaggcaccc ttgtcacagt ctcctcaggc    360
agcacctccg gcagcggcaa gctggcagc ggcgagggca gcaccaaggg cgacatccag    420
atgacccagt ctccatcctc cttatctgcc tctgtgggag atagagtcac tatcacttgt    480
cgggcaagtc aggaaattag tggttactta agctggcttc agcagaaacc aggtaaggct    540
cctaaacgcc tgatctacgc cacatcgact ttacagtctg gtgtcccaag taggttcagt    600
ggcagtaggt ctgggacaga ttatactctc accatcagca gccttcagcc tgaagatttt    660
gcaacctatt actgtctaca aatgctatt tatccgctca cgttcggtca ggggaccaag    720
ctggagatca acgggacaa gacccacacc tgccctccct gccccgcccc cgagctgctg    780
ggcggaccca gcgtgttcct gttccctccc aagcccaagg acaccctgat gatcagccgc    840
acccccgagg tgacctgcgt ggtggtggac gtgagccacg aggaccccga ggtgaagttc    900
aactggtacg tggacggcgt ggaggtgcac aacgccaaga ccaagcctcg ggaggagcag    960
tacaactcca cctaccgcgt ggtgagcgtg ctgaccgtgc tggcccagga ctggctgaac   1020
ggcaaggagt acaagtgcaa ggtgagcaac aaggccctgc cgctcccat cgagaagacc   1080
atcagcaagg ccaagggcca gccccgggag cctcaggtgt acaccctgcc ccccagccgc   1140
gacgagctga ccaagaacca ggtgagcctg acctgcctgg tgaagggctt ctaccccct cc   1200
gacatcgccg tggagtggga gagcaacggc cagcctgaga caactacaa gaccacccct   1260
```
cccgtgctgg acagcgacgg cagcttcttc ctgtacagca agctgaccgt ggacaagtcc   1320
cggtggcagc agggcaacgt gttcagctgc agcgtgatgc acgaggccct gcacaaccag   1380
tacacccaga agagcctgag cctgagcccc ggataataa                         1419

<210> SEQ ID NO 25
<211> LENGTH: 247
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Glu Ile Ser Gly Tyr Leu Ser Trp Leu Gln
                165                 170                 175

Gln Lys Pro Gly Lys Ala Pro Lys Arg Leu Ile Tyr Ala Thr Ser Thr
            180                 185                 190

Leu Gln Ser Gly Val Pro Ser Arg Phe Ser Gly Ser Arg Ser Gly Thr
        195                 200                 205

Asp Tyr Thr Leu Thr Ile Ser Ser Leu Gln Pro Glu Asp Phe Ala Thr
    210                 215                 220

Tyr Tyr Cys Leu Gln Tyr Ala Ile Tyr Pro Leu Thr Phe Gly Gln Gly
225                 230                 235                 240

Thr Lys Leu Glu Ile Lys Arg
                245

<210> SEQ ID NO 26
<211> LENGTH: 774
<212> TYPE: DNA
<213> ORGANISM: Artificial Sequence
<220> FEATURE:
<223> OTHER INFORMATION: Synthetic Construct

<400> SEQUENCE: 26
caggttcagc tggtgcagtc tggggcagag gttaagaagc caggggcctc agtcaaggtg    60
tcctgcaagg cttctggctt caacattaaa gacacctata tgtactgggt gaggcaggca   120

-continued

```
cctggacagg gcctggagtg gatgggaagg attgatcctg cgaatgataa tactaaatat    180
gcccagaagt tccagggcag ggtcactata acagcagaca catccaccag cacagcctac    240
atggagctct ccagtctgag atctgaggac actgccgtct attactgtgc tagagcgaag    300
aatttgttaa attactttga ctactggggc caaggcaccc ttgtcacagt ctcctcaggt    360
ggcggtggct ctggaggtgg tgggagcggt ggcggcggat ctgggggtgg cggaagcgac    420
atccagatga cccagtctcc atcctcctta tctgcctctg tgggagatag agtcactatc    480
acttgtcggg caagtcagga aattagtggt tacttaagct ggcttcagca gaaaccaggt    540
aaggctccta aacgcctgat ctacgccaca tcgactttac agtctggtgt cccaagtagg    600
ttcagtggca gtaggtctgg gacagattat actctcacca tcagcagcct tcagcctgaa    660
gattttgcaa cctattactg tctacaatat gctatttatc cgctcacgtt cggtcagggg    720
accaagctgg agatcaaacg gggaggtggt gggtctcacc atcaccatca ccat          774
```

<210> SEQ ID NO 27
<211> LENGTH: 245
<212> TYPE: PRT
<213> ORGANISM: Artificial Sequence
<220> FEATURE:
<223> OTHER INFORMATION: Synthetic Construct

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Gly Ser Thr Ser Gly Gly Lys Pro
        115                 120                 125

Gly Ser Gly Glu Gly Ser Thr Lys Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Glu Ile Ser Gly Tyr Leu Ser Trp Leu Gln Gln Lys
                165                 170                 175

Pro Gly Lys Ala Pro Lys Arg Leu Ile Tyr Ala Thr Ser Thr Leu Gln
            180                 185                 190

Ser Gly Val Pro Ser Arg Phe Ser Gly Ser Arg Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Leu Gln Tyr Ala Ile Tyr Pro Leu Thr Phe Gly Gln Gly Thr Lys
225                 230                 235                 240

Leu Glu Ile Lys Arg
                245
```

<210> SEQ ID NO 28
<211> LENGTH: 768
<212> TYPE: DNA
<213> ORGANISM: Artificial Sequence
<220> FEATURE:
<223> OTHER INFORMATION: Synthetic Construct

<400> SEQUENCE: 28

```
caggttcagc tggtgcagtc tggggcagag gttaagaagc caggggcctc agtcaaggtg      60
tcctgcaagg cttctggctt caacattaaa gacacctata tgtactgggt gaggcaggca     120
cctggacagg gcctggagtg gatgggaagg attgatcctg cgaatgataa tactaaatat     180
gcccagaagt tccagggcag ggtcactata acagcagaca catccaccag cacagcctac     240
atggagctct ccagtctgag atctgaggac actgccgtct attactgtgc tagagcgaag     300
aatttgttaa attactttga ctactggggc caaggcaccc ttgtcacagt ctcctcaggc     360
agcacctccg gcagcggcaa gcctggcagc ggcgagggca gcaccaaggg cgacatccag     420
atgacccagt ctccatcctc cttatctgcc tctgtgggag atagagtcac tatcacttgt     480
cgggcaagtc aggaaattag tggttactta agctggcttc agcagaaacc aggtaaggct     540
cctaaacgcc tgatctacgc cacatcgact ttacagtctg gtgtcccaag taggttcagt     600
ggcagtaggt ctgggacaga ttatactctc accatcagca gccttcagcc tgaagatttt     660
gcaacctatt actgtctaca atatgctatt tatccgctca cgttcggtca ggggaccaag     720
ctggagatca aacggggagg tggtgggtct caccatcacc atcaccat                 768
```

<210> SEQ ID NO 29
<211> LENGTH: 247
<212> TYPE: PRT
<213> ORGANISM: Artificial Sequence
<220> FEATURE:
<223> OTHER INFORMATION: Synthetic Construct

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Cys Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Lys Asn Leu Leu Asn Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Glu Ile Ser Gly Tyr Leu Ser Trp Leu Gln
                165                 170                 175
```

Gln Lys Pro Gly Lys Ala Pro Lys Arg Leu Ile Tyr Ala Thr Ser Thr
            180                 185                 190

Leu Gln Ser Gly Val Pro Ser Arg Phe Ser Gly Ser Arg Ser Gly Thr
            195                 200                 205

Asp Tyr Thr Leu Thr Ile Ser Ser Leu Gln Pro Glu Asp Phe Ala Thr
210                 215                 220

Tyr Tyr Cys Leu Gln Tyr Ala Ile Tyr Pro Leu Thr Phe Gly Cys Gly
225                 230                 235                 240

Thr Lys Leu Glu Ile Lys Arg
            245

<210> SEQ ID NO 30
<211> LENGTH: 774
<212> TYPE: DNA
<213> ORGANISM: Artificial Sequence
<220> FEATURE:
<223> OTHER INFORMATION: Synthetic Construct

<400> SEQUENCE: 30
caggttcagc tggtgcagtc tggggcagag gttaagaagc caggggcctc agtcaaggtg      60
tcctgcaagg cttctggctt caacattaaa gacacctata tgtactgggt gaggcaggca     120
cctggacagt gcctggagtg gatgggaagg attgatcctg ccaatgataa tactaaatat     180
gcccagaagt tccagggcag ggtcactata acagcagaca catccaccag cacagcctac     240
atggagctct ccagtctgag atctgaggac actgccgtct attactgtgc tagagccaag     300
aatttgttaa attactttga ctactggggc caaggcaccc ttgtcacagt ctcctcaggt     360
ggcggtggct ctgaggtggt gggagcggt ggcggcggat ctgggggtgg cggaagcgac     420
atccagatga cccagtctcc atcctcctta tctgcctctg tgggagatag agtcactatc     480
acttgtcggg caagtcagga aattagtggt tacttaagct ggcttcagca gaaaccaggt     540
aaggctccta aacgcctgat ctacgccaca tccactttac agtctggtgt cccaagtagg     600
ttcagtggca gtaggtctgg gacagattat actctcacca tcagcagcct tcagcctgaa     660
gattttgcaa cctattactg tctacaatat gctatttatc ctctcacctt cggttgtggg     720
accaagctgg agatcaaacg ggaggtggt gggtctcacc atcaccatca ccat            774

<210> SEQ ID NO 31
<211> LENGTH: 247
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Arg Ile Asp Pro Ala Asn Asp Asn Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ala Lys Asn Leu Leu Asn Tyr Phe Asp Tyr Trp Gly Cys Gly
            100                 105                 110

Thr Leu Val Thr Val Ser Ser Gly Gly Gly Ser Gly Gly Gly Gly
        115                 120                 125

Ser Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Glu Ile Ser Gly Tyr Leu Ser Trp Leu Gln
                165                 170                 175

Gln Lys Pro Gly Lys Cys Pro Lys Arg Leu Ile Tyr Ala Thr Ser Thr
            180                 185                 190

Leu Gln Ser Gly Val Pro Ser Arg Phe Ser Gly Ser Arg Ser Gly Thr
        195                 200                 205

Asp Tyr Thr Leu Thr Ile Ser Ser Leu Gln Pro Glu Asp Phe Ala Thr
    210                 215                 220

Tyr Tyr Cys Leu Gln Tyr Ala Ile Tyr Pro Leu Thr Phe Gly Gln Gly
225                 230                 235                 240

Thr Lys Leu Glu Ile Lys Arg
            245
```

<210> SEQ ID NO 32
<211> LENGTH: 774
<212> TYPE: DNA
<213> ORGANISM: Artificial Sequence
<220> FEATURE:
<223> OTHER INFORMATION: Synthetic Construct

<400> SEQUENCE: 32

```
caggttcagc tggtgcagtc tggggcagag gttaagaagc caggggcctc agtcaaggtg    60
tcctgcaagg cttctggctt caacattaaa gacacctata tgtactgggt gaggcaggca   120
cctggacagg gcctggagtg gatgggaagg attgatcctg cgaatgataa tactaaatat   180
gcccagaagt tccagggcag ggtcactata acagcagaca catccaccag cacagcctac   240
atggagctct ccagtctgag atctgaggac actgccgtct attactgtgc tagagcgaag   300
aatttgttaa attactttga ctactggggc tgcggcaccc ttgtcacagt ctcctcaggt   360
ggcggtggct ctgaggtgg tgggagcggt ggcggcggat ctggggtgg cggaagcgac   420
atccagatga cccagtctcc atcctcctta tctgcctctg tgggagatag agtcactatc   480
acttgtcggg caagtcagga aattagtggt tacttaagct ggcttcagca gaaaccaggt   540
aagtgtccta aacgcctgat ctacgccaca tcgactttac agtctggtgt cccaagtagg   600
ttcagtggca gtaggtctgg gacagattat actctcacca tcagcagcct tcagcctgaa   660
gattttgcaa cctattactg tctacaatat gctatttatc cgctcacgtt cggtcagggg   720
accaagctgg agatcaaacg gggaggtggt gggtctcacc atcaccatca ccat         774
```

<210> SEQ ID NO 33
<211> LENGTH: 247
<212> TYPE: PRT
<213> ORGANISM: Artificial Sequence
<220> FEATURE:
<223> OTHER INFORMATION: Synthetic Construct

<400> SEQUENCE: 33

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Glu Ile Ser Gly Tyr
         20                  25                  30

Leu Ser Trp Leu Gln Gln Lys Pro Gly Lys Ala Pro Lys Arg Leu Ile
         35                  40                  45

Tyr Ala Thr Ser Thr Leu Gln Ser Gly Val Pro Ser Arg Phe Ser Gly
 50                  55                  60

Ser Arg Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Leu
                 85                  90                  95

Thr Phe Gly Gln Gly Thr Lys Leu Glu Ile Lys Arg Gly Gly Gly Gly
             100                 105                 110

Ser Gly Gly Gly Gly Ser Gly Gly Gly Gly Ser Gly Gly Gly Gly Ser
             115                 120                 125

Gln Val Gln Leu Val Gln Ser Gly Ala Glu Val Lys Lys Pro Gly Ala
         130                 135                 140

Ser Val Lys Val Ser Cys Lys Ala Ser Gly Phe Asn Ile Lys Asp Thr
145                 150                 155                 160

Tyr Met Tyr Trp Val Arg Gln Ala Pro Gly Gln Gly Leu Glu Trp Met
                 165                 170                 175

Gly Arg Ile Asp Pro Ala Asn Asp Asn Thr Lys Tyr Ala Gln Lys Phe
             180                 185                 190

Gln Gly Arg Val Thr Ile Thr Ala Asp Thr Ser Thr Ser Thr Ala Tyr
         195                 200                 205

Met Glu Leu Ser Ser Leu Arg Ser Glu Asp Thr Ala Val Tyr Tyr Cys
     210                 215                 220

Ala Arg Ala Lys Asn Leu Leu Asn Tyr Phe Asp Tyr Trp Gly Gln Gly
225                 230                 235                 240

Thr Leu Val Thr Val Ser Ser
             245

<210> SEQ ID NO 34
<211> LENGTH: 774
<212> TYPE: DNA
<213> ORGANISM: Artificial Sequence
<220> FEATURE:
<223> OTHER INFORMATION: Synthetic Construct

<400> SEQUENCE: 34
gacatccaga tgacccagtc tccatcctcc ttatctgcct ctgtgggaga tagagtcact     60
atcacttgtc gggcaagtca ggaaattagt ggttacttaa gctggcttca gcagaaacca    120
ggtaaggctc ctaaacgcct gatctacgcc acatcgactt acagtctggg tgtcccaagt    180
aggttcagtg gcagtaggtc tgggacagat tatactctca ccatcagcag ccttcagcct    240
gaagattttg caacctatta ctgtctacaa tatgctattt atccgctcac gttcggtcag    300
gggaccaagc tggagatcaa acgggtggc ggtggctctg gaggtggtgg agcggtggc     360 ggcggatctg ggggtggcgg aagccaggtt cagctggtgc agtctggggc agaggttaag    420
aagccagggg cctcagtcaa ggtgtcctgc aaggcttctg gcttcaacat taaagacacc    480
tatatgtact gggtgaggca ggcacctgga cagggcctgg agtggatggg aaggattgat    540
cctgcgaatg ataatactaa atatgcccag aagttccagg gcagggtcac tataacagca    600
gacacatcca ccagcacagc ctacatggag ctctccagtc tgagatctga ggacactgcc    660
gtctattact gtgctagagc gaagaatttg ttaaattact tgactactg gggccaaggc    720 accccttgtca cagtctcctc aggaggcgga gggtctcacc atcaccatca ccat         774

```
<210> SEQ ID NO 35
<211> LENGTH: 245
<212> TYPE: PRT
<213> ORGANISM: Artificial Sequence
<220> FEATURE:
<223> OTHER INFORMATION: Synthetic Construct

<400> SEQUENCE: 35
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Lys Arg Leu Ile
        35                  40                  45

Tyr Ala Thr Ser Thr Leu Gln Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Leu
                85                  90                  95

Thr Phe Gly Gln Gly Thr Lys Leu Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Phe Asn Ile Lys Asp Thr Tyr Met
145                 150                 155                 160

Tyr Trp Val Arg Gln Ala Pro Gly Gln Gly Leu Glu Trp Met Gly Arg
                165                 170                 175

Ile Asp Pro Ala Asn Asp Asn Thr Lys Tyr Ala Gln Lys Phe Gln Gly
            180                 185                 190

Arg Val Thr Ile Thr Ala Asp Thr Ser Thr Ser Thr Ala Tyr Met Glu
        195                 200                 205

Leu Ser Ser Leu Arg Ser Glu Asp Thr Ala Val Tyr Tyr Cys Ala Arg
    210                 215                 220

Ala Lys Asn Leu Leu Asn Tyr Phe Asp Tyr Trp Gly Gln Gly Thr Leu
225                 230                 235                 240

Val Thr Val Ser Ser
            245

```
<210> SEQ ID NO 36
<211> LENGTH: 768
<212> TYPE: DNA
<213> ORGANISM: Artificial Sequence
<220> FEATURE:
<223> OTHER INFORMATION: Synthetic Construct

<400> SEQUENCE: 36
```
gacatccaga tgacccagtc tccatcctcc ttatctgcct ctgtgggaga tagagtcact     60
atcacttgtc gggcaagtca ggaaattagt ggttacttaa gctggcttca gcagaaacca   120
ggtaaggctc ctaaacgcct gatctacgcc acatcgactt tacagtctgg tgtcccaagt   180
aggttcagtg gcagtaggtc tgggacagat tatactctca ccatcagcag ccttcagcct   240

```
gaagattttg caacctatta ctgtctacaa tatgctattt atccgctcac gttcggtcag    300
gggaccaagc tggagatcaa acggggcagc acctccggca gcggcaagcc tggcagcggc    360
gagggcagca ccaagggcca ggttcagctg gtgcagtctg ggcagaggt taagaagcca     420 ggggcctcag tcaaggtgtc ctgcaaggct tctggcttca acattaaaga cacctatatg    480
tactgggtga ggcaggcacc tggacagggc ctggagtgga tgggaaggat tgatcctgcg    540
aatgataata ctaaatatgc ccagaagttc cagggcaggg tcactataac agcagacaca    600
tccaccagca cagcctacat ggagctctcc agtctgagat ctgaggacac tgccgtctat    660
tactgtgcta gagcgaagaa tttgttaaat tactttgact actggggcca aggcacccttt   720 gtcacagtct cctcaggagg cggagggtct caccatcacc atcaccat                 768
```

<210> SEQ ID NO 37
<211> LENGTH: 247
<212> TYPE: PRT
<213> ORGANISM: Artificial Sequence
<220> FEATURE:
<223> OTHER INFORMATION: Synthetic Construct

<400> SEQUENCE: 37

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Cys Pro Lys Arg Leu Ile
        35                  40                  45

Tyr Ala Thr Ser Thr Leu Gln Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Leu
                85                  90                  95

Thr Phe Gly Gln Gly Thr Lys Leu Glu Ile Lys Arg Gly Gly Gly Gly
           100                 105                 110

Ser Gly Gly Gly Gly Ser Gly Gly Gly Ser Gly Gly Gly Gly Ser
       115                 120                 125

Gln Val Gln Leu Val Gln Ser Gly Ala Glu Val Lys Lys Pro Gly Ala
   130                 135                 140

Ser Val Lys Val Ser Cys Lys Ala Ser Gly Phe Asn Ile Lys Asp Thr
145                 150                 155                 160

Tyr Met Tyr Trp Val Arg Gln Ala Pro Gly Gln Gly Leu Glu Trp Met
               165                 170                 175

Gly Arg Ile Asp Pro Ala Asn Asp Asn Thr Lys Tyr Ala Gln Lys Phe
           180                 185                 190

Gln Gly Arg Val Thr Ile Thr Ala Asp Thr Ser Thr Ser Thr Ala Tyr
       195                 200                 205

Met Glu Leu Ser Ser Leu Arg Ser Glu Asp Thr Ala Val Tyr Tyr Cys
   210                 215                 220

Ala Arg Ala Lys Asn Leu Leu Asn Tyr Phe Asp Tyr Trp Gly Cys Gly
225                 230                 235                 240

Thr Leu Val Thr Val Ser Ser
                245
```

<210> SEQ ID NO 38
<211> LENGTH: 774

```
<212> TYPE: DNA
<213> ORGANISM: Artificial Sequence
<220> FEATURE:
<223> OTHER INFORMATION: Synthetic Construct

<400> SEQUENCE: 38
gacatccaga tgacccagtc tccatcctcc ttatctgcct ctgtgggaga tagagtcact    60
atcacttgtc gggcaagtca ggaaattagt ggttacttaa gctggcttca gcagaaacca   120
ggtaagtgtc ctaaacgcct gatctacgcc acatcgactt tacagtctgg tgtcccaagt   180
aggttcagtg gcagtaggtc tgggacagat atactctca ccatcagcag ccttcagcct   240
gaagattttg caacctatta ctgtctacaa tatgctattt atccgctcac gttcggtcag   300
gggaccaagc tggagatcaa acggggtggc ggtggctctg gaggtggtgg gagcggtggc   360
ggcggatctg ggggtggcgg aagccaggtt cagctggtgc agtctgggc agaggttaag   420 aagccagggg cctcagtcaa ggtgtcctgc aaggcttctg gcttcaacat taagacacc   480 tatatgtact gggtgaggca ggcacctgga cagggcctgg agtggatggg aaggattgat   540
cctgcgaatg ataatactaa atatgcccag aagttccagg gcagggtcac tataacagca   600
gacacatcca ccagcacagc ctacatggag ctctccagtc tgagatctga ggacactgcc   660
gtctattact gtgctagagc gaagaatttg ttaaattact ttgactactg gggctgtggc   720
acccttgtca cagtctcctc aggaggcgga gggtctcacc atcaccatca ccat          774

<210> SEQ ID NO 39
<211> LENGTH: 247
<212> TYPE: PRT
<213> ORGANISM: Artificial Sequence
<220> FEATURE:
<223> OTHER INFORMATION: Synthetic Construct

<400> SEQUENCE: 39

Asp Ile Gln Met Thr Gln Ser Pro Ser Leu Ser Ala Ser Val Gly
 1               5                   10                  15

Asp Arg Val Thr Ile Thr Cys Arg Ala Ser Gln Glu Ile Ser Gly Tyr
                 20                  25                  30

Leu Ser Trp Leu Gln Gln Lys Pro Gly Lys Ala Pro Lys Arg Leu Ile
             35                  40                  45

Tyr Ala Thr Ser Thr Leu Gln Ser Gly Val Pro Ser Arg Phe Ser Gly
     50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Leu
                 85                  90                  95

Thr Phe Gly Cys Gly Thr Lys Leu Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Phe Asn Ile Lys Asp Thr
145                 150                 155                 160

Tyr Met Tyr Trp Val Arg Gln Ala Pro Gly Gln Cys Leu Glu Trp Met
                165                 170                 175

Gly Arg Ile Asp Pro Ala Asn Asp Asn Thr Lys Tyr Ala Gln Lys Phe
            180                 185                 190
```

-continued

```
Gln Gly Arg Val Thr Ile Thr Ala Asp Thr Ser Thr Ser Thr Ala Tyr
        195                 200                 205

Met Glu Leu Ser Ser Leu Arg Ser Glu Asp Thr Ala Val Tyr Tyr Cys
    210                 215                 220

Ala Arg Ala Lys Asn Leu Leu Asn Tyr Phe Asp Tyr Trp Gly Gln Gly
225                 230                 235                 240

Thr Leu Val Thr Val Ser Ser
                245
```

```
<210> SEQ ID NO 40
<211> LENGTH: 774
<212> TYPE: DNA
<213> ORGANISM: Artificial Sequence
<220> FEATURE:
<223> OTHER INFORMATION: Synthetic Construct

<400> SEQUENCE: 40
gacatccaga tgacccagtc tccatcctcc ttatctgcct ctgtgggaga tagagtcact      60
atcacttgtc gggcaagtca ggaaattagt ggttacttaa gctggcttca gcagaaacca    120
ggtaaggctc ctaaacgcct gatctacgcc acatcgactt acagtctgg tgtcccaagt    180 aggttcagtg gcagtaggtc tgggacagat tatactctca ccatcagcag ccttcagcct    240
gaagattttg caacctatta ctgtctacaa tatgctattt atccgctcac gttcggttgt    300
gggaccaagc tggagatcaa acggggtggc ggtggctctg gaggtggtgg agcggtggc    360 ggcggatctg ggggtggcgg aagccaggtt cagctggtgc agtctggggc agaggttaag    420
aagccagggg cctcagtcaa ggtgtcctgc aaggcttctg gcttcaacat taaagacacc    480
tatatgtact gggtgaggca ggcacctgga cagtgcctgg agtggatggg aaggattgat    540
cctgcgaatg ataatactaa atatgcccag aagttccagg gcagggtcac tataacagca    600
gacacatcca ccagcacagc ctacatggag ctctccagtc tgagatctga ggacactgcc    660
gtctattact gtgctagagc gaagaatttg ttaaattact ttgactactg gggccaaggc    720
acccttgtca cagtctcctc aggaggcgga gggtctcacc atcaccatca ccat          774
```

```
<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Gly Phe Asn Ile Lys Asp Thr Tyr
1               5
```

```
<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Ile Asp Pro Ala Asn Asp Asn Thr
1               5
```

```
<210> SEQ ID NO 43
<211> LENGTH: 12
<212> TYPE: PRT
<213> ORGANISM: Artificial Sequence
```

```
<220> FEATURE:
<223> OTHER INFORMATION: Synthetic Construct

<400> SEQUENCE: 43

Ala Arg Ala Lys Asn Leu Leu Asn Tyr Phe Asp Tyr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Gln Glu Ile Ser Gly Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: Synthetic Construct

<400> SEQUENCE: 45

Ala Thr Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Leu Gln Tyr Ala Ile Tyr Pro Leu Thr
1               5

<210> SEQ ID NO 47
<211> LENGTH: 20
<212> TYPE: PRT
<213> ORGANISM: Artificial Sequence
<220> FEATURE:
<223> OTHER INFORMATION: Synthetic Construct

<400> SEQUENCE: 47

Gly Gly Gly Gly Ser Gly Gly Gly Ser Gly Gly Gly Ser Gly
1               5                   10                  15

Gly Gly Gly Ser
            20

<210> SEQ ID NO 48
<211> LENGTH: 18
<212> TYPE: PRT
<213> ORGANISM: Artificial Sequence
<220> FEATURE:
<223> OTHER INFORMATION: Synthetic Construct

<400> SEQUENCE: 48

Gly Ser Thr Ser Gly Ser Gly Lys Pro Gly Ser Gly Glu Gly Ser Thr
1               5                   10                  15

Lys Gly
```

```
<210> SEQ ID NO 49
<211> LENGTH: 290
<212> TYPE: PRT
<213> ORGANISM: Artificial Sequence
<220> FEATURE:
<223> OTHER INFORMATION: Synthetic Construct

<400> SEQUENCE: 49

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 50
<211> LENGTH: 30
<212> TYPE: DNA
<213> ORGANISM: Artificial Sequence
<220> FEATURE:
<223> OTHER INFORMATION: Synthetic Construct

<400> SEQUENCE: 50
gacaagaccc acacctgccc tccctgcccc                                         30
```

```
<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Gly Gly Gly Gly Ser His His His His His His
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Asp Thr Tyr Met Tyr
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Gly Phe Asn Ile Lys Asp Thr
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Gly Phe Asn Ile Lys Asp Thr Tyr Met Tyr
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Lys Asp Thr Tyr Met Tyr
1               5

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct

<400> SEQUENCE: 56

Arg Ile Asp Pro Ala Asn Asp Asn Thr Lys Tyr Ala Gln Lys Phe Gln
1               5                   10                  15

Gly
```

<210> SEQ ID NO 57
<211> LENGTH: 6
<212> TYPE: PRT
<213> ORGANISM: Artificial Sequence
<220> FEATURE:
<223> OTHER INFORMATION: Synthetic Construct

<400> SEQUENCE: 57

Asp Pro Ala Asn Asp Asn
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Arg Ile Asp Pro Ala Asn Asp Asn Thr Lys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Construct

<400> SEQUENCE: 59

Trp Met Gly Arg Ile Asp Pro Ala Asn Asp Asn Thr Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Ala Lys Asn Leu Leu Asn Tyr Phe Asp Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Construct

<400> SEQUENCE: 61

Ala Arg Ala Lys Asn Leu Leu Asn Tyr Phe Asp
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Glu Ile Ser Gly Tyr Leu Ser
1               5                   10

```
<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Ser Gly Tyr Leu Ser Trp Leu
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct

<400> SEQUENCE: 64

Ala Thr Ser Thr Leu Gln Ser
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Arg Leu Ile Tyr Ala Thr Ser Thr Leu Gln
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Synthetic Construct

<400> SEQUENCE: 66

Leu Gln Tyr Ala Ile Tyr Pro Leu
1               5
```

COMPOSITIONS AND METHODS FOR IMAGING

CROSS REFERENCE TO RELATED APPLICATIONS

This application is a national stage application under 35 U.S.C. § 371 of International Application No. PCT/CN2019/089571, filed internationally on May 31, 2019, which claims priority benefit to PCT Application No. PCT/CN2018/089672, filed Jun. 1, 2018, which is hereby incorporated by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792572000100SEQLIST.TXT, date recorded: Nov. 30, 2020, size: 64 KB).

FIELD OF THE INVENTION

The present invention relates to antibodies, imaging agents, and methods of imaging an immune checkpoint ligand.

BACKGROUND OF THE INVENTION

The Programmed Death (PD) network involves at least five interacting molecules: PD-1 (Programmed Cell Death 1), two PD-1 ligands (PD-L1 and PD-L2), and two inhibitory receptors (PD-1 and CD80) of PD-L1. The crucial function of the PD pathway in modulating the activity of T cells in the peripheral tissues in an inflammatory response to infection and in limiting autoimmunity appears to be hijacked by tumor cells and by viruses during chronic viral infections. PD-L1 is overexpressed on many freshly isolated human tumors from multiple tissue origins (Dong et al. *Nature Medicine* 2002; 8:793-800; Romano et al. *Journal for Immunotherapy of Cancer* 2015; 3:15; Hirano et al. *Cancer Research* 2005; 65:1089-1096). The expression of PD-L1 has been correlated with the progression and poor prognosis of certain types of human cancers (Wang et al. *European journal of surgical oncology: the journal of the European Society of Surgical Oncology and the British Association of Surgical Oncology* 2015; 41:450-456; Cierna et al. *Annals of oncology: official journal of the European Society for Medical Oncology/ESMO* 2016; 27:300-305; Gandini et al. *Critical reviews in oncology/hematology* 2016; 100:88-98; Thierauf et al. *Melanoma research* 2015; 25:503-509; Taube et al. *Clinical cancer research: an official journal of the American Association for Cancer Research* 2014; 20:5064-5074). During chronic viral infections, PD-L1 is persistently expressed on many tissues, while PD-1 is up-regulated on virus-specific CTLs (Yao et al. *Trends in molecular medicine* 2006; 12:244-246). Tumor- or virus-induced PD-L1 may utilize multiple mechanisms to facilitate the evasion of host immune surveillance, including T cell anergy, apoptosis, exhaustion, IL-10 production, DC suppression, as well as Treg induction and expansion (Zou et al. *Nature reviews Immunology* 2008; 8:467-477).

The PD-L1 expression level determined using immunohistochemistry (IHC) has been assessed as a predictive biomarker in clinical trials of PD-1/PD-L1-directed therapy on multiple cancer types, including melanoma, renal cell carcinoma (RCC), non-small cell lung cancer (NSCLC), metastatic colorectal cancer (mCRC), and metastatic castration-resistant prostate cancer (mCRPC). Patients with higher levels of PD-L1 determined by IHC appeared to have superior responses to PD-1/PD-L1-directed therapy. However, PD-L1-negative patients with melanoma can still obtain durable response to anti-PD-1/PD-L1 therapy, while response rates in PD-L1-negative NSCLC patients are rare.

The accuracy of PD-L1 detection by IHC in human tumor specimens is confounded by multiple factors. A multitude of PD-L1 antibodies for IHC detection have been utilized, including 28-8, 22C3, 5H1, MIH1, and 405.9A11. In addition, a number of proprietary companion diagnostics are being developed in this area, such as Ventana SP142 and Ventana SP263 assay. Comparative performance characteristics of these assays are not well known. In addition to the existing issue of heterogeneous PD-L1 expression within the tumor microenvironment, there's also a lack of a clear definition of "positive" PD-L1 staining by IHC in tumor samples. Cut-off points for a positive result could range from >1% to >50%, based on percent tumor cells stained. Furthermore, PD-L1 has limited binding sites for IHC detection antibodies, as it contains only two small hydrophilic regions, which makes immunohistochemical approaches classically used in formalin-fixed, paraffin-embedded (FFPE) specimens less effective. Due to the lack of binding sites on PD-L1, IHC antibodies typically bind PD-L1 at structurally unique sites compared with therapeutic PD-L1 antibodies.

Additionally, PD-L1 is biologically active only when expressed on the cell membrane, either through dynamic IFNγ expression or through constitutive oncogene activation. Oncogene-driven PD-L1 expression represents a histopathologically and biologically distinct entity compared to inflammation driven PD-L1 expression. While the latter occurs focally at sites of IFNγ-mediated immunologic attack, oncogene-driven PD-L1 expression is constitutive and diffuse. IFNγ induced PD-L1 expression represents a dynamic biomarker and is present at sites of active inflammation, and biopsy samples represent a snapshot of the tumor immune microenvironment in space and time. Other factors in the tumor metabolic microenvironment, including hypoxia, can result in PD-L1 upregulation and are dependent on signaling via HIF1a. Smaller tumor biopsies may miss the pertinent tumor-immune interface, or the biopsy may be performed after the biologically relevant PD-L1 overexpression has already taken place. PD-L1 itself is expressed at two potentially clinically relevant immunologic synapses—the tumor/T-cell interface, as well as the APC/T-cell interface. For the tumor/T-cell interface, biopsy capture of the tumor/immune interface is a key determinant in PD-L1 detection by IHC in melanoma. In a study assessing PD-L1 expression in patients with metastatic melanoma, 96% of PD-L1-overexpressing melanomas had lymphocytic infiltrate (TIL), while the remaining 4% of PD-L1-overexpressing lacked TILs, possibly representing oncogene-driven PD-L1 expression. In addition, 22% of PD-L1 negative samples were associated with TIL, indicating alternative mechanisms of tumor immune interference.

The majority of PD-L1 expression occurs at the tumor interface, with immune cells secreting IFNγ, leading to the counterintuitive hypothesis that PD-L1 overexpression may be an initially protective response to successful tumor killing by TILs, which over time becomes co-opted into an immunosuppressive tumor environment. In addition, selection of the appropriate site for biopsy for PD-L1 detection remains enigmatic. While pretreatment FFPE primary tumor samples may be most readily available, these samples may not reflect the overall immunologic state that currently exists in a given patient, particularly if interim treatment has been administered. The absence of PD-L1 expression in a biopsied lesion may not reflect the systemic immunologic landscape, and may not capture the beneficial effect of the therapy at other sites of the disease that are dependent on PD-L1 signaling. In summary, there is an unmet need for accurate and alternative PD-L1 detection agents and methods.

The disclosures of all publications, patents, patent applications and published patent applications referred to herein are hereby incorporated herein by reference in their entirety.

BRIEF SUMMARY OF THE INVENTION

The present application provides anti-PD-L1 antibodies, imaging agents comprising a labeled antibody moiety that specifically recognizing an immune checkpoint ligand (such as PD-L1 or a PD-L1 like ligand), methods of preparing the imaging agents, and methods of imaging and diagnosis using the imaging agents.

One aspect of the present application provides a method of determining the distribution of an immune checkpoint ligand in an individual, comprising: (a) administering to the individual an imaging agent comprising an antibody moiety labeled with a radionuclide, wherein the antibody fragment specifically binds the immune checkpoint ligand; and (b) imaging the imaging agent in the individual with a non-invasive imaging technique. In some embodiments, the method further comprises determining the expression level of the immune checkpoint ligand in a tissue of interest in the individual based on signals emitted by the imaging agent from the tissue. In some embodiments, the method comprises determining the distribution of two or more immune checkpoint ligands in the individual.

In some embodiments according to any one of the methods described above, the imaging agent is cleared from the individual within about 10 minutes to about 48 hours (e.g., about 2 hours to about 4 hours, about 4 hours to about 8 hours, or about 8 hours to about 24 hours) in serum. In some embodiments, the half-life of the antibody moiety is between about 10 minutes to about 24 hours (e.g., about 1 hour to about 2 hours, about 2 hours to about 4 hours, about 4 hours to about 12 hours, or about 12 hours to about 24 hours).

In some embodiments according to any one of the methods described above, the molecular weight of the antibody moiety is no more than about 120 kDa (e.g., about any one of 30-50 kDa, 50-100 kDa, or 30-80 kDa).

In some embodiments according to any one of the methods described above, the antibody moiety has a $K_D$ between about $9\times10^{-10}$ M to about $1\times10^{-8}$ M (e.g., about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand.

In some embodiments according to any one of the methods described above, the antibody moiety cross-reacts with the immune checkpoint ligand from a non-human mammal. In some embodiments, the antibody moiety cross-reacts with the immune checkpoint ligand from a cynomolgus monkey. In some embodiments, the antibody moiety cross-reacts with the immune checkpoint ligand from a mouse.

In some embodiments according to any one of the methods described above, the antibody moiety is humanized. In some embodiments, the antibody moiety is human. In some embodiments, the antibody moiety is chimeric.

In some embodiments according to any one of the methods described above, the antibody moiety is stable at acidic or neutral pH. In some embodiments, the antibody moiety has a melting temperature of about 55-70° C. (e.g., about 55-60° C., about 60-65° C., or about 65-70° C.).

In some embodiments according to any one of the methods described above, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H. In some embodiments, the antibody moiety is an scFv. In some embodiments, the scFv comprises one or more engineered disulfide bonds. In some embodiments, the scFv comprises a first engineered cysteine residue at position 44 of V$_H$ and a second engineered cysteine residue at position 100 of V$_L$, or a first engineered cysteine residue at position 105 of V$_H$ and a second engineered cysteine residue at position 43 of V$_L$, wherein the first engineered cysteine residue and the second engineered cysteine residue form a disulfide bond, and wherein the amino acid positions are based on the Kabat numbering system. In some embodiments, the antibody moiety is an scFv fused to an Fc fragment. In some embodiments, the Fc fragment is a human IgG1 Fc fragment. In some embodiments, the Fc fragment has H310A and H435Q mutations, wherein the amino acid positions are based on the Kabat numbering system. In some embodiments, the scFv comprises from the N-terminus to the C-terminus: a heavy chain variable region (V$_H$), an optional peptide linker, and a light chain variable region (V$_L$). In some embodiments, the scFv comprises from the N-terminus to the C-terminus: a V$_L$, an optional peptide linker, and a V$_H$. In some embodiments, the scFv comprises a peptide linker comprising the amino acid sequence of SEQ ID NO: 47 or 48.

In some embodiments according to any one of the methods described above, the immune checkpoint ligand is PD-L1 or a PD-L1 like ligand. In some embodiments, the immune checkpoint ligand is PD-L1. In some embodiments, the antibody moiety comprises: a V$_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a V$_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46; or the antibody moiety specifically binds PD-L1 competitively with an anti-PD-L1 antibody comprising: a V$_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a V$_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46.

In some embodiments according to any one of the methods described above, the tissue of interest is negative for the immune checkpoint ligand based on an immunohistochemistry (IHC) assay or another assay. In some embodiments, the tissue of interest has a low expression level of the immune checkpoint ligand. In some embodiments, the tissue of interest only expresses the immune checkpoint ligand upon infiltration of immune cells.

In some embodiments according to any one of the methods described above, the method comprises imaging the individual over a period of time.

In some embodiments according to any one of the methods described above, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the antibody moiety is conjugated to a chelating compound that chelates the radionuclide. In some embodiments, the chelating compound is 1,4,7-triazacyclononane-1,4,7-trisacetic acid (NOTA), 1,4,7,10-tetraazacyclododecane-1,4,7,10-tetraacetic acid (DOTA) or derivatives thereof. In some embodiments, the chelating compound is NOTA.

In some embodiments according to any one of the methods described above, the method further comprises preparing the imaging agent by labeling the antibody moiety with the radionuclide.

In some embodiments according to any one of the methods described above, the non-invasive imaging technique comprises single photon emission computed tomography (SPECT) imaging or positron emission tomography (PET) imaging. In some embodiments, the non-invasive imaging technique comprises computed tomography imaging, magnetic resonance imaging, chemical luminescence imaging, or electrochemical luminescence imaging.

In some embodiments according to any one of the methods described above, the imaging agent is administered intravenously, intraperitoneally, intramuscularly, subcutaneously, or orally.

In some embodiments according to any one of the methods described above, the imaging is carried out between about 10 minutes to about 24 hours (e.g., about 10 minutes to 1 hour, about 1 hour to 2 hours, about 2 hours to 4 hours, about 4 hours to 8 hours, or about 8 hours to 24 hours) after the administration of the imaging agent.

In some embodiments according to any one of the methods described above, the method further comprises administering to the individual an antibody moiety not labeled with a radionuclide prior to the administration of the imaging agent.

In some embodiments according to any one of the methods described above, the individual has a solid tumor. In some embodiments, the solid tumor is selected from the group consisting of colon tumor, melanoma, kidney tumor, ovarian tumor, lung tumor, breast tumor, and pancreatic tumor. In some embodiments, the individual has a hematological malignancy. In some embodiments, the hematological malignancy is selected from the group consisting of leukemia, lymphoma, acute lymphoblastic leukemia (ALL), acute non-lymphoblastic leukemia (ANLL), chronic lymphocytic leukemia (CLL), chronic myeloid leukemia (CML), non-Hodgkin lymphoma, and Hodgkin lymphoma. In some embodiments, the individual has an infectious disease, autoimmune disease, or metabolic disease.

One aspect of the present application provides a method of diagnosing an individual having a disease or condition, comprising: (a) determining the distribution of an immune checkpoint ligand in the individual using the method according to any one of the methods described above; and (b) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest.

One aspect of the present application provides a method of treating an individual having a disease or condition, comprising: (a) diagnosing the individual using the method according to any one of the methods of diagnosis described above; and (b) administering to the individual an effective amount of a therapeutic agent targeting the immune checkpoint ligand or receptor thereof, if the individual is diagnosed as positive for the immune checkpoint ligand. In some embodiments, the therapeutic agent is an inhibitor of the immune checkpoint ligand or receptor thereof. In some embodiments, the therapeutic agent is a radiolabeled molecule specifically binding the immune checkpoint ligand or receptor thereof. In some embodiments, wherein the immune checkpoint ligand is PD-L1, the individual is administered with an antibody specifically binding PD-1 or PD-L1. In some embodiments, the immune checkpoint ligand is a PD-L1 like ligand.

Another aspect of the present application provides an isolated anti-PD-L1 antibody agent comprising an antibody moiety comprising a heavy chain variable region ($V_H$) comprising a heavy chain complementarity determining region (HC-CDR)1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 (e.g., 1, 2, 3, 4, or 5) amino acid substitutions; and a light chain variable region ($V_L$) comprising a light chain complementarity determining region (LC-CDR)1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 (e.g., 1, 2, 3, 4, or 5) amino acid substitutions. In some embodiments, the antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46.

In some embodiments, there is provided an isolated anti-PD-L1 antibody agent comprising an antibody moiety comprising a $V_H$ comprising a HC-CDR1, a HC-CDR2, and a HC-CDR3 of SEQ ID NO: 1; and a $V_L$ comprising a LC-CDR1, a LC-CDR2, and a LC-CDR3 of SEQ ID NO: 3. In some embodiments, the antibody moiety comprises: a $V_H$ comprising an amino acid sequence having at least about 80% (e.g., at least about any one of 80%, 85%, 90%, 95%, 98%, 99% or higher) sequence identity to the amino acid sequence of any one of SEQ ID NOs: 1, 5, 9, 11, and 13; and a $V_L$ comprising an amino acid sequence having at least about 80% (e.g., at least about any one of 80%, 85%, 90%, 95%, 98%, 99% or higher) sequence identity to the amino acid sequence of any one of SEQ ID NOs: 3, 7, 15, 17 and 19. In some embodiments, the antibody moiety comprises: (a) a $V_H$ comprising the amino acid sequence of SEQ ID NO: 9, and a $V_L$ comprising the amino acid sequence of SEQ ID NO: 15; (b) a $V_H$ comprising the amino acid sequence of SEQ ID NO: 9, and a $V_L$ comprising the amino acid sequence of SEQ ID NO: 17; (c) a $V_H$ comprising the amino acid sequence of SEQ ID NO: 9, and a $V_L$ comprising the amino acid sequence of SEQ ID NO: 19; (d) a $V_H$ comprising the amino acid sequence of SEQ ID NO: 11, and a $V_L$ comprising the amino acid sequence of SEQ ID NO: 15; (e) a $V_H$ comprising the amino acid sequence of SEQ ID NO: 11, and a $V_L$ comprising the amino acid sequence of SEQ ID NO: 17; (f) a $V_H$ comprising the amino acid sequence of SEQ ID NO: 11, and a $V_L$ comprising the amino acid sequence of SEQ ID NO: 19; (g) a $V_H$ comprising the amino acid sequence of SEQ ID NO: 13, and a $V_L$ comprising the amino acid sequence of SEQ ID NO: 15; (h) a $V_H$ comprising the amino acid sequence of SEQ ID NO: 13, and a $V_L$ comprising the amino acid sequence of SEQ ID NO: 17; or (i) a $V_H$ comprising the amino acid sequence of SEQ ID NO: 13, and a $V_L$ comprising the amino acid sequence of SEQ ID NO: 19.

In some embodiments according to any one of the isolated anti-PD-L1 antibody agents described above, the antibody moiety is humanized. In some embodiments, the antibody moiety is human. In some embodiments, the antibody moiety is chimeric.

In some embodiments according to any one of the isolated anti-PD-L1 antibody agents described above, the antibody moiety comprises an scFv. In some embodiments, the scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the scFv comprises an amino acid sequence having at least about 80% (e.g., at least about any one of 80%, 85%, 90%, 95%, 98%, 99% or higher) sequence identity to the amino acid sequence of any one of SEQ ID NOs: 25, 27, 29, 31, 33, 35, 37 and 39. In some embodiments, the scFv comprises the amino acid sequence of any one of SEQ ID NOs: 25, 27, 29, 31, 33, 35, 37 and 39. In some embodiments, the antibody moiety is an scFv. In some embodiments, the antibody moiety is an scFv fused to an Fc fragment. In some embodiments, the Fc fragment is a human IgG1 Fc fragment. In some embodiments, the Fc fragment has H310A and H435Q mutations, wherein the amino acid positions are based on the Kabat numbering system.

In some embodiments, there is provided an anti-PD-L1 antibody agent comprising an antibody moiety that specifically binds PD-L1 competitively with the antibody moiety in the anti-PD-L1 antibody agent according to any one of the isolated anti-PD-L1 antibody agents described above.

Another aspect of the present application provides an imaging agent comprising an antibody moiety labeled with a radionuclide, wherein the antibody moiety specifically binds an immune checkpoint ligand. In some embodiments, the immune checkpoint ligand is PD-L1 or a PD-L1 like ligand. In some embodiments, there is provided an imaging agent comprising the isolated anti-PD-L1 antibody agent of according to any one of the isolated anti-PD-L1 antibody agents described herein, wherein the antibody moiety is labeled with a radionuclide.

In some embodiments according to any one of the imaging agents described herein, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the antibody moiety is conjugated to a chelating compound that chelates the radionuclide. In some embodiments, the chelating compound is NOTA, DOTA, or derivatives thereof. In some embodiments, the chelating compound is NOTA.

Also provided is an isolated nucleic acid encoding the isolated anti-PD-L1 antibody agent according to any one of the isolated anti-PD-L1 antibody agents described herein, a vector comprising the isolated nucleic acid, and an isolated host cell comprising the isolated anti-PD-L1 antibody agent, the isolated nucleic acid, or the vector.

Another aspect of the present application provides a method of preparing an imaging agent targeting an immune checkpoint ligand, comprising: (a) conjugating a chelating compound to an antibody moiety specifically binding the immune checkpoint ligand to provide an antibody moiety conjugate; (b) contacting a radionuclide with the antibody moiety conjugate, thereby providing the imaging agent. In some embodiments, the immune checkpoint ligand is PD-L1 or a PD-L1 like ligand.

In some embodiments, there is provided a method of preparing an imaging agent targeting PD-L1, comprising: (a) conjugating a chelating compound to the antibody moiety in the isolated anti-PD-L1 antibody agent according to any one of the isolated anti-PD-L1 antibody agents described above to provide an anti-PD-L1 conjugate; and (b) contacting a radionuclide with the anti-PD-L1 antibody conjugate, thereby providing the imaging agent.

In some embodiments according to any one of the methods of preparation described herein, the chelating compound is conjugated to a lysine of the antibody moiety.

Further provided is a kit comprising (a) an antibody moiety specifically binding an immune checkpoint ligand; and (b) a chelating compound. In some embodiments, the kit further comprises a radionuclide.

In some embodiments, there is provided a kit comprising: (a) an imaging agent comprising an antibody moiety labeled with a radionuclide, wherein the antibody moiety specifically binds an immune checkpoint ligand; and (b) an antibody moiety not labeled with a radionuclide.

Also provided are compositions, kits and articles of manufacture comprising the any one of the anti-PD-L1 antibody agents and imaging agents described herein.

BRIEF DESCRIPTION OF THE DRAWINGS

FIG. 1A shows histograms demonstrating the binding affinity of anti hPD-L1 monoclonal antibody 5B7 to hPD-L1 protein at different concentrations. FIG. 1B shows the mean fluorescence intensity at the respective concentrations.

FIG. 8A shows serum titers of anti-hPD-L1 antibodies. FIG. 8B shows serum titers of hIgG.

DETAILED DESCRIPTION OF THE INVENTION

Figure 1A:
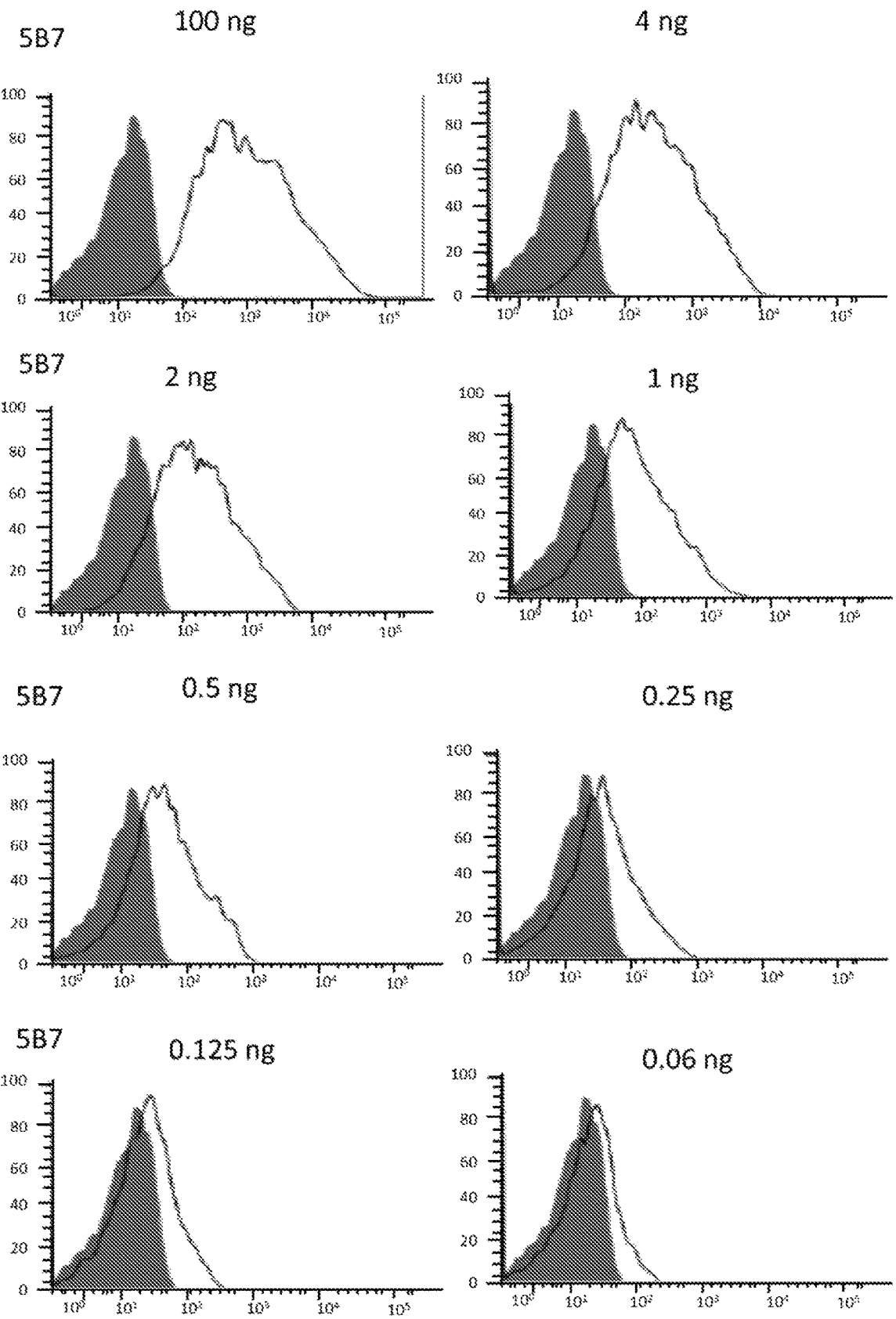
FIGS. 1A and 1B show the binding affinity of anti hPD-L1 monoclonal antibody 5B7 to hPD-L1 protein.

The present application provides imaging agents and methods for detection of an immune checkpoint ligand in an individual. The imaging agents described herein comprise an antibody moiety labeled with a radionuclide, wherein the antibody moiety specifically binds the immune checkpoint ligand, such as PD-L1 or a PD-L1 like ligand. The antibody moiety (such as Fab, scFv or scFv fused to an Fc) is characterized by a small size and rapid clearance from blood and normal organs. In some embodiments, the antibody moiety is engineered to have enhanced thermal stability. Imaging agents comprising such antibody moieties labeled with short-lived radionuclides allow effective targeting and penetration of diseased tissues expressing the immune checkpoint ligand. Distribution and expression levels of the immune checkpoint ligand can be determined by in vivo imaging of an individual administered with the imaging agent. Prior to the present invention, accurate diagnosis based on PD-L1 and other immune checkpoint ligands as biomarkers remain a challenge in the field of cancer immunotherapy.

Accordingly, one aspect of the present application provides a method of determining the distribution of an immune checkpoint ligand (such as PD-L1 or a PD-L1 like ligand) in an individual, comprising: (a) administering to the individual an imaging agent comprising an antibody moiety labeled with a radionuclide, wherein the antibody moiety specifically binds the immune checkpoint ligand; and (b) imaging the imaging agent in the individual with a non-invasive imaging technique.

Another aspect of the present application provides an imaging agent comprising an antibody moiety labeled with a radionuclide, wherein the antibody moiety specifically binds an immune checkpoint ligand (such as PD-L1 or a PD-L1 like ligand).

Another aspect of the presentation provides an anti-PD-L1 antibody agent comprising: a $V_H$ comprising a HC-CDR1, a HC-CDR2, and a HC-CDR3 of SEQ ID NO: 1; and a $V_L$ comprising a LC-CDR1, a LC-CDR2, and a LC-CDR3 of SEQ ID NO: 3.

Also provided are compositions, kits and articles of manufacture comprising the imaging agents and anti-PD-L1 antibody agents described herein, methods of making thereof, and methods of diagnosing or treating an individual having a disease or condition (such as cancer, infectious disease, autoimmune disease or metabolic disease).

I. Definitions

As used herein, "immune system checkpoints," or "immune checkpoints" refer to inhibitory pathways in the immune system that generally act to maintain self-tolerance or modulate the duration and amplitude of physiological immune responses to minimize collateral tissue damage. Stimulatory checkpoint molecules are molecules, such as proteins, that stimulate or positively regulate the immune system. Inhibitory checkpoint molecules are molecules, such as proteins, that inhibit or negatively regulate the immune system. Immune system checkpoint molecules include, but are not limited to, cytotoxic T-lymphocyte antigen 4 (CTLA-4), programmed cell death 1 protein (PD-1), PD-L1, PD-L2, lymphocyte activation gene 3 (LAG3), B7-1, B7-H3, B7-H4, T cell membrane protein 3 (TIM3), B- and T-lymphocyte attenuator (BTLA), V-domain immunoglobulin (Ig)-containing suppressor of T-cell activation (VISTA), Killer-cell immunoglobulin-like receptor (KIR), and A2A adenosine receptor (A2aR).

"Immune checkpoint receptors" are immune checkpoint molecules that are expressed on immune cells, such as T cells.

As used herein, the term "immune checkpoint ligand" refers to a naturally-occurring or non-naturally occurring ligand that is specifically recognized by an immune checkpoint receptor. Naturally occurring immune checkpoint ligands are immune checkpoint molecules that may be expressed by diseased tissue, such as tumor cells, infected cells, or inflamed tissue, which can regulate immune cells that express immune checkpoint receptors that specifically recognize the immune checkpoint ligands. Non-naturally occurring immune checkpoint ligands include synthetic and recombinant molecules, such as therapeutic inhibitors, ligands, and antibodies of immune checkpoint receptors. Non-naturally occurring immune checkpoint ligands may be introduced to the individual, e.g., by administration to the individual. An immune checkpoint ligand can inhibit an immune checkpoint by stimulating the activity of a stimulatory checkpoint receptor, or inhibiting the activity of an inhibitory checkpoint receptor in the pathway. Exemplary naturally-occurring immune checkpoint ligands include, but are not limited to, PD-L1, PD-L2, B7-H3 (also known as CD276), galectin-9, CD80, CD86 and ICOSL. In some embodiments, the immune checkpoint ligand is PD-L1. In some embodiments, the immune checkpoint ligand is a PD-L1 like ligand. "PD-L1 like ligand" refers to a naturally occurring or non-naturally occurring ligand of PD-1.

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody moiety" refers to a full-length antibody or an antigen-binding fragment thereof.

A full-length antibody comprises two heavy chains and two light chains. The variable regions of the light and heavy chains are responsible for antigen binding. The variable domains of the heavy chain and light chain may be referred to as "$V_H$" and "$V_L$", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as lgG1 (γ1 heavy chain), lgG2 (γ2 heavy chain), lgG3 (γ3 heavy chain), lgG4 (γ4 heavy chain), lgA1 (α1 heavy chain), or lgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.*, 273: 927-948 (1997); MacCallum et al., J. Mol. Biol. 262:732-745 (1996); Abhinandan and Martin, *Mol. Immunol.*, 45: 3832-3839 (2008); Lefranc M. P. et al., *Dev. Comp. Immunol.*, 27: 55-77 (2003); and Honegger and Plückthun, *J. Mol. Biol.*, 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.*, 45: 3832-3839 (2008); Ehrenmann F. et al., *Nucleic Acids Res.*, 38: D301-D307 (2010); and Adolf-Bryfogle J. et al., *Nucleic Acids Res.*, 43: D432-D438 (2015). *The contents of the references* cited in this paragraph are incorporated herein by reference in their entireties for use in the present invention and for possible inclusion in one or more claims herein.

TABLE 1

CDR DEFINITIONS

|  | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the CDR residues as herein defined.

The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32(5):1792-1797, 2004; Edgar, R. C., BMC Bioinformatics 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody moiety "competes" for binding to a target antigen with a second antibody moiety when the first antibody moiety inhibits the target antigen binding of the second antibody moiety by at least about 50% (such as at least about any one of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

An "isolated" antibody (or construct) is one that has been identified, separated and/or recovered from a component of its production environment (e.g., natural or recombinant). Preferably, the isolated polypeptide is free of association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

The term "effective amount" refers to the amount of an agent that is sufficient to effect beneficial or desired results. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The terms "subject," "individual," and "patient" are used interchangeably herein to refer to a mammal, including, but not limited to, human, bovine, horse, feline, canine, rodent, or primate. In some embodiments, the individual is a human.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Methods of Imaging

One aspect of the present application provides a method of determining the distribution and/or expression level of an immune checkpoint ligand in an individual using an imaging agent comprising an antibody moiety labeled with a radionuclide, wherein the antibody moiety specifically binds the immune checkpoint ligand. In some embodiments, the method comprises determination of the distribution and/or expression level of two or more immune checkpoint ligands in the individual.

In some embodiments, there is provided a method of determining the distribution of an immune checkpoint ligand in an individual, comprising: (a) administering to the individual an imaging agent comprising an antibody moiety labeled with a radionuclide, wherein the antibody fragment specifically binds the immune checkpoint ligand; and (b) imaging the imaging agent in the individual with a non-invasive imaging technique. In some embodiments, the method further comprises determining the expression level of the immune checkpoint ligand in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the antibody moiety is conjugated to a chelating compound that chelates the radionuclide. In some embodiments, the chelating compound is 1,4,7-triazacyclononane-1,4,7-trisacetic acid (NOTA), 1,4,7,10-tetraazacyclododecane-1,4,7,10-tetraacetic acid (DOTA) or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H.

In some embodiments, there is provided a method of determining the distribution of an immune checkpoint ligand in an individual, comprising: (a) administering to the individual an imaging agent comprising an scFv labeled with a radionuclide, wherein the scFv specifically binds the immune checkpoint ligand; and (b) imaging the imaging agent in the individual with a non-invasive imaging technique. In some embodiments, the method further comprises determining the expression level of the immune checkpoint ligand in a tissue of interest in the individual based on signals emitted by the imaging agent from the tissue. In some embodiments, the method further comprises preparing the imaging agent by labeling the scFv with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual the scFv not labeled with a radioisotope prior to the administration of the imaging agent. In some embodiments, the method comprises imaging the individual over a period of time. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the scFv is conjugated to a chelating compound that chelates the radionuclide. In some embodiments, the chelating compound is NOTA, DOTA or derivatives thereof. In some embodiments, the scFv has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the scFv cross-reacts with the immune checkpoint ligand from a non-human mammal (e.g., mouse, rat or monkey). In some embodiments, the scFv is humanized. In some embodiments, the scFv is stable at acidic pH (e.g., at a pH lower than about 6.5, 6.0, 5.5, or 5.0). In some embodiments, the scFv has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a V$_H$, an optional peptide linker, and a V$_L$. In some embodiments, the scFv comprises from the N-terminus to the C-terminus: a V$_L$, an optional peptide linker, and a V$_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

In some embodiments, there is provided a method of determining the distribution of an immune checkpoint ligand in an individual, comprising: (a) administering to the individual an imaging agent comprising an antibody moiety labeled with a radionuclide, wherein the antibody moiety is an scFv fused to an Fc fragment, wherein the antibody fragment specifically binds the immune checkpoint ligand; and (b) imaging the imaging agent in the individual with a non-invasive imaging technique. In some embodiments, the method further comprises determining the expression level of the immune checkpoint ligand in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ca$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the antibody moiety is conjugated to a chelating compound that chelates the radionuclide. In some embodiments, the chelating compound is NOTA, DOTA or derivatives thereof. In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a $V_H$, an optional peptide linker, and a $V_L$.

In some embodiments, the scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is a human IgG1 Fc fragment. In some embodiments, the Fc fragment has H310A and H435Q mutations, wherein the amino acid positions are based on the Kabat numbering system.

In some embodiments, there is provided a method of determining the distribution of PD-L1 in an individual, comprising: (a) administering to the individual an imaging agent comprising an antibody moiety (e.g., an scFv) labeled with a radionuclide, wherein the antibody fragment specifically binds PD-L1; and (b) imaging the imaging agent in the individual with a non-invasive imaging technique. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the anti-PD-L1 antibody moiety is conjugated to a chelating compound that chelates the radionuclide. In some embodiments, the chelating compound is NOTA, DOTA or derivatives thereof. In some embodiments, the anti-PD-L1 antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the anti-PD-L1 antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the anti-PD-L1 antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about 5×10⁻¹⁰ to 1×10⁻⁸) with the immune checkpoint ligand. In some embodiments, the anti-PD-L1 antibody moiety cross-reacts with the immune checkpoint ligand from a non-human mammal (e.g., mouse, rat or monkey). In some embodiments, the anti-PD-L1 antibody moiety is humanized. In some embodiments, the anti-PD-L1 antibody moiety is stable at acidic pH (e.g., at a pH lower than about 6.5, 6.0, 5.5, or 5.0). In some embodiments, the anti-PD-L1 antibody moiety has a melting temperature (Tm) of about 55-70° C. (such as about any one of 55-60, 60-65, or 65-70° C.). In some embodiments, the anti-PD-L1 antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H. In some embodiments, the anti-PD-L1 antibody moiety is an scFv. In some embodiments, the anti-PD-L1 antibody moiety is an scFv fused to an Fc.

In some embodiments, there is provided a method of determining the distribution of a PD-L1 like ligand in an individual, comprising: (a) administering to the individual an imaging agent comprising an antibody moiety (e.g., an scFv) labeled with a radionuclide, wherein the antibody fragment specifically binds the PD-L1 like ligand; and (b) imaging the imaging agent in the individual with a non-invasive imaging technique. In some embodiments, the PD-L1 like ligand is a naturally occurring ligand of PD-1. In some embodiments, the PD-L1 like ligand is a non-naturally occurring ligand of PD-1, and wherein the PD-L1 like ligand has been administered to the individual. In some embodiments, the method further comprises determining the expression level of the PD-L1 like ligand in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the antibody moiety is conjugated to a chelating compound that chelates the radionuclide. In some embodiments, the chelating compound is NOTA, DOTA or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a K$_D$ between about 9×10⁻¹⁰ M to about 1×10⁻⁸ M (such as about 9×10⁻¹⁰ to 1×10⁻⁹, about 1×10⁻⁹ to 2×10⁻⁹, about 2×10⁻¹⁰ to 5×10⁻⁹, or about 5×10⁻¹⁰ to 1×10⁻⁸) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the anti-antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H. In some embodiments, the antibody moiety is an scFv. In some embodiments, the anti-PD-L1 antibody moiety is an scFv fused to an Fc.

In some embodiments, there is provided a method of determining the distribution of PD-L1 in an individual, comprising: (a) administering to the individual an imaging agent comprising an anti-PD-L1 antibody moiety labeled with a radionuclide; and (b) imaging the imaging agent in the individual with a non-invasive imaging technique, wherein the anti-PD-L1 antibody moiety comprises: a V$_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a V$_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the anti-PD-L1 antibody moiety comprises: a V$_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a V$_L$ comprising the amino acid sequence of any one of SEQ ID NOs: 3, 7, 15, 17 and 19, or a variant thereof having at least about 80%

(such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided a method of determining the distribution of PD-L1 in an individual, comprising: (a) administering to the individual an imaging agent comprising an anti-PD-L1 scFv labeled with a radionuclide; and (b) imaging the imaging agent in the individual with a non-invasive imaging technique, wherein the anti-PD-L1 scFv comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the anti-PD-L1 scFv comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 scFv is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided a method of determining the distribution of PD-L1 in an individual, comprising: (a) administering to the individual an imaging agent comprising an anti-PD-L1 antibody moiety labeled with a radionuclide; and (b) imaging the imaging agent in the individual with a non-invasive imaging technique, wherein the anti-PD-L1 antibody moiety comprises an anti-PD-L1 scFv fused to an Fc fragment, and wherein the anti-PD-L1 scFv comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the anti-PD-L1 antibody moiety is conjugated to a chelating compound that chelates the radionuclide. In some embodiments, the chelating compound is NOTA, DOTA or derivatives thereof.

The methods described herein can be used to determine the distribution of an immune checkpoint ligand (e.g., PD-L1 or PD-L1 like ligands) in an individual or a tissue of interest in an individual. The method may also provide qualitative or quantitative information on the expression level of the immune checkpoint ligand in one or more tissues or organ of an individual. Additionally, the methods described herein can allow imaging of an individual over a period of time, for example, by providing a plurality of sets of imaging results at different time points after the administration of the imaging agent to the individual. In some embodiments, the imaging is carried out for at least 2, 3, 4, 5, 6, 7, 8, 9, 10 or more times over a period between about 10 minutes to about 24 hours (such as about any one of 10 minutes to 1 hour, 1 hour to 2 hours, 2 hours to 4 hours, 4 hours to 8 hours, 8 hours to 12 hours, 12 hours to 24 hours, 1 hour to 4 hours or 1 hour to 8 hours). In some embodiments, the imaging is carried out between about 10 minutes to about 24 hours after the administration of the imaging agent, for example, between about any one of 10 minutes to 1 hour, 1 hour to 2 hours, 2 hours to 4 hours, 4 hours to 8 hours, 8 hours to 12 hours, 12 hours to 24 hours, 1 hour to 4 hours or 1 hour to 8 hours.

Methods of imaging using labeled polypeptides are well known in the art, and any such known methods may be used with the imaging agents disclosed herein. See, for example, Srivastava (ed.), Radiolabeled Monoclonal Antibodies for Imaging and Therapy (Plenum Press 1988), Chase, "Medical Applications of Radioisotopes," in Remington's Pharmaceutical Sciences, 18th Edition, Gennaro et al. (eds.), pp. 624-652 (Mack Publishing Co., 1990), and Brown, "Clinical Use of Monoclonal Antibodies," in Biotechnology and Pharmacy 227-49, Pezzuto et al. (eds.) (Chapman & Hall 1993).

In some embodiments, the non-invasive imaging technique uses positron-emitting radionuclides (PET isotopes), such as with an energy of about 511 keV, such as $^{18}F$, $^{68}Ga$, $^{64}Cu$, and $^{124}I$. Such radionuclides may be imaged by well-known PET scanning techniques. See, also, U.S. Pat. Nos. 6,953,567; 9,884,131 and international patent application publication No. WO2016149188A1, and Kim H Y. et al., (2018) PLoS ONE 13(3): e0192821, which are incorporated herein by reference.

In some embodiments, the non-invasive imaging technique comprises single photon emission computed tomography (SPECT) imaging. In some embodiments, the non-invasive imaging technique comprises positron emission tomography (PET) imaging. In some embodiments, SPEC or PET imaging is combined with one or more other non-invasive imaging method, which may or may not be based on the signals from the imaging agent. For example, PET may be combined with computed tomography (CT) imaging, magnetic resonance imaging (MRI), chemical luminescence imaging, or electrochemical luminescence imaging.

The imaging methods described herein are suitable for detecting immune checkpoint ligands at low, moderate, or high expression levels. In some embodiments, the imaging method provides dynamic information on the expression level and distribution of the immune checkpoint ligand. In some embodiments, the imaging method is capable of detecting the immune checkpoint ligand in situations that might be challenging for other methods of detection, such as immunohistochemistry (IHC). For example, in some embodiments, the tissue of interest is negative for the immune checkpoint ligand based on an immunohistochemistry (IHC) assay or another assay. Molecular assays that may be used for detecting the presence or absence of an immune checkpoint ligand include, but are not limited to, polymerase chain reaction (PCR)-based assays, next-generation sequencing (NGS) assays, hybridization assays, and ELISA. In some embodiments, the tissue of interest has a low expression level of the immune checkpoint ligand. In some embodiments, the tissue of interest only expresses the immune checkpoint ligand upon infiltration of immune cells.

The imaging agent may be administered to the individual using any suitable dosage and routes of administration. The route of administration is in accordance with known and accepted methods, such as by single or multiple bolus or infusion over a period of time in a suitable manner, e.g., injection or infusion by subcutaneous, intravenous, intraperitoneal, intramuscular, intra-arterial, intralesional, intraarticular, intratumoral, or oral routes. The determination of the appropriate dosage or route of administration is well within the skill of an ordinary artisan. Animal experiments provide reliable guidance for the determination of effective doses for human diagnostic applications. Interspecies scaling of effective doses can be performed following the principles laid down by Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

Diagnosis and Treatment

The methods described herein are useful for diagnosis and as a companion diagnostic method for treatment of a variety of diseases and conditions that are associated with abnormal immune response. In some embodiments, the disease or condition is associated with immune deficiency. In some embodiments, the disease or condition is cancer, infectious disease, autoimmune disease, or a metabolic disease.

In some embodiments, there is provided a method of diagnosing an individual having a disease or condition, comprising: (a) determining the distribution of an immune checkpoint ligand in the individual using any one of the methods for determining distribution of an immune checkpoint ligand described herein; and (b) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest. In some embodiments, the disease or condition is cancer, infection, autoimmune disease, or metabolic disease. In some embodiments, the immune checkpoint ligand is PD-L1. In some embodiments, the immune checkpoint ligand is a PD-L1 like ligand.

In some embodiments, there is provided a method of diagnosing an individual having a disease or condition, comprising: (a) administering to the individual an imaging agent comprising an antibody moiety labeled with a radionuclide, wherein the antibody fragment specifically binds the immune checkpoint ligand; (b) imaging the imaging agent in the individual with a non-invasive imaging technique; and (c) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest. In some embodiments, the method further comprises determining the expression level of the immune checkpoint ligand in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the immune checkpoint ligand is selected from the group consisting of PD-L1, PD-L2, B7-H3, galectin-9, CD80, CD86 and ICOSL. In some embodiments, the radionuclide is selected from the group consisting of $^{664}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the antibody moiety is conjugated to a chelating compound that chelates the radionuclide. In some embodiments, the chelating compound is NOTA, DOTA or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9 \times 10^{-10}$ M to about $1 \times 10^{-8}$ M (such as about $9 \times 10^{-10}$ to $1 \times 10^{-9}$, about $1 \times 10^{-9}$ to $2 \times 10^{-9}$, about $2 \times 10^{-10}$ to $5 \times 10^{-9}$, or about $5 \times 10^{-10}$ to $1 \times 10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a $V_H H$. In some embodiments, the disease or condition is cancer, infection, autoimmune disease, or metabolic disease. In some embodiments, the immune checkpoint ligand is PD-L1. In some embodiments, the immune checkpoint ligand is a PD-L1 like ligand. In some embodiments, the antibody moiety is an scFv. In some embodiments, the antibody moiety is an scFv fused to an Fc fragment (such as a human IgG1 Fc).

In some embodiments, there is provided a method of diagnosing an individual having a disease or condition, comprising: (a) administering to the individual an imaging agent comprising an anti-PD-L1 antibody moiety labeled with a radionuclide; (b) imaging the imaging agent in the individual with a non-invasive imaging technique; and (c) diagnosing the individual as positive for PD-L1 if signal of the imaging agent is detected at a tissue of interest, or diagnosing the individual as negative for the immune checkpoint ligand if signal of the imaging agent is not detected at a tissue of interest; wherein the anti-PD-L1 antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the anti-PD-L1 antibody moiety is conjugated to a chelating compound that chelates the radionuclide. In some embodiments, the chelating compound is NOTA, DOTA or derivatives thereof. In some embodiments, the disease or condition is cancer, infection, autoimmune disease, or metabolic disease. In some embodiments, the antibody moiety is an scFv. In some embodiments, the antibody moiety is an scFv fused to an Fc fragment (such as a human IgG1 Fc). In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the anti-PD-L1 antibody moiety comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39.

In some embodiments, there is provided a method of treating an individual having a disease or condition, comprising: (a) diagnosing the individual using any method of diagnosis described herein; and (b) administering to the individual an effective amount of a therapeutic agent targeting the immune checkpoint ligand or receptor thereof, if the individual is diagnosed as positive for the immune checkpoint ligand. In some embodiments, the therapeutic agent is an inhibitor of the immune checkpoint ligand or receptor thereof. In some embodiments, the therapeutic agent is a radiolabeled molecule specifically binding the immune checkpoint ligand or receptor thereof. In some embodiments, the disease or condition is cancer, infection, autoimmune disease, or metabolic disease. In some embodiments, the immune checkpoint ligand is PD-L1. In some embodiments, the immune checkpoint ligand is a PD-L1 like ligand.

In some embodiments, there is provided a method of treating an individual having a disease or condition, comprising: (a) administering to the individual an imaging agent comprising an antibody moiety labeled with a radionuclide, wherein the antibody fragment specifically binds the immune checkpoint ligand; (b) imaging the imaging agent in the individual with a non-invasive imaging technique; (c) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest; and (d) administering to the individual an effective amount of a therapeutic agent targeting the immune checkpoint ligand or receptor thereof (e.g., an inhibitor of the immune checkpoint ligand or receptor thereof, or a radiolabeled molecule specifically binding the immune checkpoint ligand or receptor thereof), if the individual is diagnosed as positive for the immune checkpoint ligand. In some embodiments, the method further comprises determining the expression level of the immune checkpoint ligand in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the immune checkpoint ligand is selected from the group consisting of PD-L1, PD-L2, B7-H3, galectin-9, CD80, CD86 and ICOSL. In some embodiments, the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$. In some embodiments, the radionuclide is $^{68}Ga$. In some embodiments, the antibody moiety is conjugated to a chelating compound that chelates the radionuclide. In some embodiments, the chelating compound is NOTA, DOTA or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H. In some embodiments, the disease or condition is cancer, infection, autoimmune disease, or metabolic disease. In some embodiments, the immune checkpoint ligand is PD-L1. In some embodiments, the immune checkpoint ligand is a PD-L1 like ligand. In some embodiments, the antibody moiety is an scFv. In some embodiments, the antibody moiety is an scFv fused to an Fc fragment (such as a human IgG1 Fc).

In some embodiments, there is provided a method of treating an individual having a disease or condition, comprising: (a) administering to the individual an imaging agent comprising an anti-PD-L1 antibody moiety labeled with a radionuclide; (b) imaging the imaging agent in the individual with a non-invasive imaging technique; (c) diagnosing the individual as positive for PD-L1 if signal of the imaging agent is detected at a tissue of interest, or diagnosing the individual as negative for the immune checkpoint ligand if signal of the imaging agent is not detected at a tissue of interest; and (d) administering to the individual an effective amount of a therapeutic agent targeting PD-L1 or PD-1 (e.g., an inhibitor of PD-L1 or PD-1, such as an anti-PD-L1 antibody or anti-PD-1 antibody; or a radiolabeled molecule specifically binding PD-L1 or PD-1), if the individual is diagnosed as positive for PD-L1, wherein the anti-PD-L1 antibody moiety comprises: a V$_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a V$_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the method further comprises determining the expression level of PD-L1 in a tissue of interest in the individual based on signals emitted by the imaging agent from the tissue. In some embodiments, the method further comprises preparing the imaging agent by labeling the antibody moiety with the radionuclide. In some embodiments, the non-invasive imaging technique comprises single photon emission computed tomography (SPECT) imaging or positron emission tomography (PET) imaging. In some embodiments, the non-invasive imaging technique further comprises computed tomography imaging, magnetic resonance imaging, chemical luminescence imaging, or electrochemical luminescence imaging. In some embodiments, the imaging agent is administered intravenously, intraperitoneally, intramuscularly, subcutaneously, or orally. In some embodiments, the imaging is carried out between about 10 minutes to about 24 hours after the administration of the imaging agent. In some embodiments, the method further comprises administering to the individual an antibody moiety not labeled with a radioisotope prior to the administration of the imaging agent. In some embodiments, the method comprises imaging the individual over a period of time. In some embodiments, the anti-PD-L1 antibody moiety comprises: a V$_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a V$_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof. In some embodiments, the disease or condition is cancer, infection, autoimmune disease, or metabolic disease. In some embodiments, the antibody moiety is an scFv. In some embodiments, the antibody moiety is an scFv fused to an Fc fragment (such as a human IgG1 Fc). In some embodiments, the scFv comprises one or more (such as 1, 2, 3, or more) engineered disulfide bonds. In some embodiments, the scFv comprises a first engineered cysteine residue at position 44 of V$_H$ and a second engineered cysteine residue at position 100 of V$_L$, and/or a first engineered cysteine residue at position 105 of V$_H$ and a second engineered cysteine residue at position 43 of V$_L$, wherein the first engineered cysteine residue and the second engineered cysteine residue form a disulfide bond, and wherein the amino acid positions are based on the Kabat numbering system. In some embodiments, the anti-PD-L1 antibody moiety comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39.

In some embodiments, the individual has cancer. The cancer may comprise non-solid tumors (such as hematological tumors, for example, leukemias and lymphomas) or may comprise solid tumors. Exemplary cancers that may be diagnosed using the methods described herein, include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. Solid or hematologic cancers discussed herein include, but is not limited to, Hodgkin lymphoma, non-Hodgkin lymphoma, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, and melanoma.

The methods described herein are applicable to solid or hematologic cancers of all stages, including stages, I, II, III, and IV, according to the American Joint Committee on Cancer (AJCC) staging groups. In some embodiments, the solid or hematologic cancer is an/a: early stage cancer, non-metastatic cancer, primary cancer, advanced cancer, locally advanced cancer, metastatic cancer, or cancer in remission.

In some embodiments, the individual has a hematologic cancer. Exemplary hematologic cancers that can be diagnosed using the methods described herein include, but are not limited to, leukemia, lymphoma, acute lymphoblastic leukemia (ALL), acute non-lymphoblastic leukemia (ANLL), chronic lymphocytic leukemia (CLL), chronic myeloid leukemia (CML), non-Hodgkin lymphoma, and Hodgkin lymphoma.

In some embodiments, the individual has a solid tumor. Exemplary solid tumors that can be diagnosed using the methods described herein include, but are not limited to, colon tumor, melanoma, kidney tumor, ovarian tumor, lung tumor, breast tumor, and pancreatic tumor.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the individual has an infectious disease. The infection may be caused by a virus, bacteria, protozoa, or parasite. Exemplary pathogens include, but are not limited to, *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), Kingella kingae, *Klebsiella granulomatis*, Kuru prion, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In some embodiments, the individual has an autoimmune disease. Exemplary autoimmune disease include, but are not limited to, Behcet disease, systemic lupus erythematosus, multiple sclerosis (systemic scleroderma and progressive systemic scleroderma), scleroderma, polymyositis, dermatomyositis, periarteritis nodosa (polyarteritis nodosa and microscopic polyangiitis), aortitis syndrome (Takayasu arteritis), malignant rheumatoid arthritis, rheumatoid arthritis, Wegner's granulomatosis, mixed connective tissue disease, Sjogren syndrome, adult-onset Still's disease, allergic granulomatous angiitis, hypersensitivity angiitis, Cogan's syndrome, RS3PE, temporal arteritis, polymyalgia rheumatica, fibromyalgia syndrome, antiphospholipid antibody syndrome, eosinophilic fasciitis, IgG4-related diseases (e.g., primary sclerosing cholangitis and autoimmune pancreatitis), Guillain-Barre syndrome, myasthenia gravis, chronic atrophic gastritis, autoimmune hepatitis, primary biliary cirrhosis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Graves' disease (hyperthyroidism), Hashimoto's thyroiditis, autoimmune adrenal insufficiency, primary hypothyroidism, idiopathic Addison's disease (chronic adrenal insufficiency), type I diabetes mellitus, chronic discoid lupus erythematosus, localized scleroderma, psoriasis, psoriatic arthritis, pemphigus, pemphigoid, herpes gestationis, linear IgA bullous skin disease, epidermolysis bullosa acquisita, alopecia areata, vitiligo, Harada disease, autoimmune optic neuropathy, idiopathic azoospermia, recurrent fetal loss, and inflammatory bowel diseases (ulcerative colitis and Crohn's disease).

In some embodiments, the individual has a metabolic disease associated with abnormal immune response. Exemplary metabolic diseases include, but are not limited to, inflammatory bowel disease, multiple sclerosis, psoriasis, rheumatoid arthritis, and systemic lupus erythematosus.

III. Imaging Agents

One aspect of the present application provides an imaging agent comprising an antibody moiety labeled with a radionuclide, wherein the antibody moiety specifically binds an immune checkpoint ligand. Any one of the imaging agents described in this section may be used in the methods of determining the distribution and/or expression level of an immune checkpoint ligand, or methods of diagnosis or treatment described herein.

In some embodiments, there is provided an imaging agent comprising an antibody moiety labeled with a radionuclide, wherein the antibody moiety specifically binds an immune checkpoint ligand. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the antibody moiety is conjugated to a chelating compound that chelates the radionuclide. In some embodiments, the chelating compound is 1,4,7-triazacyclononane-1,4,7-trisacetic acid (NOTA), 1, 4, 7, 10-tetraazacyclododecane-1,4,7,10-tetraacetic acid (DOTA) or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H.

In some embodiments, there is provided an imaging agent comprising an antibody moiety conjugated to a chelating compound that chelates a radionuclide, wherein the antibody moiety specifically binds an immune checkpoint ligand. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is NOTA, DOTA or derivatives thereof. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a V$_H$H.

In some embodiments, the antibody moiety described herein has a half-life in the serum suitable for rapid clearance rate from the body, which is amenable for in vivo imaging. In some embodiments, the antibody moiety has a half-life in the serum of no more than about any one of 24 hours, 20 hours, 16 hours, 12 hours, 8 hours, 4 hours, 2 hours, 1 hour, 30 minutes or less. In some embodiments, the antibody moiety has a half-life in the serum of about 10 minutes to about 24 hours, including, for example, any one of about 10 minutes to about 30 minutes, about 30 minutes to about 1 hour, about 1 hour to about 2 hours, about 2 hours to about 3 hours, about 3 hours to about 4 hours, about 4 hours to about 6 hours, about 6 hours to about 8 hours, about 8 hours to about 12 hours, about 12 hours to about 16 hours, about 16 hours to about 20 hours, about 20 hours to about 24 hours, about 10 minutes to about 2 hours, about 1 hour to about 4 hours, about 4 hours to about 8 hours, about 8 hours to about 12 hours, or about 12 hours to about 24 hours. In some embodiments, the antibody moiety is cleared from the body no more than about any one of 48 hours, 36 hours, 30 hours, 24 hours, 20 hours, 16 hours, 12 hours, 8 hours, 4 hours, 2 hours, 1 hour, 30 minutes or less. In some embodiments, the antibody moiety is cleared from the body between about 10 minutes to about 48 hours, including, for example, any one of about 10 minutes to about 30 minutes, about 30 minutes to about 1 hour, about 1 hour to about 2 hours, about 2 hours to about 3 hours, about 3 hours to about 4 hours, about 4 hours to about 6 hours, about 6 hours to about 8 hours, about 8 hours to about 12 hours, about 12 hours to about 16 hours, about 16 hours to about 20 hours, about 20 hours to about 24 hours, about 24 hours to about 36 hours, about 36 hours to about 48 hours, about 10 minutes to about 2 hours, about 1 hour to about 4 hours, about 4 hours to about 8 hours, about 8 hours to about 12 hours, or about 12 hours to about 48 hours.

In some embodiments, the antibody moiety has a low molecular weight that enables its rapid clearance from the body. In some embodiments, the antibody moiety has a molecular weight of no more than about any one of 120 kDa, 110 kDa, 100 kDa, 90 kDa, 80 kDa, 70 kDa, 60 kDa, 50 kDa, 40 kDa or 30 kDa. In some embodiments, the antibody moiety has a molecular weight of about 15 kDa to about 30 kDa, about 30 kDa to about 50 kDa, about 50 kDa to about 100 kDa, about 80 kDa to about 120 kDa or about 15 kDa to about 120 kDa. For example, an scFv has a molecular weight of about 27 kDa, an Fc has a molecular weight of about 26 kDa, and an scFv-Fc has a molecular weight of about 80 kDa.

In some embodiments, the antibody moiety has a suitable affinity to the immune checkpoint ligand. In some embodiments, the antibody moiety has a $K_D$ to the immune checkpoint ligand that is stronger than about any one of $10^{-8}$ M, $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, $1\times10^{-9}$ M, or $9\times10^{-10}$ M. In some embodiments, the antibody moiety has a $K_D$ the immune checkpoint ligand that is weaker than about any one of $9\times10^{-10}$ M, $1\times10^{-9}$ M, $2\times10^{-9}$ M, $3\times10^{-9}$ M, $4\times10^{-9}$ M, $5\times10^{-9}$ M, $6\times10^{-9}$ M, $7\times10^{-9}$ M, $8\times10^{-9}$ M, $9\times10^{-9}$ M, or $10^{-8}$ M. In some embodiments, the antibody moiety has a $K_D$ to the immune checkpoint ligand that is about any one of $9\times10^{-10}$ M to $1\times10^{-8}$ M, $9\times10^{-10}$ M to $1\times10^{-9}$ M, $1\times10^{-9}$ M to $2\times10^{-9}$ M, $2\times10^{-9}$ M to $3\times10^{-9}$ M, $3\times10^{-9}$ M to $4\times10^{-9}$ M, $4\times10^{-9}$ M to $5\times10^{-9}$ M, $5\times10^{-9}$ M to $6\times10^{-9}$ M, $6\times10^{-9}$ M to $7\times10^{-9}$ M, $7\times10^{-9}$ M to $8\times10^{-9}$ M, $8\times10^{-9}$ M to $9\times10^{-9}$ M, $9\times10^{-9}$ M to $1\times10^{-8}$ M, $2\times10^{-10}$ to $5\times10^{-9}$, or $5\times10^{-10}$ to $1\times10^{-8}$.

In some embodiments, the antibody moiety is stable at acidic pH or neutral pH. In some embodiments, the antibody moiety is stable at a pH lower than about 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0 or less. In some embodiments, the antibody moiety is stable at an acidic pH or neutral pH for at least about any one of 4 hours, 6 hours, 8 hours, 10 hours, 12 hours, 24 hours, 48 hours, 3 days, 4 days, 5 days, 6 days, 7 days or more. In some embodiments, the antibody moiety is stable at basic pH, for example at a pH higher than about 7.0, 7.5, 8.0, 8.5 or higher. In some embodiments, the antibody moiety is stable at a basic pH for at least about any one of 4 hours, 8 hours, 12 hours, 24 hours, 48 hours, 3 days, 5 days, 7 days or more. Stability can be measured by incubating the imaging agent or antibody moiety in a buffer having the corresponding pH over a period of time (such as 12 hours, 24 hours, or longer), and assessing the integrity of the imaging agent or antibody moiety using known methods in the art, including SDS-PAGE, dynamic light scattering, chromatography, NMR, etc.

In some embodiments, the antibody moiety is stable at an elevated temperature, e.g., at room temperature or physiological temperature. In some embodiments, the antibody moiety has a melting temperature of at least about any one of 50° C., 55° C., 60° C., 61° C., 62° C., 63° C., 64° C., 65° C., 66° C., 67° C., 68° C., 69° C., 70° C. or higher. In some embodiments, the antibody moiety has a melting temperature of about 550 to about 70° C., including, for example, about any one of 55° C.-60° C., 60° C.-65° C., 50° C.-65° C., 64° C.-68° C., or 65° C.-70° C. Melting temperature of an antibody moiety can be measured using any known methods in the art, including, for example, Differential Scanning Fluorimetry (DSF).

In some embodiments, the antibody moiety is engineered with one or more disulfide bonds to increase the melting temperature or stability of the antibody moiety. In some embodiments, wherein the antibody moiety comprises an scFv, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. Other engineered disulfide bonds may be introduced into the scFv by engineering a cysteine in the VH and a cysteine in the VL at suitable positions based on the structure and sequences of the scFv.

Contemplated antibody moieties include, but are not limited to, humanized antibodies, partially humanized antibodies, fully humanized antibodies, semi-synthetic antibodies, chimeric antibodies, mouse antibodies, human antibodies, and antibodies comprising the heavy chain and/or light chain CDRs discussed herein, e.g., in the "anti-PD-L1 antibody agents" section.

In some embodiments, the antibody moiety specifically recognizes the immune checkpoint ligand from human. In some embodiments, the antibody moiety cross-reacts with the immune checkpoint ligand from two or more species. Cross-reactivity of the antibody moiety with model animals and human facilities clinical studies of the imaging agent. In some embodiments, the antibody moiety cross-reacts with the immune checkpoint ligand from a non-human animal, such as mammal. In some embodiments, the antibody moiety cross-reacts with the immune checkpoint ligand from a rodent, such as mouse or rat. In some embodiments, the antibody moiety cross-reacts with the immune checkpoint ligand from a non-human primate, such as a cynomolgus monkey.

In some embodiments, the antibody moiety is an antigen-binding fragment. In some embodiments, the antibody moiety is not a full-length antibody. Suitable antibody moieties include, but are not limited to, scFv, Fab, Fab', F(ab')$_2$, Fv, disulfide stabilized Fv fragment (dsFv), a (dsFv)$_2$, $V_H$H, and Fc fusions thereof. In some embodiments, the antibody moiety is an scFv. Antibody fragments and variants that are suitable for the imaging agents described herein are further described in the section "Antibody moieties." In some embodiments, the antibody moiety is a Fab. In some embodiments, the antibody moiety is an scFv fused to an Fc fragment.

Thus, in some embodiments, there is provided an imaging agent comprising a scFv labeled with a radionuclide, wherein the scFv specifically binds an immune checkpoint ligand. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the scFv is conjugated to a chelating compound that chelates the radionuclide. In some embodiments, the chelating compound is NOTA, DOTA or derivatives thereof. In some embodiments, the scFv has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the scFv cross-reacts with the immune checkpoint ligand from a non-human mammal (e.g., mouse, rat or monkey). In some embodiments, the scFv is humanized. In some embodiments, the scFv is stable at acidic pH (e.g., at a pH lower than about 6.5, 6.0, 5.5, or 5.0). In some embodiments, the scFv has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a $V_H$, an optional peptide linker, and a $V_L$. In some embodiments, the scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

In some embodiments, there is provided an imaging agent comprising an antibody moiety labeled with a radionuclide, wherein the antibody moiety specifically binds an immune checkpoint ligand, and wherein the antibody moiety is an scFv fused to an Fc fragment. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{44}$Sc, $^{47}$Sc, $^{86}$Y, $^{88}$Y and $^{45}$Ti. In some embodiments, the radionuclide is $^{68}$Ga. In some embodiments, the antibody moiety is conjugated to a chelating compound that chelates the radionuclide. In some embodiments, the chelating compound is NOTA, DOTA or derivatives thereof. In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a $V_H$, an optional peptide linker, and a $V_L$. In some embodiments, the scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is a human IgG1 Fc fragment. In some embodiments, the Fc fragment has H310A and H435Q mutations, wherein the amino acid positions are based on the Kabat numbering system.

In some embodiments, there is provided an imaging agent comprising an antibody moiety labeled conjugated to a chelating compound (e.g., NOTA, DOTA, or derivatives thereof) that chelates a radionuclide (e.g., $^{68}$Ga), wherein the antibody moiety specifically binds an immune checkpoint ligand, and wherein the antibody moiety is an scFv fused to an Fc fragment. In some embodiments, there is provided an imaging agent comprising an antibody moiety conjugated to NOTA that chelates a radionuclide (e.g., $^{68}$Ga), wherein the antibody moiety specifically binds an immune checkpoint ligand. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a $V_H$H. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti.

In some embodiments, there is provided an imaging agent comprising a scFv conjugated to a chelating compound (e.g., NOTA, DOTA, or derivative thereof) that chelates a radionuclide (e.g., $^{68}$Ga), wherein the scFv specifically binds an immune checkpoint ligand. In some embodiments, there is provided an imaging agent comprising a scFv conjugated to NOTA that chelates a radionuclide (e.g., $^{68}$Ga), wherein the scFv specifically binds an immune checkpoint ligand. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the scFv has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the scFv cross-reacts with the immune checkpoint ligand from a non-human mammal (e.g., mouse, rat or monkey). In some embodiments, the scFv is humanized. In some embodiments, the scFv is stable at acidic pH (e.g., at a pH lower than about 6.5, 6.0, 5.5, or 5.0). In some embodiments, the scFv has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a $V_H$, an optional peptide linker, and a $V_L$. In some embodiments, the scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti.

In some embodiments, there is provided an imaging agent comprising an antibody moiety conjugated to NOTA that chelates a radionuclide (e.g., $^{68}$Ga), wherein the antibody moiety specifically binds an immune checkpoint ligand, and wherein the antibody moiety is an scFv fused to an Fc fragment. In some embodiments, the immune checkpoint ligand is selected from the group consisting of PD-L1, PD-L2, B7-H3, galectin-9, CD80, CD86 and ICOSL. In some embodiments, the immune checkpoint ligand is a PD-L1 like ligand. In some embodiments, the antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the antibody moiety cross-reacts with the immune checkpoint ligand from a non-human mammal (e.g., mouse, rat or monkey). In some embodiments, the antibody moiety is humanized. In some embodiments, the antibody moiety is stable at acidic pH (e.g., at a pH lower than about 6.5, 6.0, 5.5, or 5.0). In some embodiments, the antibody moiety has a melting temperature (Tm) of about 55-70° C. (such as about any one of 55-60, 60-65, or 65-70° C.). In some embodiments, the scFv comprises one or more engineered disulfide bonds. In some embodiments, the scFv comprises from the N-terminus to the C-terminus: a $V_H$, an optional peptide linker, and a $V_L$. In some embodiments, the scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is a human IgG1 Fc fragment. In some embodiments, the Fc fragment has H310A and H435Q mutations, wherein the amino acid positions are based on the Kabat numbering system. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti.

In some embodiments, there is provided an imaging agent comprising an anti-PD-L1 antibody moiety labeled with a radionuclide, wherein the anti-PD-L1 antibody moiety specifically binds PD-L1. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof. In some embodiments, the anti-PD-L1 antibody moiety has a half-life of about 10 minutes to about 24 hours (such as about any one of 10 minutes to 2 hours, 1 hour to 4 hours, 4 hours to 8 hours, 8 hours to 12 hours or 12 hours to 24 hours) in serum. In some embodiments, the anti-PD-L1 antibody moiety is no more than about 120 kDa (such as no more than about 30 kDa, 50 kDa, 80 kDa, or 100 kDa, or about any one of 30-50 kDa, 50-100 kDa, or 30-80 kDa). In some embodiments, the anti-PD-L1 antibody moiety has a $K_D$ between about $9\times10^{-10}$ M to about $1\times10^{-8}$ M (such as about $9\times10^{-10}$ to $1\times10^{-9}$, about $1\times10^{-9}$ to $2\times10^{-9}$, about $2\times10^{-10}$ to $5\times10^{-9}$, or about $5\times10^{-10}$ to $1\times10^{-8}$) with the immune checkpoint ligand. In some embodiments, the anti-PD-L1 antibody moiety cross-reacts with the immune checkpoint ligand from a non-human mammal (e.g., mouse, rat or monkey). In some embodiments, the anti-PD-L1 antibody moiety is humanized. In some embodiments, the anti-PD-L1 antibody moiety is stable at acidic pH (e.g., at a pH lower than about 6.5, 6.0, 5.5, or 5.0). In some embodiments, the anti-PD-L1 antibody moiety has a melting temperature (Tm) of about 55-70° C. (such as about any one of 55-60, 60-65, or 65-70° C.). In some embodiments, the anti-PD-L1 antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a $V_H$H. In some embodiments, the anti-PD-L1 antibody moiety is an scFv. In some embodiments, the anti-PD-L1 antibody moiety is an scFv fused to an Fc. Exemplary anti-PD-L1 antibody moieties are discussed in detail in the "Anti-PD-L1 antibody agents" section.

Radionuclide

The imaging agents described herein comprise a label. For diagnostic purposes, the label may be a radionuclide, a radiological contrast agent, a paramagnetic ion, a metal, a fluorescent label, a chemiluminescent label, an ultrasound contrast agent and a photoactive agent. Such diagnostic labels are well known and any such known labels may be used.

In some embodiments, the imaging agent comprises a radionuclide. "Radionuclides" are often referred to as "radioactive isotopes" or "radioisotopes." Exemplary radionuclides or stable isotopes that may be attached to the antibody moieties described herein include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{131}$I, $^{154-158}$Gd, $^{32}$P, $^{11}$C, $^{13}$N, $^{15}$O, $^{186}$Re, $^{18}$Re, $^{51}$Mn, $^{52m}$Mn, $^{55}$Co, $^{72}$As, $^{7}$Br, $^{76}$Br, $^{82m}$Rb, $^{83}$Sr, or other gamma-, beta-, or positron-emitters. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$G.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoelytherin, phycocyanin, allophycocyanin, ophthaldehyde and fluorescamine. Chemiluminescent labels of use may include luminol, isoluminol, an aromatic acridinium ester, an imidazole, an acridinium salt or an oxalate ester.

Radioimmunodetection (RAID) has emerged as a clinically useful field over the last 35 years. Almost 1000 clinical trials using RAID have been conducted during this time, with some clear and important findings. The greater facility of this technique to detect lesions deemed "occult" by conventional imaging was recognized even in early studies and has repeatedly been confirmed by studies, regardless of antibody, tumor or radionuclide type.

Many radionuclides, such as $^{68}$Ga, $^{99}$Tc, $^{64}$Cu and $^{18}$F are good imaging agent of choice. They usually have a gamma or beta energy that is ideal for safe imaging, and are inexpensive and are readily available, being generator-produced and carrier-free. Their short half-life (less than 6 hrs) readily lends themselves to coupling with antibody fragments for early imaging studies.

In some embodiments, the imaging agent comprises a chelating compound that chelates the radionuclide. In some embodiments, the chelating compound chelates a radioactive metal. In some embodiments, the chelating compound chelates a metal $^{18}$F. In some embodiments, the chelating compound is a hydrophilic chelating compound, which can bind metal ions and help to ensure rapid in vivo clearance. Suitable chelating compounds may be selected for their particular metal-binding properties, and substitution by known chemical cross-linking techniques or by use of chelators with side-chain reactive groups (such as bifunctional chelating compounds) may be performed with only routine experimentation.

Particularly useful metal-chelating compound combinations include 2-benzyl-DTPA (diethylenetriamine pentaacetic acid) and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99}$Tc, $^{94}$Tc, $^{11}$C, $^{13}$N, $^{15}$O, $^{76}$Br, for radio-imaging. The same chelating compounds, when complexed with nonradioactive metals, such as manganese, iron and gadolinium are useful for MRI. Macrocyclic chelating compounds such as NOTA (1,4,7-triazacyclononane-1,4,7-triacetic acid), DOTA (1,4,7,10-Tetraazacyclododecane-N,N', N'',N'''-tetraacetic acid), TETA (bromoacetamido-benzyl-tetraethylaminetetraacetic acid) and NETA ({4-[2-(bis-carboxymethyl-amino)-ethyl]-7-carboxymethyl-[1,4,7] triazonan-1-yl}-acetic acid) are of use with a variety of diagnostic radiometals, such as gallium, yttrium and copper.

Such metal-chelating complexes can be made very stable by tailoring the ring size to the metal of interest. The person of ordinary skill will understand that, by varying the groups attached to a macrocyclic ring structure such as NOTA, the binding characteristics and affinity for different metals and/or radionuclides may change and such derivatives or analogs of, e.g. NOTA, may therefore be designed to bind any of the metals or radionuclides discussed herein.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a peptide to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. Other hard acid chelators such as DOTA, TETA and the like can be substituted for the DTPA and/or TscgCys groups.

In some embodiments, the chelating compound comprises a functional group that can be conjugated to the antibody moiety. In some embodiments, the chelating compound comprises a functional group that is reactive with a primary amine (—NH$_2$) group in the antibody moiety. Primary amines exist at the N-terminus of each polypeptide chain and in the side-chain of lysine (Lys) amino acid residues. Exemplary functional groups that can be conjugated to a primary amine, e.g., a lysine side chain, of the antibody moiety, include, but are not limited to, isothiocyanates, isocyanates, acyl azides, N-hydroxysuccinimide (NHS) esters, sulfonyl chlorides, aldehydes, glyoxals, epoxides, oxiranes, carbonates, aryl halides, imidoesters, carbodiimides, anhydrides, and fluorophenyl esters. Most of these functional groups conjugate to amines by either acylation or alkylation.

In some embodiments, the chelating compound comprises a functional group that is reactive with a cysteine side chain (i.e., sulfhydryl group) in the antibody moiety. Exemplary sulfhydryl reactive groups include, but are not limited to, haloacetyls, maleimides, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond).

Figure 23:
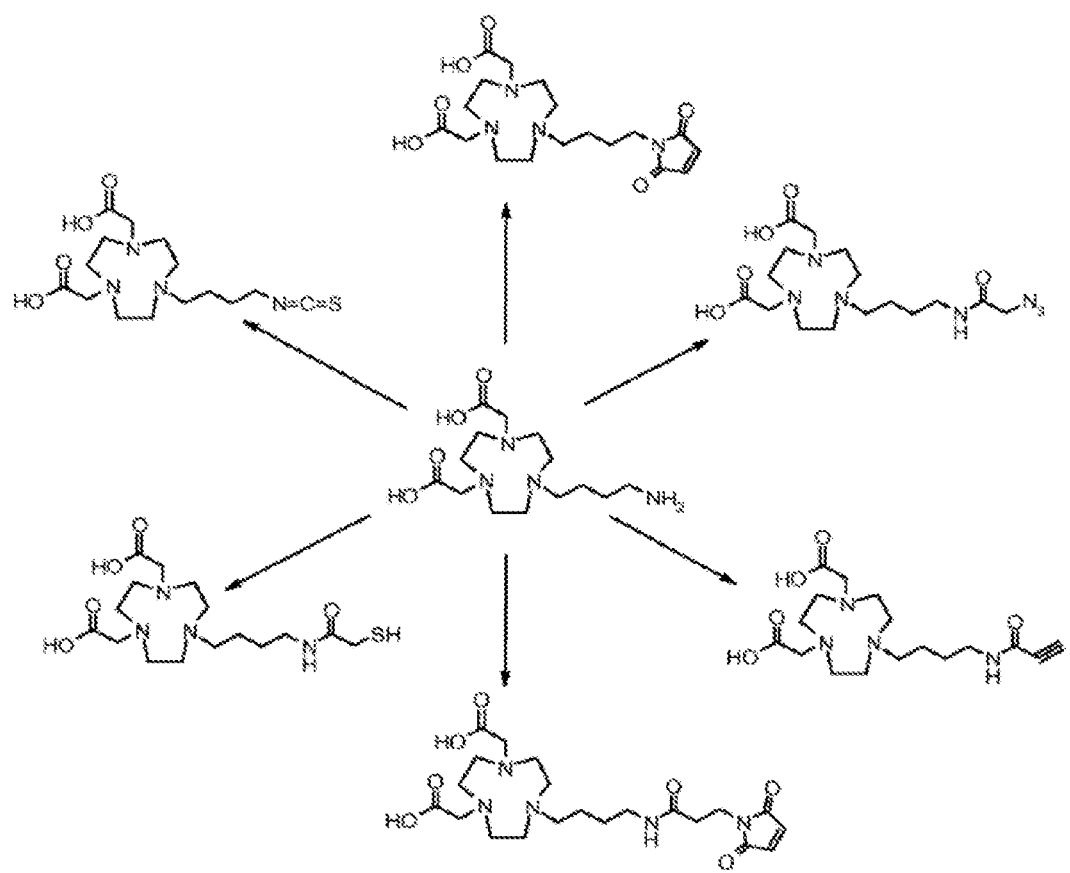
FIG. 23 shows exemplary NOTA compounds that can be used to chelate a radionuclide and to conjugate to an antibody moiety.

In some embodiments, the chelating compound is NOTA, including NOTA derivatives. Exemplary NOTA compounds with functional groups suitable for conjugation to antibody moieties, e.g., via amino acid side chains such as lysines and cysteines, are shown in FIG. 23. In some embodiments, the imaging agent comprises NOTA conjugated to the antibody moiety. In some embodiments, the NOTA compound comprises an isothiocyanate (—SCN) group. In some embodiments, the NOTA compound is p-SCN-Bn-NOTA. In some embodiments, the chelating compound comprises a NOTA conjugated to a lysine residue in the antibody moiety, and the NOTA chelates $^{68}$Ga. In some embodiments, the NOTA compound is first labeled with a radioactive metal, such as $^{68}$Ga, or $^{18}$F-metal, and then conjugated to the antibody moiety.

IV. Anti-PD-L1 Antibody Agents

One aspect of the present application provides an isolated anti-PD-L1 antibody agent and an anti-PD-L1 imaging agent. The isolated anti-PD-L1 antibody agent may be unlabeled or labeled with a radionuclide. The isolated anti-PD-L1 antibody agents described herein do not encompass anti-PD-L1 therapeutic agents.

In some embodiments, there is provided an isolated anti-PD-L1 antibody agent comprising any one of the anti-PD-L1 antibody moieties described herein. In some embodiments, the anti-PD-L1 antibody moiety is humanized. In some embodiments, the anti-PD-L1 antibody moiety comprises an scFv. In some embodiments, the anti-PD-L1 antibody moiety is an scFv. In some embodiments, the scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the anti-PD-L1 antibody moiety is an scFv fused to an Fc fragment (such as IgG1 Fc fragment). In some embodiments, the Fc fragment has H310A and H435Q mutations, wherein the amino acid positions are based on the Kabat numbering system.

In some embodiments, there is provided an isolated anti-PD-L1 antibody agent comprising an anti-PD-L1 antibody moiety comprising: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized.

In some embodiments, there is provided an isolated anti-PD-L1 antibody agent comprising an anti-PD-L1 scFv comprising: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39.

In some embodiments, there is provided an isolated anti-PD-L1 antibody agent comprising an anti-PD-L1 scFv fused to an Fc fragment, wherein the anti-PD-L1 scFv comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39.

Anti-PD-L1 Antibody Moieties

The isolated anti-PD-L1 antibody agents described herein comprise an antibody moiety that specifically binds to PD-L1. Contemplated anti-PD-L1 antibody moieties include, for example, anti-PD-L1 scFv, anti-PD-L1 Fab, anti-PD-L1 Fc fusion protein (e.g., anti-PD-L1 scFv fused to an Fc). The anti-PD-L1 antibody moieties described herein include, but are not limited to, humanized antibodies, partially humanized antibodies, fully humanized antibodies, semi-synthetic antibodies, chimeric antibodies, mouse antibodies, human antibodies, and antibodies comprising the heavy chain and/or light chain CDRs discussed herein.

In some embodiments, the anti-PD-L1 antibody moiety specifically recognizes PD-L1. In some embodiments, the anti-PD-L1 antibody moiety specifically recognizes human PD-L1. In some embodiments, the anti-PD-L1 antibody moiety specifically recognizes the extracellular domain of PD-L1. In some embodiments, the anti-PD-L1 antibody moiety specifically recognizes an epitope within the amino acid sequence of amino acids 19-238 of SEQ ID NO: 49.

```
human PD-L1 sequence
                                      SEQ ID NO: 49
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET
```

In some embodiments, the anti-PD-L1 antibody moiety comprises: a heavy chain variable domain ($V_H$) comprising an HC-CDR3 comprising the amino acid sequence of SEQ ID NO: 43, or a variant thereof comprising up to about 5 (such as about any of 1, 2, 3, 4, or 5) amino acid substitutions; and ii) a light chain variable domain ($V_L$) comprising an LC-CDR3 comprising the amino acid sequence of SEQ ID NO: 46, or a variant thereof comprising up to about 5 (such as about any of 1, 2, 3, 4, or 5) amino acid substitutions.

In some embodiments, the anti-PD-L1 antibody moiety comprises: i) a $V_H$ comprising an HC-CDR3 comprising the amino acid sequence of SEQ ID NO: 43; and ii) a $V_L$ comprising an LC-CDR3 comprising the amino acid sequence of SEQ ID NO: 46.

In some embodiments, the anti-PD-L1 antibody moiety comprises: i) a $V_H$ comprising an HC-CDR1 comprising the amino acid sequence of SEQ ID NO: 41, or a variant thereof comprising up to about 5 (such as about any of 1, 2, 3, 4, or 5) amino acid substitutions, an HC-CDR2 comprising the amino acid sequence of SEQ ID NO: 42, or a variant thereof comprising up to about 5 (such as about any of 1, 2, 3, 4, or 5) amino acid substitutions, and an HC-CDR3 comprising the amino acid sequence of a SEQ ID NO: 43, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 44, or a variant thereof comprising up to about 5 (such as about any of 1, 2, 3, 4, or 5) amino acid substitutions, an LC-CDR2 comprising the amino acid sequence of SEQ ID NO: 45, or a variant thereof comprising up to about 5 (such as about any of 1, 2, 3, 4, or 5) amino acid substitutions, and an LC-CDR3 comprising the amino acid sequence of SEQ ID NO: 46, or a variant thereof comprising up to about 5 (such as about any of 1, 2, 3, 4, or 5) amino acid substitutions.

In some embodiments, the anti-PD-L1 antibody moiety comprises: i) a $V_H$ comprising an HC-CDR1 comprising the amino acid sequence of SEQ ID NO: 41, an HC-CDR2 comprising the amino acid sequence of SEQ ID NO: 42, and an HC-CDR3 comprising the amino acid sequence of a SEQ ID NO: 43; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 44, an LC-CDR2 comprising the amino acid sequence of SEQ ID NO: 45, and an LC-CDR3 comprising the amino acid sequence of SEQ ID NO: 46; or a variant thereof comprising up to about 5 (such as about any of 1, 2, 3, 4, or 5) amino acid substitutions in the LC-CDR sequences.

In some embodiments, the anti-PD-L1 antibody moiety comprises: i) a $V_H$ comprising an HC-CDR1 comprising the amino acid sequence of SEQ ID NO: 41, an HC-CDR2 comprising the amino acid sequence of SEQ ID NO: 42, and an HC-CDR3 comprising the amino acid sequence of a SEQ ID NO: 43; and ii) a $V_L$ comprising an LC-CDR1 comprising the amino acid sequence of SEQ ID NO: 44, an LC-CDR2 comprising the amino acid sequence of SEQ ID NO: 45, and an LC-CDR3 comprising the amino acid sequence of SEQ ID NO: 46.

In some embodiments, the anti-PD-L1 antibody moiety comprises: i) a $V_H$ comprising the amino acid sequences of SEQ ID NO: 41, SEQ ID NO: 42, and SEQ ID NO: 43; and ii) a $V_L$ comprising the amino acid sequences of SEQ ID NO: 44, SEQ ID NO: 45, and SEQ ID NO: 46.

In some embodiments, the anti-PD-L1 antibody moiety comprises: i) a $V_H$ comprising one, two or three CDRs of the $V_H$ comprising the amino acid sequence of SEQ ID NO: 1; and ii) a $V_L$ comprising one, two or three CDRs of the VL comprising the amino acid sequence of SEQ ID NO: 3.

In some embodiments, the anti-PD-L1 antibody moiety comprises: a) a $V_H$ comprising the amino acid sequence of SEQ ID NO: 1, or a variant thereof having at least about 80% (such as at least about any one of 80%, 85%, 90%, 95%, 96%, 97%, 98%, or 99%) sequence identity to SEQ ID NO: 1; and b) a $V_L$ comprising the amino acid sequence of SEQ ID NO: 2, or a variant thereof having at least about 80% (such as at least about any one of 80%, 85%, 90%, 95%, 96%, 97%, 98%, or 99%) sequence identity to SEQ ID NO: 2. In some embodiment, the anti-PD-L1 antibody moiety comprises: a) a $V_H$ comprising the amino acid sequence of SEQ ID NO: 1; and b) a $V_L$ comprising the amino acid sequence of SEQ ID NO: 2.

In some embodiments, the anti-PD-L1 antibody is a chimeric antibody. In some embodiments, the anti-PD-L1 antibody moiety comprises mouse CDRs and human FR sequences. In some embodiments, the anti-PD-L1 antibody moiety comprises: a) a $V_H$ comprising the amino acid sequence of SEQ ID NO: 5, or a variant thereof having at least about 80% (such as at least about any one of 80%, 85%, 90%, 95%, 96%, 97%, 98%, or 99%) sequence identity to SEQ ID NO: 5; and b) a $V_L$ comprising the amino acid sequence of SEQ ID NO: 7, or a variant thereof having at least about 80% (such as at least about any one of 80%, 85%, 90%, 95%, 96%, 97%, 98%, or 99%) sequence identity to SEQ ID NO: 7. In some embodiment, the anti-PD-L1 antibody moiety comprises: a) a $V_H$ comprising the amino acid sequence of SEQ ID NO: 5; and b) a $V_L$ comprising the amino acid sequence of SEQ ID NO: 7.

In some embodiments, the anti-PD-L1 antibody is a humanized antibody. In some embodiments, the anti-PD-L1 antibody moiety comprises: a) a $V_H$ comprising the amino acid sequence of any one of SEQ ID NOs: 9, 11 and 13, or a variant thereof having at least about 80% (such as at least about any one of 80%, 85%, 90%, 95%, 96%, 97%, 98%, or 99%) sequence identity to any one of SEQ ID NOs: 9, 11 and 13; and b) a $V_L$ comprising the amino acid sequence of any one of SEQ ID NOs: 15, 17 and 19, or a variant thereof having at least about 80% (such as at least about any one of 80%, 85%, 90%, 95%, 96%, 97%, 98%, or 99%) sequence identity to any one of SEQ ID NOs: 15, 17 and 19. In some embodiments, the anti-PD-L1 antibody moiety comprises: a) a $V_H$ comprising the amino acid sequence of any one of SEQ ID NOs: 9, 11 and 13; and b) a $V_L$ comprising the amino acid sequence of any one of SEQ ID NOs: 15, 17 and 19.

In some embodiments, the anti-PD-L1 antibody moiety comprises: a) a $V_H$ comprising the amino acid sequence of SEQ ID NO: 9, or a variant thereof having at least about 80% (such as at least about any one of 80%, 85%, 90%, 95%, 96%, 97%, 98%, or 99%) sequence identity to SEQ ID NO: 9; and b) a $V_L$ comprising the amino acid sequence of SEQ ID NO: 15, or a variant thereof having at least about 80% (such as at least about any one of 80%, 85%, 90%, 95%, 96%, 97%, 98%, or 99%) sequence identity to SEQ ID NO: 15. In some embodiments, the anti-PD-L1 antibody moiety comprises: a) a $V_H$ comprising the amino acid sequence of SEQ ID NO: 9; and b) a $V_L$ comprising the amino acid sequence of SEQ ID NO: 15.

In some embodiments, the anti-PD-L1 antibody moiety comprises: a) a $V_H$ comprising the amino acid sequence of SEQ ID NO: 11, or a variant thereof having at least about 80% (such as at least about any one of 80%, 85%, 90%, 95%, 96%, 97%, 98%, or 99%) sequence identity to SEQ ID NO: 11; and b) a $V_L$ comprising the amino acid sequence of SEQ ID NO: 15, or a variant thereof having at least about 80% (such as at least about any one of 80%, 85%, 90%, 95%, 96%, 97%, 98%, or 99%) sequence identity to SEQ ID NO: 15. In some embodiments, the anti-PD-L1 antibody moiety comprises: a) a $V_H$ comprising the amino acid sequence of SEQ ID NO: 11; and b) a $V_L$ comprising the amino acid sequence of SEQ ID NO: 15.

In some embodiments, the anti-PD-L1 antibody moiety comprises: a) a $V_H$ comprising the amino acid sequence of SEQ ID NO: 13, or a variant thereof having at least about 80% (such as at least about any one of 80%, 85%, 90%, 95%, 96%, 97%, 98%, or 99%) sequence identity to SEQ ID NO: 13; and b) a $V_L$ comprising the amino acid sequence of SEQ ID NO: 15, or a variant thereof having at least about 80% (such as at least about any one of 80%, 85%, 90%, 95%, 96%, 97%, 98%, or 99%) sequence identity to SEQ ID NO: 15. In some embodiments, the anti-PD-L1 antibody moiety comprises: a) a $V_H$ comprising the amino acid sequence of SEQ ID NO: 13; and b) a $V_L$ comprising the amino acid sequence of SEQ ID NO: 15.

In some embodiments, the anti-PD-L1 antibody moiety comprises: a) a $V_H$ comprising the amino acid sequence of SEQ ID NO: 9, or a variant thereof having at least about 80% (such as at least about any one of 80%, 85%, 90%, 95%, 96%, 97%, 98%, or 99%) sequence identity to SEQ ID NO: 9; and b) a $V_L$ comprising the amino acid sequence of SEQ ID NO: 17, or a variant thereof having at least about 80% (such as at least about any one of 80%, 85%, 90%, 95%, 96%, 97%, 98%, or 99%) sequence identity to SEQ ID NO: 17. In some embodiments, the anti-PD-L1 antibody moiety comprises: a) a $V_H$ comprising the amino acid sequence of SEQ ID NO: 9; and b) a $V_L$ comprising the amino acid sequence of SEQ ID NO: 17.

In some embodiments, the anti-PD-L1 antibody moiety comprises: a) a $V_H$ comprising the amino acid sequence of SEQ ID NO: 11, or a variant thereof having at least about 80% (such as at least about any one of 80%, 85%, 90%, 95%, 96%, 97%, 98%, or 99%) sequence identity to SEQ ID NO: 11; and b) a $V_L$ comprising the amino acid sequence of SEQ ID NO: 17, or a variant thereof having at least about 80% (such as at least about any one of 80%, 85%, 90%, 95%, 96%, 97%, 98%, or 99%) sequence identity to SEQ ID NO: 17. In some embodiments, the anti-PD-L1 antibody moiety comprises: a) a $V_H$ comprising the amino acid sequence of SEQ ID NO: 11; and b) a $V_L$ comprising the amino acid sequence of SEQ ID NO: 17.

In some embodiments, the anti-PD-L1 antibody moiety comprises: a) a $V_H$ comprising the amino acid sequence of SEQ ID NO: 13, or a variant thereof having at least about 80% (such as at least about any one of 80%, 85%, 90%, 95%, 96%, 97%, 98%, or 99%) sequence identity to SEQ ID NO: 13; and b) a $V_L$ comprising the amino acid sequence of SEQ ID NO: 17, or a variant thereof having at least about 80% (such as at least about any one of 80%, 85%, 90%, 95%, 96%, 97%, 98%, or 99%) sequence identity to SEQ ID NO: 17. In some embodiments, the anti-PD-L1 antibody moiety comprises: a) a $V_H$ comprising the amino acid sequence of SEQ ID NO: 13; and b) a $V_L$ comprising the amino acid sequence of SEQ ID NO: 17.

In some embodiments, the anti-PD-L1 antibody moiety comprises: a) a $V_H$ comprising the amino acid sequence of SEQ ID NO: 9, or a variant thereof having at least about 80% (such as at least about any one of 80%, 85%, 90%, 95%, 96%, 97%, 98%, or 99%) sequence identity to SEQ ID NO: 9; and b) a $V_L$ comprising the amino acid sequence of SEQ ID NO: 19, or a variant thereof having at least about 80% (such as at least about any one of 80%, 85%, 90%, 95%, 96%, 97%, 98%, or 99%) sequence identity to SEQ ID NO: 19. In some embodiments, the anti-PD-L1 antibody moiety comprises: a) a $V_H$ comprising the amino acid sequence of SEQ ID NO: 9; and b) a $V_L$ comprising the amino acid sequence of SEQ ID NO: 19.

In some embodiments, the anti-PD-L1 antibody moiety comprises: a) a $V_H$ comprising the amino acid sequence of SEQ ID NO: 11, or a variant thereof having at least about 80% (such as at least about any one of 80%, 85%, 90%, 95%, 96%, 97%, 98%, or 99%) sequence identity to SEQ ID NO: 11; and b) a $V_L$ comprising the amino acid sequence of SEQ ID NO: 19, or a variant thereof having at least about 80% (such as at least about any one of 80%, 85%, 90%, 95%, 96%, 97%, 98%, or 99%) sequence identity to SEQ ID NO: 19. In some embodiments, the anti-PD-L1 antibody moiety comprises: a) a $V_H$ comprising the amino acid sequence of SEQ ID NO: 11; and b) a $V_L$ comprising the amino acid sequence of SEQ ID NO: 19.

In some embodiments, the anti-PD-L1 antibody moiety comprises: a) a $V_H$ comprising the amino acid sequence of SEQ ID NO: 13, or a variant thereof having at least about 80% (such as at least about any one of 80%, 85%, 90%, 95%, 96%, 97%, 98%, or 99%) sequence identity to SEQ ID NO: 13; and b) a $V_L$ comprising the amino acid sequence of SEQ ID NO: 19, or a variant thereof having at least about 80% (such as at least about any one of 80%, 85%, 90%, 95%, 96%, 97%, 98%, or 99%) sequence identity to SEQ ID NO: 19. In some embodiments, the anti-PD-L1 antibody moiety comprises: a) a $V_H$ comprising the amino acid sequence of SEQ ID NO: 13; and b) a $V_L$ comprising the amino acid sequence of SEQ ID NO: 19.

The heavy and light chain variable domains can be combined in various pair-wise combinations to generate a number of anti-PD-L1 antibody moieties. Exemplary sequences of anti-PD-L1 antibodies are provided in Tables 3 and 4. The exemplary CDR, VH and VL sequences as shown in Table 3 are delimited according to the INTERNATIONAL IMMUNOGENETICS INFORMATION SYSTEM® (IMGT). See, for example, Lefranc, M P et al., *Nucleic Acids Res.*, 43:D413-422 (2015), the disclosure of which is incorporated herein by reference in its entirety. Those skilled in the art will recognize that many algorithms are known for prediction of CDR positions in antibody heavy chain and light chain variable regions, and antibody agents comprising CDRs from antibodies described herein, but based on prediction algorithms other than IMGT, are within the scope of this invention. Table 4 lists exemplary CDR sequences under various other numbering schemes and/or definitions.

TABLE 3

Exemplary anti-PD-L1 antibody sequences.

| SEQ ID NO. AA | DNA | Description | Amino acid sequence (CDR sequences are underlined and bold) |
|---|---|---|---|
| 1 | 2 | VH | EVQLQQSGAELVKPGASVKLSCTASGFNIKDTYMYWVKQRPEQGLECIGRID PANDNTKYDPKFQGKATITADTSSNTAYVQLASLTSEDTAVYYCARAKNLLN YFDYWGQGTTLTVSS |
| 3 | 4 | VL | DIQMTQSPSSLSASLGERVTLSCRASQEISGYLSWLQQKPDGTIKRLIYATS TLDSGVPKRFSGSRSGSDYSLTISSLESEDFADYYCLQYAIYPLTFGAGTKL ELKR |
| 41 | | HC-CDR1 | GFNIKDTY |
| 42 | | HC-CDR2 | IDPANDNT |
| 43 | | HC-CDR3 | ARAKNLLNYFDY |
| 44 | | LC-CDR1 | QEISGY |
| 45 | | LC-CDR2 | ATS |
| 46 | | LC-CDR3 | LQYAIYPLT |
| 5 | 6 | Chimeric VH 1 | EVQLQQSGAELVKPGASVKLSCTASGFNIKDTYMYWVKQRPEQGLECIGRID PANDNTKYDPKFQGKATITADTSSNTAYVQLASLTSEDTAVYYCARAKNLLN YFDYWGQGTTLTVSSASTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG |
| 7 | 8 | Chimeric VL1 | DIQMTQSPSSLSASLGERVTLSCRASQEISGYLSWLQQKPDGTIKRLIYATS TLDSGVPKRFSGSRSGSDYSLTISSLESEDFADYYCLQYAIYPLTFGAGTKL ELKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC |
| 9 | 10 | Humanized VH 1 | QVQLVQSGAEVKKPGASVKVSCKASGFNIKDTYMYWVRQAPGQGLEWMGRID PANDNTKYAQKFQGRVTITADTSTSTAYMELSSLRSEDTAVYYCARAKNLLN YFDYWGQGTLVTVSS |
| 11 | 12 | Humanized VH 2 | QVQLVQSGAEVKKPGASVKVSCKASGFNIKDTYMYWVRQAPGQGLEWIGRID PANDNTKYAPKFQGRVTITADTSTNTAYMELSSLRSEDTAVYYCARAKNLLN YFDYWGQGTLVTVSS |
| 13 | 14 | Humanized VH3 | EVQLVQSGAEVKKPGASVKVSCKASGFNIKDTYMYWVRQAPGQGLEWMGRID PANDNTKYAQKFQGRVTITADTSTNTAYMELSSLRSEDTAVYYCARAKNLLN YFDYWGQGTLVTVSS |
| 15 | 16 | Humanized VL 1 | DIQMTQSPSSLSASVGDRVTITCRASQEISGYLSWYQQKPGKAPKRLIYATS TLDSGVPSRFSGSGSGTDFTLTISSLQPEDFATYYCLQYAIYPLTFGQGTKL EIKR |
| 17 | 18 | Humanized VL 2 | DIQMTQSPSSLSASVGDRVTITCRASQEISGYLSWLQQKPGKAPKRLIYATS TLQSGVPSRFSGSRSGTDYTLTISSLQPEDFATYYCLQYAIYPLTFGQGTKL EIKR |

TABLE 3-continued

Exemplary anti-PD-L1 antibody sequences.

| SEQ ID NO. AA | DNA | Description | Amino acid sequence (CDR sequences are underlined and bold) |
|---|---|---|---|
| 19 | 20 | Humanized VL 3 | DIQMTQSPSSLSASVGDRVTITCRASQEISGYLSWYQQKPGKAPKRLIYATSTLDSGVPSRFSGSRSGSDYTLTISSLQPEDFATYYCLQYAIYPLTFGQGTKLEIKR |

TABLE 4

Exemplary anti-PD-L1 CDRs under various CDR definitions

| SEQ ID NO | Description | Sequences |
|---|---|---|
| 41 | CDR-H1 | GFNIKDTY |
| 52 | CDR-H1 (Kabat) | DTYMY |
| 53 | CDR-H1 (Chothia) | GFNIKDT |
| 54 | CDR-H1 (AbM) | GFNIKDTYMY |
| 55 | CDR-H1 (Contact) | KDTYMY |
| 42 | CDR-H2 | IDPANDNT |
| 56 | CDR-H2 (Kabat) | RIDPANDNTKYAQKFQG |
| 57 | CDR-H2 (Chothia) | DPANDN |
| 58 | CDR-H2 (AbM) | RIDPANDNTK |
| 59 | CDR-H2 (Contact) | WMGRIDPANDNTK |
| 43 | CDR-H3 | ARAKNLLNYFDY |
| 60 | CDR-H3 (Kabat/Abm/Chothia) | AKNLLNYFDY |
| 61 | CDR-H3 (Contact) | ARAKNLLNYFD |
| 44 | CDR-L1 | QEISGY |
| 62 | CDR-L1 (Kabat/Abm/Chothia) | RASQEISGYLS |
| 63 | CDR-L1 (Contact) | SGYLSWL |
| 45 | CDR-L2 | ATS |
| 64 | CDR-L2 (Kabat/Abm/Chothia) | ATSTLQS |
| 65 | CDR-L2 (Contact) | RLIYATSTLQ |
| 46 | CDR-L3 (Kabat/Abm/Chothia) | LQYAIYPLT |
| 66 | CDR-L3 (Contact) | LQYAIYPL |

In some embodiments, the anti-PD-L1 antibody moiety competes for binding to a target PD-L1 with a second anti-PD-L1 antibody moiety according to any one of the anti-PD-L1 antibody moieties described herein. In some embodiments, the anti-PD-L1 antibody moiety binds to the same, or substantially the same, epitope as the second anti-PD-L1 antibody moiety. In some embodiments, binding of the anti-PD-L1 antibody moiety to the target PD-L1 inhibits binding of the second anti-PD-L1 antibody moiety to PD-L1 by at least about 70% (such as by at least about any one of 75%, 80%, 85%, 90%, 95%, 98% or 99%), or vice versa. In some embodiments, the anti-PD-L1 antibody moiety and the second anti-PD-L1 antibody moiety cross-compete for binding to the target PD-L1, i.e., each of the anti-PD-L1 antibody moieties competes with the other for binding to the target PD-L1.

Anti-PD-L1 scFv

In some embodiments, the anti-PD-L1 antibody moiety comprises an scFv. In some embodiments, the anti-PD-L1 antibody moiety is an scFv. In some embodiments, the anti-PD-L1 scFv has the configuration of (from N-terminus to C-terminus): $V_L$-L-$V_H$, or $V_H$-L-$V_L$, wherein L is a peptide linker. In some embodiments, the anti-PD-L1 scFv is chimeric, human, partially humanized, fully humanized, or semi-synthetic.

In some embodiments, the anti-PD-L1 scFv is engineered to have enhanced thermal stability. In some embodiments, the anti-PD-L1 scFv is engineered to have a melting temperature of about 55-70° C., such as about any one of 55-60, 60-65, or 65-70° C. In some embodiments, the anti-PD-L1 scFv comprises one or more (such as 1, 2, 3, or more) engineered disulfide bonds. In some embodiments, the anti-PD-L1 scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. Other engineered disulfide bonds may be introduced into the anti-PD-L1 scFv by engineering a cysteine in the VH and a cysteine in the VL at suitable positions based on the structure and sequences of the scFv.

In some embodiments, the anti-PD-L1 scFv comprises: i) a $V_H$ comprising an HC-CDR1 comprising the amino acid sequence of SEQ ID NO: 41, an HC-CDR2 comprising the amino acid sequence of SEQ ID NO: 42, and an HC-CDR3 comprising the amino acid sequence of a SEQ ID NO: 43; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 44, an LC-CDR2 comprising the amino acid sequence of SEQ ID NO: 45, and an LC-CDR3 comprising the amino acid sequence of SEQ ID NO: 46; or a variant thereof comprising up to about 5 (such as about any of 1, 2, 3, 4, or 5) amino acid substitutions in the LC-CDR sequences. In some embodiments, the anti-PD-L1 scFv is humanized. In some embodiments, the anti-PD-L1 scFv comprises from the N-terminus to the C-terminus: a $V_H$, an optional peptide linker, and a $V_L$. In some embodiments, the anti-PD-L1 scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the anti-PD-L1 scFv comprises one or more (such as 1, 2, 3, or more) engineered disulfide bonds. In some embodiments, the anti-PD-L1 scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

In some embodiments, the anti-PD-L1 scFv comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 scFv is humanized. In some embodiments, the anti-PD-L1 scFv comprises from the N-terminus to the C-terminus: a $V_H$, an optional peptide linker, and a $V_L$. In some embodiments, the anti-PD-L1 scFv comprises from the N-terminus to the C-terminus: a $V_L$, an optional peptide linker, and a $V_H$. In some embodiments, the scFv comprises a peptide linker comprising the amino acid sequence of SEQ ID NO: 47 or 48. In some embodiments, the anti-PD-L1 scFv comprises one or more (such as 1, 2, 3, or more) engineered disulfide bonds. In some embodiments, the anti-PD-L1 scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

Figure 9:
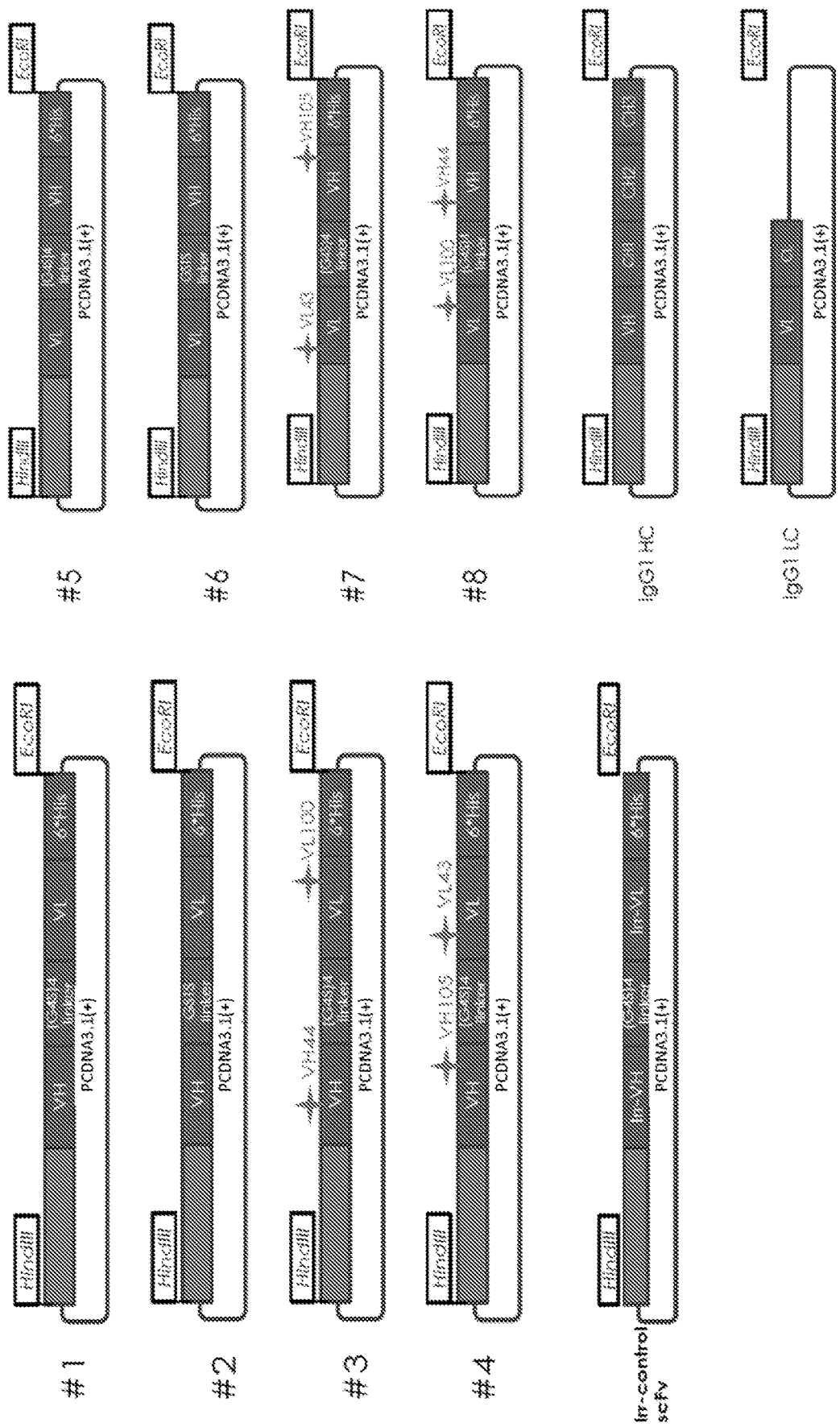
FIG. 9 shows schematic diagrams of the construct designs for anti-hPD-L1 scFvs, the parental humanized IgG1 positive control antibody and a negative control scFv.

In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the anti-PD-L1 scFv comprises a His tag. In some embodiments, the anti-PD-L1 scFv comprises a His tag fused to the C-terminus of the anti-PD-L1 scFv moiety. In some embodiments, the anti-PD-L1 scFv comprises GGGGSHHHHHH (SEQ ID NO: 51). Exemplary anti-PD-L1 scFvs are illustrated in FIG. 9. Exemplary anti-PD-L1 scFv sequences are shown in Table 5.

TABLE 5

Exemplary anti-PD-L1 scFv sequences.

| SEQ ID NO. | | | Amino acid Sequence |
|---|---|---|---|
| AA | DNA | Description | (CDR sequences are underlined and bold) |
| 25 | 26 | anti-human PD-L1 scFv variant 1 | QVQLVQSGAEVKKPGASVKVSCKASGFNIKDTYMYWVRQAPGQGLEWMGRID PANDNTKYAQKFQGRVTITADTSTSTAYMELSSLRSEDTAVYYCARAKNLLN YFDYWGQGTLVTVSSGGGGSGGGGSGGGGSGGGGSDIQMTQSPSSLSASVGD RVTITCRASQEISGYLSWLQQKPGKAPKRLIYATSTLQSGVPSRFSGSRSGT DYTLTISSLQPEDFATYYCLQYAIYPLTFGQGTKLEIKR |
| 27 | 28 | anti-human PD-L1 scFv variant 2 | QVQLVQSGAEVKKPGASVKVSCKASGFNIKDTYMYWVRQAPGQGLEWMGRID PANDNTKYAQKFQGRVTITADTSTSTAYMELSSLRSEDTAVYYCARAKNLLN YFDYWGQGTLVTVSSGSTSGSGKPGSGEGSTKGDIQMTQSPSSLSASVGDRV TITCRASQEISGYLSWLQQKPGKAPKRLIYATSTLQSGVPSRFSGSRSGTDY TLTISSLQPEDFATYYCLQYAIYPLTFGQGTKLEIKR |
| 29 | 30 | anti-human PD-L1 scFv variant 3 | QVQLVQSGAEVKKPGASVKVSCKASGFNIKDTYMYWVRQAPGQCLEWMGRID PANDNTKYAQKFQGRVTITADTSTSTAYMELSSLRSEDTAVYYCARAKNLLN YFDYWGQGTLVTVSSGGGGSGGGGSGGGGSGGGGSDIQMTQSPSSLSASVGD RVTITCRASQEISGYLSWLQQKPGKAPKRLIYATSTLQSGVPSRFSGSRSGT DYTLTISSLQPEDFATYYCLQYAIYPLTFGCGTKLEIKR |
| 31 | 32 | anti-human PD-L1 scFv variant 4 | QVQLVQSGAEVKKPGASVKVSCKASGFNIKDTYMYWVRQAPGQGLEWMGRID PANDNTKYAQKFQGRVTITADTSTSTAYMELSSLRSEDTAVYYCARAKNLLN YFDYWGCGTLVTVSSGGGGSGGGGSGGGGSGGGGSDIQMTQSPSSLSASVGD RVTITCRASQEISGYLSWLQQKPGKCPKRLIYATSTLQSGVPSRFSGSRSGT DYTLTISSLQPEDFATYYCLQYAIYPLTFGQGTKLEIKR |

TABLE 5-continued

Exemplary anti-PD-L1 scFv sequences.

| SEQ ID NO. AA | DNA | Description | Amino acid Sequence (CDR sequences are underlined and bold) |
|---|---|---|---|
| 33 | 34 | anti-human PD-L1 scFv variant 5 | DIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGQGTKLEIKRGGGGSGGGGSGGGGSGGGGSQVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGQGTLVTVSS |
| 35 | 36 | anti-human PD-L1 scFv variant 6 | DIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGQGTKLEIKRGSTSGSGKPGSGEGSTKGQVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGQGTLVTVSS |
| 37 | 38 | anti-human PD-L1 scFv variant 7 | DIQMTQSPSSLSASVGDRVTITCRASQEISGYLSWLQQKPGKCPKRLIYATSTLQSGVPSRFSGSRSGTDYTLTISSLQPEDFATYYCLQYAIYPLTFGQGTKLEIKRGGGGSGGGGSGGGGSGGGGSQVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGCGTLVTVSS |
| 39 | 40 | anti-human PD-L1 scFv variant 8 | DIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGCGTKLEIKRGGGGSGGGGSGGGGSGGGGSQVQLVQSGAEVKKPGASVKVSCKASGFNIKDTYMYWVRQAPGQCLEWMGRIDPANDNTKYAQKFQGRVTITADTSTSTAYMELSSLRSEDTAVYYCARAKNLLNYFDYWGQGTLVTVSS |

Andi-PD-L1 scFv-Fc

In some embodiments, the anti-PD-L1 antibody moiety is an anti-PD-L1 scFv according to any one of the anti-PD-L1 scFvs described herein fused to an Fc fragment. In some embodiments, the anti-PD-L1 antibody moiety is fused to an Fc fragment via a peptide linker. The anti-PD-L1 antibody moiety may comprise any of the Fc fragments described in the "Antibody moieties" section above. In some embodiments, the Fc fragment is a human IgG1 Fc fragment. In some embodiments, the Fc fragment comprises one or more mutations to increase clearance or decrease half-life. For example, the Fc fragment may have H310A and/or H435Q mutations, wherein the amino acid positions are based on the Kabat numbering system.

In some embodiments, each chain of the Fc fragment is fused to the same entity. In some embodiments, the anti-PD-L1 scFv-Fc comprises two identical anti-PD-L1 scFvs described herein, each fused with one chain of the Fc fragment. In some embodiments, the anti-PD-L1 scFv-Fc is a homodimer. In some embodiments, the anti-PD-L1 scFv-Fc is a heterodimer.

In some embodiments, the anti-PD-L1 scFv-Fc comprises the amino acid sequence of SEQ ID NO: 21 or 23, or a variant thereof having at least about 80% (such as at least about any one of 80%, 85%, 90%, 95%, 96%, 97%, 98%, or 99%) sequence identity to the amino acid sequence of SEQ ID NO: 21 or 23. Exemplary anti-PD-L1 scFv-Fc sequences are shown in Table 6.

TABLE 6

Exemplary anti-PD-L1 scFv-Fc sequences.

| SEQ ID NO. AA | DNA | Description | Amino acid Sequence (CDR sequences are underlined and bold) |
|---|---|---|---|
| 21 | 22 | hPD-L1 scFv-hFc wt | QVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGQGTLVTVSSGSTSGSGKPGSGEGSTKGDIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGQGTKLEIKRDKTHTCPPCPAPELLGGPSVFLFPPKPKDTLMISRTPEVTCVVVDVSHEDPEVKFNWYVDGVEVHNAKTKPREEQYNSTYRVVSVLIVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| 23 | 24 | hPD-L1 scFv-hFc Mt | QVQLVQSGAEVKKPGASVKVSCKASGFNIKDTYMYWVRQAPGQGLEWMGRIDPANDNTKYAQKFQGRVTITADTSTSTAYMELSSLRSEDTAVYYCARAKNLLNYFDYWGQGTLVTVSSGSTSGSGKPGSGEGSTKGDIQMTQSPSSLSASVGDRVTITCRASQEISGYLSWLQQKPGKAPKRLIYATSTLQSGVPSRFSGSRSGTDYTLTISSLQPEDFATYYCLQYAIYPLTFGQGTKLEIKRDKTHTCPPCPAPELLGGPSV |

TABLE 6-continued

Exemplary anti-PD-L1 scFv-Fc sequences.

| SEQ ID NO. | | | Amino acid Sequence |
|---|---|---|---|
| AA | DNA | Description | (CDR sequences are underlined and bold) |
| | | | FLFPPKPKDTLMISRTPEVTCVVVDVSHEDPEVKFNWYVDGVEVHNAKTKPRE
EQYNSTYRVVSVLTVLAQDWLNGKEYKCKVSNKALPAPIEKTISKAKGQPREP
QVYTLPPSRDELTKNQVSLTCLVKGFYPSDIAVEWESNGQPENNYKTTPPVLD
SDGSFFLYSKLTVDKSRWQQGNVFSCSVMHEALHNQYTQKSLSLSPG |

Anti-PD-L1 Imaging Agent

Any one of the anti-PD-L1 antibody moieties described herein may be incorporated in an imaging agent for detection of PD-L1. The features described herein in this section regarding anti-PD-L1 antibody agents may be combined with the features described in the section "Imaging agents" above in any suitable combination.

In some embodiments, there is provided an imaging agent comprising any one of the anti-PD-L1 antibody moieties described herein, wherein the antibody moiety is labeled with a radionuclide. In some embodiments, the radionuclide is selected from the group consisting of $^{62}$Cu, $^{64}$Cu, $^{67}$Cu, $^{18}$F, $^{67}$Ga, $^{68}$Ga, $^{111}$In, $^{177}$Lu, $^{86}$Y, $^{90}$Y, and $^{89}$Zr. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided an imaging agent comprising any one of the isolated anti-PD-L1 antibody agents described herein, wherein the anti-PD-L1 antibody moiety is labeled with a radionuclide. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided an imaging agent comprising an anti-PD-L1 antibody moiety labeled with a radionuclide, wherein the anti-PD-L1 antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the radionuclide is selected from the group consisting of $^{64}$Cu, $^{18}$F, $^{67}$C, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided an imaging agent comprising an anti-PD-L1 scFv labeled with a radionuclide, wherein the anti-PD-L1 scFv comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided an imaging agent comprising an anti-PD-L1 antibody moiety labeled with a radionuclide, wherein the anti-PD-L1 antibody moiety is an anti-PD-L1 scFv fused to an Fc fragment, wherein the anti-PD-L1 antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the anti-PD-L1 antibody moiety is conjugated to a chelating compound that chelates the radionuclide. In some embodiments, the chelating compound is NOTA, DOTA or derivatives thereof.

In some embodiments, there is provided an imaging agent comprising an anti-PD-L1 antibody moiety conjugated to NOTA that chelates a radionuclide (e.g., $^{68}$Ga), wherein the anti-PD-L1 antibody moiety comprises a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}$Cu, $^{18}$F, $^{67}$Ga, $^{68}$Ga, $^{111}$In $^{177}$Lu, $^{90}$Y, $^{89}$Zr, $^{61}$Cu, $^{62}$Cu, $^{67}$Cu, $^{19}$F, $^{66}$C, $^{72}$Ga, $^{44}$Sc, $^{47}$Sc, $^{86}$Y, $^{88}$Y and $^{45}$Ti.

In some embodiments, there is provided an imaging agent comprising an anti-PD-L1 antibody moiety conjugated to NOTA that chelates a radionuclide (e.g., $^{68}$Ga), wherein the anti-PD-L1 antibody moiety is an anti-PD-L1 scFv fused to an Fc fragment, and wherein the anti-PD-L1 antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions. In some embodiments, the anti-PD-L1 antibody moiety comprises: a $V_H$ comprising the amino acid sequence of any one of SEQ ID NOs: 1, 5, 9, 11, and 13, or a variant thereof having at least about 80% (such as at least about any one of 80%, 85%, 90%, 95%, 96%, 97%, 98%, or 99%) sequence identity to the amino acid sequence of any one of SEQ ID NOs: 1, 5, 9, 11, and 13; and a $V_L$ comprising the amino acid sequence of any one of SEQ ID NOs: 3, 7, 15, 17 and 19, or a variant thereof having at least about 80% (such as at least about any one of 80%, 85%, 90%, 95%, 96%, 97%, 98%, or 99%) sequence identity to the amino acid sequence of any one of SEQ ID NOs: 3, 7, 15, 17 and 19. In some embodiments, the anti-PD-L1 antibody moiety is humanized. In some embodiments, the anti-PD-L1 scFv comprises a first engineered cysteine residue at position 44 of $V_1$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. In some embodiments, the Fc fragment is an IgG1 Fc fragment. In some embodiments, the Fc fragment has H310A and H435Q mutations, wherein the amino acid positions are based on the Kabat numbering system. In some embodiments, the anti-PD-L1 scFv comprises the amino acid sequence of any one of SEQ ID NOs: 25, 27, 29, 31, 33, 35, 37 and 39, or a variant thereof having at least about 80% (such as at least about any one of 80%, 85%, 90%, 95%, 96%, 97%, 98%, or 99%) sequence identity to the amino acid sequence of any one of SEQ ID NOs: 25, 27, 29, 31, 33, 35, 37 and 39. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti.

PD-1

The PD-1/PD-L1 Pathway and Anti-PD Immunotherapy

The gene encoding programmed cell death 1 (PD-1) was first isolated from a murine T cell hybridoma and a hematopoietic progenitor cell line undergoing classic apoptosis in 1992 (Ishida Y, et al. *The EMBO journal* 1992; 11:3887-3895). Structurally, as a CD28 and CTLA4 homologue, PD-1 is a type I transmembrane protein and belongs to the Ig superfamily (Sharpe A H and Freeman G J. *Nature Reviews Immunology* 2002; 2:116-126). The critical role of PD-1 in negatively modulating T cell responses and maintaining peripheral tolerance was shown by PD-1 gene ablation studies using different mouse models. PD-1-deficient mice in C57BL/6 background develop lupus-like autoimmune diseases due to enhanced proliferation of PD-1 deficient T cells against allogeneic antigen (Nishimura H et al. *Immunity* 1999; 11:141-151). In BALB/c, but not in immune-deficient BALB/c RAG2-/- background, PD-1 knockout mice develop dilated cardiomyopathy and suffered sudden death from congestive heart failure (Nishimura H et al. *Science* 2001; 291:319-322). One of the major contributing causes was later identified to be the generation of high-titer autoantibodies against the heart-specific protein cardiac troponin I (Okazaki T, et al. *Nature medicine* 2003; 9:1477-1483). In the NOD (non-obese diabetic) background, PD-1 deficiency leads to early onset of type I diabetes due to the accelerated islet-specific T cell expansion and infiltration into the pancreas islets (Yantha J et al. *Diabetes* 2010; 59:2588-2596). Overall, the PD-1 molecule acts as an inhibitory receptor involved in peripheral tolerance (Nishimura H, Honjo T. *Trends in immunology* 2001; 22:265-268). Unlike CTLA-4, the immunoreceptor tyrosine-based switch motif (ITSM) in PD-1, but not the nearby ITIM domain located in the cytoplasmic tail of PD-1, recruits SHP-2 phosphatase and reverses activation-induced phosphorylation after TCR signaling (Ishida Y, et al. *The EMBO journal* 1992; 11:3887-3895).

Several studies contributed to the discovery of the molecules that interact with PD-1. In 1999, the B7 homolog 1 (B7H1, also referred to as programmed death ligand-1 [PD-L1] in the later literature) was identified as a 290-amino-acid type I transmembrane glycoprotein belonging to the B7-CD28 family of the immunoglobulin superfamily that served as a negative regulator of human T cell response in vitro (Dong H et al. *Nature medicine* 1999; 5:1365-1369). One year later, it was shown that PD-L1 is a binding and functional counterpart of PD-1 (Freeman G J et al. *The Journal of experimental medicine* 2000; 192:1027-1034). It was later demonstrated that PD-L1 deficient mice were prone to autoimmune conditions (Dong H et al. *Immunity* 2004; 20:327-336). Notably, although the mRNAs for PD-1 and PD-L1 are expressed with broad spectrum in many cell types, both are inducible molecules as their expression patterns are strictly controlled by posttranscriptional regulation. PD-1 protein is not detectable on resting T cells, but is found on the cell surface within 24 hours of T-cell activation (Keir M E et al. *Annual review of immunology* 2008; 26:677-704). Under normal physiological conditions, PD-L1 protein is only expressed in the peripheral tissues, such as the tonsil, placenta, and a small fraction of macrophage-like cells in the lung and liver (Dong H et al. *Nature medicine* 2002; 8:793-800; Petroff M G et al. *Placenta* 2002; 23 Suppl A:S95-101). Extrinsic induction of PD-L1 is largely mediated by proinflammatory cytokines, such as interferon γ (IFN-γ), which indicates that PD-1/PD-L1 interaction plays an important role in the control of inflammatory response in the peripheral tissues (Zou W, Chen L. *Nature reviews Immunology* 2008; 8:467-477).

In addition to PD-L1, another PD-1 ligand called B7-DC (also known as PD-L2) was also independently identified by two laboratories (Tseng S Y et al. *The Journal of experimental medicine* 2001; 193:839-846; Latchman Y, et al. *Nature immunology* 2001; 2:261-268). PD-L2 was found to be selectively expressed on dendritic cells (DCs) and also negatively regulate T cell response by binding to PD-1. Recently, PD-L2 was also found to interact with repulsive guidance molecule family member b (RGMb), a molecule that is highly enriched in lung macrophages and may be required for induction of respiratory tolerance (Xiao Y, et al. *The Journal of experimental medicine* 2014; 211:943-959). Interestingly, PD-L1 was also found to have another receptor CD80 on activated T cells to deliver inhibitory signal, which may also contribute to the formation of T cell tolerance in vivo (Butte M J et al. *Immunity* 2007; 27:111-122; Park J J et al. *Blood* 2010; 116:1291-1298). Currently, at least five interacting molecules are known to be involved in the PD network. Thus, the original PD-1/PD-L1 pathway is renamed to the more suitable "PD pathway." The presence of two ligands (PD-L1 and PD-L2) for PD-1 and two inhibitory receptors (PD-1 and CD80) for PD-L1 suggests that neither PD-1 blockade nor PD-L1 blockade would completely disrupt the PD pathway. Complete abrogation of the PD inhibitory pathway may require a combination strategy targeting both molecules.

The crucial function of the PD pathway in modulating the activity of T cells in the peripheral tissues in an inflammatory response to infection and in limiting autoimmunity appears to be hijacked by tumor cells and by viruses during chronic viral infections. PD-L1 is overexpressed on many freshly isolated human tumors from multiple tissue origins (Dong et al. *Nature Medicine* 2002; 8:793-800; Romano et al. *Journal for Immunotherapy of Cancer* 2015; 3:15; Hirano et al. *Cancer Research* 2005; 65:1089-1096). The expression of PD-L1 has been correlated with the progression and poor prognosis of certain types of human cancers (Wang et al. *European journal of surgical oncology: the journal of the European Society of Surgical Oncology and the British Association of Surgical Oncology* 2015; 41:450-456; Cierna et al. *Annals of oncology: official journal of the European Society for Medical Oncology/ESMO* 2016; 27:300-305; Gandini et al. *Critical reviews in oncology/hematology* 2016; 100:88-98; Thierauf et al. *Melanoma research* 2015; 25:503-509; Taube et al. *Clinical cancer research: an official journal of the American Association for Cancer Research* 2014; 20:5064-5074). During chronic viral infections, PD-L1 is persistently expressed on many tissues, while PD-1 is up-regulated on virus-specific CTLs (Yao et al. *Trends in molecular medicine* 2006; 12:244-246). Tumor- or virus-induced PD-L1 may utilize multiple mechanisms to facilitate the evasion of host immune surveillance, including T cell anergy, apoptosis, exhaustion, IL-10 production, DC suppression, as well as Treg induction and expansion (Zou et al. *Nature reviews Immunology* 2008; 8:467-477).

The PD pathway mediated escape of tumor immunity could be viewed as an "adaptive resistance" model (Chen et al. *The Journal of clinical investigation* 2015; 125:3384-3391; Yao et al. *European journal of immunology* 2013; 43:576-579). Specifically, activated tumor-specific T cells reach the tumor sites and become tumor-infiltrating lymphocytes (TILs). Upon recognition of the cognate antigen, TILs produce IFN-γ, which induces PD-L1 expression in many cell types in the tumor microenvironment, including DCs, macrophages, neutrophils, and B lymphocytes. Upon binding to PD-1, PD-L1 delivers a suppressive signal to T cells and an anti-apoptotic signal to tumor cells, leading to T cell dysfunction and tumor survival (Taube et al. *Science translational medicine* 2012; 4:127ra137; Spranger et al. *Science translational medicine* 2013; 5:200ra116). This model is not only supported by IHC-based observations that cell surface PD-L1 expression is detected only in cells that are adjacent to T cells, but also supported by studies showing a strong correlation between PD-L1 expression in tumor sites and the presence of TILs (Gandini et al. *Critical reviews in oncology/hematology* 2016; 100:88-98; Taube et al. *Science translational medicine* 2012; 4:127ra137), as well as the demonstration of IFN-γ as a major PD-L1 inducer in vivo in mouse tumor models (Dong et al. *Nature medicine* 2002; 8:793-800). The PD pathway mediated adaptive resistance hypothesis supports the observation that the majority of the PD-L1+ tumors can escape immune destruction even under strong anti-tumor immunity.

Based on the "adaptive resistance" model, immunotherapies targeting the PD pathway are designed to block the interaction of PD-1 and PD-L1, thus preventing the resistance to anti-tumor immunity. Even though the discovery of PD-1 did not lead to its application in anti-tumor therapies until the abundant expression of PD-L1 was discovered in tumors, linking the PD pathway with cancer treatment (Dong et al. *Nature Medicine* 1999; 5:1365-1369), by now, the FDA has already approved two PD-1 monoclonal antibodies for treating human cancers. These are OPDIVO® (also known as nivolumab, MDX-1106, BMS-936558 and ONO-4538) developed by Bristol-Myers Squibb (68), and KEYTRUDA® (also known as pembrolizumab, lambrolizumab and MK-3475) developed by Merck (69). Multiple monoclonal antibodies targeting either PD-1 or PD-L1 are under intense evaluations in hundreds of clinical trials involving thousands of patients. Anti-PD therapy has generated significant clinical benefits including remarkable regression of tumors and substantial extension of survival rate. Since anti-PD therapy targets tumor-induced immune defects through immune-modulation in the tumor sites, it offers durable efficacy, tolerable toxicity and a broad spectrum of cancer indications[59] The clinical success of anti-PD immunotherapy further validates the effectiveness of PD pathway blockade as a unique category of cancer therapy that is distinct from personalized or tumor type-specific therapies. By targeting tumors that have exploited defined immune checkpoint pathway to escape immune surveillance, anti-PD immunotherapy has taken center stage in immunotherapies for human cancers, and especially solid tumors.

PD-L1 Expression at Tumor Site as a Biomarker to Predict Efficacy of Anti-PD Immunotherapy Multiple solid tumor types show positive correlation between response rate to anti-PD immunotherapy and PD-L1 expression level within the tumor, including melanoma, RCC, NSCLC, colorectal cancer, as well as several hematologic malignancies, such as classical Hodgkin's lymphoma. In the melanoma clinical trials, PD-L1 overexpression detected by IHC was in approximately 45%-75% of the samples. In the nivolumab study, 45% of patients were positive for PD-L1 expression based on a 5% cutoff using the 28-8 antibody. The response rate for PD-L1-positive patients was 44%, compared to 17% for PD-L1-negative patients. PD-L1-positive melanoma patients treated with nivolumab had an OS of 21.1 months and a PFS of 9.1 months, as compared to 12.5 months and 2 months in PD-L1 negative patients, respectively. Pembrolizumab (anti-PD-1) has also been studied in advanced melanoma utilizing an IHC cutoff of 1%. PD-L1-positive patients (77%) had an ORR of 51%, while PD-L1-negative patients had an ORR of 6%. PD-L1-positive patients treated with pembrolizumab had a PFS of 12 months and a 1-year OS rate of 84%, while PD-L1-negative patients had a PFS of 3 months and a 1-year OS of 69%.

A similar trend was seen in NSCLC, where PD-L1-positive patients seemed to preferentially benefit from PD-1/PD-L1-directed therapy. Nivolumab was studied in patients with refractory NSCLC, and PD-L1 IHC was performed using a DAKO IHC assay with a 5% cutoff. On the basis of these criteria, 60% of patients were classified as positive for PD-L1, and the response rate in PD-L1-positive patients was 67% compared with 0% in PD-L1-negative patients. Pembrolizumab has also been investigated in NSCLC, utilizing a unique 50% IHC cutoff for PD-L1 expression using an unreported assay. On the basis of this cutoff, 25% of tumors were positive for PD-L1 and, at 6 months, PD-L1-positive patients had a 67% immune-related ORR (irORR), a 67% PFS rate, and a 89% OS rate compared to PD-L1-negative patients who had a 0% irORR, a 11% PFS rate, and a 33% OS rate. MPDL3280A, an anti-PD-L1 antibody, has also been studied in NSCLC utilizing a proprietary IHC platform with 0-3+ grading (3+ for >10% cells, 2+ for >5% cells, 0-1 for <5% cells). NSCLC patients with a PD-L1 expression score of 3+ had an 83% response rate, compared with 46% in patients with a score of either 2+ or 3+. Patients with 1+/2+/3+ PD-L1 expression had a 31% ORR.

PD-L1 IHC as a predictive biomarker has also been assessed in clinical trials involving multiple histologies. The nivolumab phase I study included patients with melanoma, RCC, NSCLC, metastatic colorectal cancer (mCRC), and metastatic castration-resistant prostate cancer (mCRPC). PD-L1 was detected by the 5H1 antibody utilizing a 5% threshold, and 60% of tumors were positive by this criterion. Patients with PD-L1-positive tumors had a 36% response rate, while patients with PD-L1 negative tumors had a 0% ORR. MPDL3280A has been studied in patients with melanoma, RCC, NSCLC, mCRC, and gastric cancer utilizing a proprietary PD-L1 IHC platform. PD-L1-positive patients had a 39% response rate, while PD-L1-negative patients had a 13% response rate.

Data from these clinical trials appears to suggest that patients with higher levels of PD-L1 according to IHC appeared to have superior responses to PD-1/PD-L1-directed therapy. However, relatively less is known about the nature of responses or survival outcomes in PDL1-negative patients treated with anti-PD immunotherapy. Initial evaluations suggest that select PD-L1-negative patients with melanoma can still obtain durable responses to anti-PD-1/PD-L1 therapy, while response in PD-L1-negative NSCLC patients are rare. If this trend is reproduced in larger trials, it may represent a fundamental difference in the immunobiology between the two different tumor types, or it may represent a technical issue with IHC in different tissue types. In a phase I clinical trial for MPDL3280A in metastatic urothelial bladder cancer, PD-L1-positive patients had a 52% ORR at 12 weeks, compared with 11% in PD-L1-negative patients. Therefore, the depth and duration of responses in PD-L1-negative patients remains to be seen.

V. Antibodies

Also provided herein are antibodies that specifically recognize an immune checkpoint ligand, such as PD-L1 and PD-L1 like ligands. Such antibodies and antibody moieties derived therefrom can be incorporated into the methods and imaging agents described in the sections above. Suitable antibody moieties include, but are not limited to, scFv, Fab, and scFv fused to an Fc fragment (also referred herein as "scFv-Fc"). The antibody moieties (including the anti-PD-L1 antibody agents) described herein may have any one or more of the features described in the sections a)-h) below.

In some embodiments, the antibody moiety comprises an scFv. In some embodiments, the antibody moiety is an scFv. In some embodiments, the scFv has the configuration of (from N-terminus to C-terminus): $V_L$-L-$V_H$, or $V_H$-L-$V_L$, wherein L is a peptide linker. In some embodiments, the scFv is chimeric, human, partially humanized, fully humanized, or semi-synthetic.

In some embodiments, the scFv is engineered to have enhanced thermal stability. In some embodiments, the scFv is engineered to have a melting temperature of about 55-70° C., such as about any one of 55-60, 60-65, or 65-70° C. In some embodiments, the scFv comprises one or more (such as 1, 2, 3, or more) engineered disulfide bonds. In some embodiments, the scFv comprises a first engineered cysteine residue at position 44 of $V_H$ and a second engineered cysteine residue at position 100 of $V_L$, and/or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system. Other engineered disulfide bonds may be introduced into the scFv by engineering a cysteine in the VH and a cysteine in the VL at suitable positions based on the structure and sequences of the scFv.

In some embodiments, the antibody moiety comprises an Fc fragment. In some embodiments, the antibody moiety is an scFv fused to an Fc fragment. In some embodiments, the antibody moiety comprises a scFv fused to an Fc fragment via a peptide linker. In some embodiments, the Fc fragment is a human IgG1 Fc fragment. In some embodiments, the Fc fragment comprises one or more mutations to increase clearance or decrease half-life. For example, the Fc fragment may have H310A and/or H435Q mutations, wherein the amino acid positions are based on the Kabat numbering system.

In some embodiments, the Fc fragment comprises an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In some embodiments, the fusion protein comprises an Fc fragment comprising a hinge region. In some embodiments, the Fc fragment of the fusion protein starts at the hinge region and extends to the C-terminus of the IgG heavy chain. In some embodiments, the fusion protein comprises an Fc fragment that does not comprise the hinge region.

In some embodiments, the antibody moiety comprises an Fc fragment selected from the group consisting of Fc fragments from IgG, IgA, IgD, IgE, IgM, and combinations and hybrids thereof. In some embodiments, the Fc fragment is derived from a human IgG. In some embodiments, the Fc fragment comprises the Fc region of human IgG1, IgG2, IgG3, IgG4, or a combination or hybrid IgG. In some embodiments, the Fc fragment is an IgG1 Fc fragment. In some embodiments, the Fc fragment comprises the CH2 and CH3 domains of IgG1. In some embodiments, the Fc fragment is an IgG4 Fc fragment. In some embodiments, the Fc fragment comprises the CH2 and CH3 domains of IgG4. IgG4 Fc is known to exhibit less effector activity than IgG1 Fc, and thus may be desirable for some applications. In some embodiments, the Fc fragment is derived from of a mouse immunoglobulin.

In some embodiments, the IgG CH2 domain starts at Ala231. In some embodiments, the CH3 domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

In some embodiments, each chain of the Fc fragment is fused to the same antibody moiety. In some embodiments, the scFv-Fc comprises two identical scFvs described herein, each fused with one chain of the Fc fragment. In some embodiments, the scFv-Fc is a homodimer.

In some embodiments, the scFv-Fc comprises two different scFvs, each fused with one chain of the Fc fragment. In some embodiments, the scFv-Fc is a heterodimer. Heterodimerization of non-identical polypeptides in the scFv-Fc can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 201 1/0287009 and PCT/US2012/059810, hereby incorporated by reference in their entireties. This technology was developed by introducing a "knob" (or a protuberance) by replacing a small amino acid residue with a large one in the CH3 domain of one Fc and introducing a "hole" (or a cavity) in the CH3 domain of the other Fc by replacing one or more large amino acid residues with smaller ones. In some embodiments, one chain of the Fc fragment in the fusion protein comprises a knob, and the second chain of the Fc fragment comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the CH3 domain for generating the hole include without limitation the T366S, L368A, F405A, Y407A, Y407T and Y407V substitutions. In certain embodiments, the knob comprises T366W substitution, and the hole comprises the T366S/L368A/Y 407V substitutions. It is understood that other modifications to the Fc region known in the art that facilitate heterodimerization are also contemplated and encompassed by the instant application.

Other scFv-Fc variants (including variants of isolated anti-PD-L1 scFv-Fc, e.g., a full-length anti-PD-L1 antibody variants) comprising any of the variants described herein (e.g., Fc variants, effector function variants, glycosylation variants, cysteine engineered variants), or combinations thereof, are contemplated.

a) Antibody Affinity

Binding specificity of the antibody moieties can be determined experimentally by methods known in the art. Such methods comprise, but are not limited to Western blots, ELISA-, RIA-, ECL-, IRMA-, EIA-, BIACORE™-tests and peptide scans.

In some embodiments, the $K_D$ of the binding between the antibody moiety and the immune checkpoint ligand (e.g., PD-L1 or a PD-L1 like ligand) is about $10^{-7}$ M to about $10^{-12}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-7}$ M to about $10^{-11}$ M, about $10^{-8}$ M to about $10^{-11}$ M, about $10^{-9}$ M to about $10^{-11}$ M, about $10^{-7}$ M to about $10^{-10}$ M, about $10^{-8}$ M to about $10^{-10}$ M, or about $10^{-7}$ M to about $10^{-9}$ M. In some embodiments, the $K_D$ of the binding between the antibody moiety and the immune checkpoint ligand (e.g., PD-L1 or a PD-L1 like ligand) is stronger than about any one of $10^{-7}$ M, $10^{-8}$ M, $10^{-9}$ M, $10^{-10}$ M, $10^{-11}$ M, or $10^{-12}$ M. In some embodiments, the immune checkpoint ligand is human immune checkpoint ligand (e.g., human PD-L1 or a PD-L1 like ligand). In some embodiments, the immune checkpoint ligand is cynomolgus monkey immune checkpoint ligand (e.g., cynomolgus monkey PD-L1 or a PD-L1 like ligand). In some embodiments, the antibody moiety specifically recognizes an epitope in the extracellular domain of the immune checkpoint ligand, such as amino acids 19-238 of SEQ ID NO: 4.

In some embodiments, the $K_{on}$ of the binding between the antibody moiety and the immune checkpoint ligand (e.g., PD-L1 or a PD-L1 like ligand) is about $10^3$ M$^{-1}$s$^{-1}$ to about $10^8$ M$^{-1}$s$^{-1}$, about $10^3$ M$^{-1}$s$^{-1}$ to about $10^4$ M$^{-1}$s$^{-1}$, about $10^4$ M$^{-1}$s$^{-1}$ to about $10^5$ M$^{-1}$s$^{-1}$, about $10^5$ M$^{-1}$s$^{-1}$ to about $10^6$ M$^{-1}$s$^{-1}$, about $10^6$ M$^{-1}$s$^{-1}$ to about $10^7$ M$^{-1}$s$^{-1}$, or about $10^7$ M$^{-1}$s$^{-1}$ to about $10^8$ M$^{-1}$s$^{-1}$. In some embodiments, the $K_{on}$ of the binding between the antibody moiety and the immune checkpoint ligand (e.g., PD-L1 or a PD-L1 like ligand) is about $10^3$ M$^{-1}$s$^{-1}$ to about $10^5$ M$^{-1}$s$^{-1}$, about $10^4$ M$^{-1}$s$^{-1}$ to about $10^6$ M$^{-1}$s$^{-1}$, about $10^5$ M$^{-1}$s$^{-1}$ to about $10^7$ M$^{-1}$s$^{-1}$, about $10^6$ M$^{-1}$s$^{-1}$ to about $10^8$ M$^{-1}$s$^{-1}$, about $10^4$ M$^{-1}$s$^{-1}$ to about $10^7$ M$^{-1}$s$^{-1}$, or about $10^5$ M$^{-1}$s$^{-1}$ to about $10^8$ M$^{-1}$s$^{-1}$. In some embodiments, the $K_{on}$ of the binding between the antibody moiety and the immune checkpoint ligand (e.g., PD-L1 or a PD-L1 like ligand) is no more than about any one of $10^3$ M$^{-1}$s$^{-1}$, $10^4$ M$^{-1}$s$^{-1}$, $10^5$ M$^{-1}$s$^{-1}$, $10^6$ M$^{-1}$s$^{-1}$, $10^7$ M$^{-1}$s$^{-1}$ or $10^8$ M$^{-1}$s$^{-1}$.

In some embodiments, the $K_{off}$ of the binding between the antibody moiety and the immune checkpoint ligand (e.g., PD-L1 or a PD-L1 like ligand) is about $1$ s$^{-1}$ to about $10^{-6}$ s$^{-1}$, about $1$ s$^{-1}$ to about $10^{-2}$ s$^{-1}$ about $10^{-2}$ s$^{-1}$ to about $10^{-3}$ s$^{-1}$, about $10^{-3}$ s$^{-1}$ to about $10^{-4}$ s$^{-1}$, about $10^{-4}$ s$^{-1}$ to about $10^{-5}$ s$^{-1}$, about $10^{-5}$ s$^{-1}$ to about $10^{-6}$ s$^{-1}$, about $1$ s$^{-1}$ to about $10^{-5}$ s$^{-1}$, about $10^{-2}$ s$^{-1}$ to about $10^{-6}$ s$^{-1}$, about $10^{-3}$ s$^{-1}$ to about $10^{-6}$ s$^{-1}$, about $10^{-4}$ s$^{-1}$ to about $10^{-6}$ s$^{-1}$, about $10^{-2}$ s$^{-1}$ to about $10^{-5}$ s$^{-1}$, or about $10^{-3}$ s$^{-1}$ to about $10^{-5}$ s$^{-1}$. In some embodiments, the $K_{off}$ of the binding between the antibody moiety and the immune checkpoint ligand (e.g., PD-L1 or a PD-L1 like ligand) is at least about any one of $1$ s$^{-1}$, $10^{-2}$ s$^{-1}$, $10^{-3}$ s$^{-1}$, $10^{-4}$ s$^{-1}$, $10^{-5}$ s$^{-1}$ or $10^{-6}$ s$^{-1}$.

b) Chimeric or Humanized Antibodies

In some embodiments, the antibody moiety is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In some embodiments, a chimeric antibody comprises a non-human variable region (e.g., a variable region derived from mouse) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); Framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

c) Human Antibodies

In some embodiments, the antibody moiety is a human antibody (known as human domain antibody, or human DAb). Human antibodies can be produced using various techniques known in the art. Human antibodies are described generally in van Dijk and van de Winkel, *Curr. Opin. Pharmacol.* 5: 368-74 (2001), Lonberg, *Curr. Opin. Immunol.* 20:450-459 (2008), and Chen, *Mol. Immunol.* 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991)). Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, *Methods and Findings in Experimental and Clinical Pharmacology,* 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

d) Library-Derived Antibodies

The antibody moieties may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N J, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N J, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

e) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

f) Glycosylation Variants

In some embodiments, the antibody moiety is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody moiety comprises an Fc region (e.g., scFv-Fc), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antibody moiety may be made in order to create antibody variants with certain improved properties.

In some embodiments, the antibody moiety has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

In some embodiments, the antibody moiety has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

g) Fc Region Variants

In some embodiments, one or more amino acid modifications may be introduced into the Fc region of the antibody moiety (e.g., scFv-Fc), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the Fc fragment possesses some but not all effector functions, which make it a desirable candidate for applications in which the half-life of the antibody moiety in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No.

6,737,056; WO 2004/056312, and Shields et al., *J. Biol. Chem.* 9(2): 6591-6604 (2001).)

In some embodiments, the antibody moiety comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, the antibody moiety (e.g., scFv-Fc) variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

h) Cysteine Engineered Antibody Variants

In some embodiments, it may be desirable to create cysteine engineered antibody moieties, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibody moieties may be generated as described, e.g., in U.S. Pat. No. 7,521,541.

i) Antibody Derivatives

In some embodiments, the antibody moiety described herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In some embodiments, the antibody moiety may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

VI. Methods of Preparation

In some embodiments, there is provided a method of preparing an imaging agent targeting an immune checkpoint ligand. The imaging agents described herein may be prepared by a number of processes as generally described below and more specifically in the Examples.

In some embodiments, there is provided a method of preparing an imaging agent targeting an immune checkpoint ligand, comprising: (a) conjugating a chelating compound to an antibody moiety (e.g., scFv) specifically binding the immune checkpoint ligand to provide an antibody moiety conjugate; and (b) contacting a radionuclide with the antibody moiety conjugate, thereby providing the imaging agent. In some embodiments, the immune checkpoint ligand is PD-L1. In some embodiments, the immune checkpoint ligand is a PD-L1 like ligand. In some embodiments, the chelating compound is NOTA, DOTA or derivatives thereof. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the antibody moiety. In some embodiments, the method further comprises isolating the imaging agent from the chelating compound and/or the radionuclide.

In some embodiments, there is provided a method of preparing an imaging agent targeting an immune checkpoint ligand, comprising: (a) conjugating a chelating compound to any one of the antibody moieties described herein to provide an antibody moiety conjugate, wherein the antibody moiety specifically binds the immune checkpoint ligand; and (b) contacting a radionuclide with the antibody moiety conjugate, thereby providing the imaging agent. In some embodiments, the immune checkpoint ligand is PD-L1. In some embodiments, the immune checkpoint ligand is a PD-L1 like ligand. In some embodiments, the chelating compound is NOTA, DOTA or derivatives thereof. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the antibody moiety. In some embodiments, the method further comprises isolating the imaging agent from the chelating compound and/or the radionuclide.

In some embodiments, there is provided a method of preparing an imaging agent targeting an immune checkpoint ligand, comprising: (a) contacting a chelating compound with a radionuclide; (b) conjugating the chelating compound that chelates the radionuclide to any one of the antibody moieties described herein, wherein the antibody moiety specifically binds the immune checkpoint ligand, thereby providing the imaging agent. In some embodiments, the immune checkpoint ligand is PD-L1. In some embodiments, the immune checkpoint ligand is a PD-L1 like ligand. In some embodiments, the chelating compound is NOTA, DOTA or derivatives thereof. In some embodiments, the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti. In some embodiments, the radionuclide is $^{68}$Ga. In some embodiments, the chelating compound is conjugated to a lysine of the antibody moiety. In some embodiments, the method further comprises isolating the imaging agent from the chelating compound and/or the radionuclide.

In some embodiments, there is provided a method of preparing an imaging agent targeting an immune checkpoint ligand, comprising: (a) conjugating an scFv specifically binding the immune checkpoint ligand (e.g., PD-L1 or a PD-L1 like ligand) to p-SCN-Bn-NOTA to provide an scFv conjugate; (b) contacting $^{68}$Ga with the scFv conjugate, thereby providing the imaging agent. In some embodiments, the scFv conjugate is isolated by passing the mixture of the scFv and p-SCN-Bn-NOTA through a column (e.g., NAP-5 column). In some embodiments, the imaging agent is isolated by passing the mixture of $^{68}$Ga with the scFv conjugate through a column (e.g., NAP-5 column).

Antibody Expression and Production

The antibody moieties described herein can be prepared using any known methods in the art, including those described below and in the Examples.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature*, 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986). Also see Example 1 for immunization in Camels.

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Also, see, Example 1 for monoclonal antibody production.
Nucleic Acid Molecules Encoding Antibody Moieties The present application further provides isolated nucleic acid molecules comprising polynucleotides that encode one or more chains of the antibody moieties (e.g., anti-PD-L1 antibody moieties) described herein. In some embodiments, a nucleic acid molecule comprises a polynucleotide that encodes a heavy chain or a light chain of an antibody moiety (e.g., anti-PD-L1 antibody moiety). In some embodiments, a nucleic acid molecule comprises both a polynucleotide that encodes a heavy chain and a polynucleotide that encodes a light chain, of an antibody moiety (e.g., anti-PD-L1 antibody moiety). In some embodiments, a first nucleic acid molecule comprises a first polynucleotide that encodes a heavy chain and a second nucleic acid molecule comprises a second polynucleotide that encodes a light chain. In some embodiments, a nucleic acid molecule encoding an scFv (e.g., anti-PD-L1 scFv) is provided.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody moiety (e.g., anti-PD-L1 antibody moiety) comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.
Vectors Vectors comprising polynucleotides that encode the heavy chains and/or light chains of any one of the antibody moieties described herein (e.g., anti-PD-L1 antibody moieties) are provided. Vectors comprising polynucleotides that encode any of the scFvs described herein (e.g., anti-PD-L1 scFv) are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

Host Cells

In some embodiments, the antibody moieties described herein (e.g., anti-PD-L1 antibody moieties) may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the antibody moieties described herein (e.g., anti-PD-L1 antibody moieties) may be expressed in yeast. See, e.g., U.S. Publication No. US 2006/0270045 A1. In some embodiments, a particular eukaryotic host cell is selected based on its ability to make desired post-translational modifications to the heavy chains and/or light chains of the antibody moiety. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The invention also provides host cells comprising any of the polynucleotides or vectors described herein. In some embodiments, the invention provides a host cell comprising an anti-PD-L1 antibody. Any host cells capable of overexpressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

In some embodiments, the antibody moiety is produced in a cell-free system. Non-limiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Purification of Antibody Moieties

The antibody moieties (e.g., anti-PD-L1 antibody moieties) may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an antibody moiety comprising an Fc fragment. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

VII. Compositions, Kits and Articles of Manufacture

Also provided herein are compositions (such as formulations) comprising any one of the imaging agents or the isolated anti-PD-L1 antibody agents described herein, nucleic acid encoding the antibody moieties (e.g., anti-PD-L1 antibody moieties), vector comprising the nucleic acid encoding the antibody moieties, or host cells comprising the nucleic acid or vector.

Suitable formulations of the imaging agents or the isolated anti-PD-L1 antibody agents described herein can be obtained by mixing the imaging agents or the isolated anti-PD-L1 antibody agents having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

The formulations to be used for in vivo administration must be sterile. This is readily accomplished by, e.g., filtration through sterile filtration membranes.

Also provided are kits comprising any one of the imaging agents, the isolated anti-PD-L1 antibody agents, and/or optionally the chelating compound and/or the radionuclide described herein. The kits may be useful for any of the methods of imaging, diagnosis and treatment described herein.

In some embodiments, there is provided a kit comprising an antibody moiety specifically binding an immune checkpoint ligand (e.g., PD-L1 or a PD-L1 like ligand), and a chelating compound (e.g., NOTA, DOTA or derivatives thereof). In some embodiments, the kit further comprises a radionuclide (e.g., $^{68}$Ga). In some embodiments, the chelating compound chelates the radionuclide.

In some embodiments, there is provided a kit comprising an imaging agent comprising an antibody moiety labeled with a radionuclide (e.g., $^{68}$Ga), wherein the antibody moiety specifically binds an immune checkpoint ligand (e.g., PD-L1 or a PD-L1 like ligand). In some embodiments, the antibody moiety is conjugated to a chelating moiety (e.g., NOTA, DOTA or derivatives thereof) that chelates the radionuclide. In some embodiments, the kit further comprises an antibody moiety not labeled with a radionuclide.

In some embodiments, the kit further comprises a device capable of delivering the imaging agent or the isolated anti-PD-L1 antibody agent. One type of device, for applications such as parenteral delivery, is a syringe that is used to inject the composition into the body of a subject. Inhalation devices may also be used for certain applications.

In some embodiments, the kit further comprises a therapeutic agent for treating a disease or condition, e.g., cancer, infectious disease, autoimmune disease, or metabolic disease. In some embodiments, the therapeutic agent is an inhibitor of the immune checkpoint ligand or receptor thereof. In some embodiments, the therapeutic agent is a radiolabeled molecule specifically binding the immune checkpoint ligand or receptor thereof.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information.

The present application thus also provides articles of manufacture. The article of manufacture can comprise a container and a label or package insert on or associated with the container. Suitable containers include vials (such as sealed vials), bottles, jars, flexible packaging, and the like. Generally, the container holds a composition, and may have a sterile access port (for example the container may be an intravenous solution bag or a vial having a stopper pierceable by a hypodermic injection needle). The label or package insert indicates that the composition is used for imaging, diagnosing, or treating a particular condition in an individual. The label or package insert will further comprise instructions for administering the composition to the individual and for imaging the individual. The label may indicate directions for reconstitution and/or use. The container holding the composition may be a multi-use vial, which allows for repeat administrations (e.g. from 2-6 administrations) of the reconstituted formulation. Package insert refers to instructions customarily included in commercial packages of diagnostic products that contain information about the indications, usage, dosage, administration, contraindications and/or warnings concerning the use of such diagnostic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the compositions and instructions for use, packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples.

The following examples further illustrate the invention but, of course, should not be construed as in any way limiting its scope.

EXEMPLARY EMBODIMENTS

Embodiment 1. A method of determining the distribution of an immune checkpoint ligand in an individual, comprising: (a) administering to the individual an imaging agent comprising an antibody moiety labeled with a radionuclide, wherein the antibody fragment specifically binds the immune checkpoint ligand; and (b) imaging the imaging agent in the individual with a non-invasive imaging technique.

Embodiment 2. The method of embodiment 1, further comprising determining the expression level of the immune checkpoint ligand in a tissue of interest in the individual based on signals emitted by the imaging agent from the tissue.

Embodiment 3. The method of embodiment 1 or 2, comprising determining the distribution of two or more immune checkpoint ligands in the individual.

Embodiment 4. The method of any one of embodiments 1-3, wherein the imaging agent is cleared from the individual within about 10 minutes to about 48 hours in serum.

Embodiment 5. The method of any one of embodiments 1-4, wherein the half-life of the antibody moiety is between about 10 minutes to about 24 hours.

Embodiment 6. The method of any one of embodiments 1-5, wherein the molecular weight of the antibody moiety is no more than about 120 kDa.

Embodiment 7. The method of any one of embodiments 1-6, wherein the antibody moiety has a $K_D$ between about $9 \times 10^{-10}$ M to about $1 \times 10^{-8}$ M with the immune checkpoint ligand.

Embodiment 8. The method of any one of embodiments 1-7, wherein the antibody moiety cross-reacts with the immune checkpoint ligand from a non-human mammal.

Embodiment 9. The method of embodiment 8, wherein the antibody moiety cross-reacts with the immune checkpoint ligand from a cynomolgus monkey.

Embodiment 10. The method of embodiment 8 or 9, wherein the antibody moiety cross-reacts with the immune checkpoint ligand from a mouse.

Embodiment 11. The method of any one of embodiments 1-10, wherein the antibody moiety is humanized.

Embodiment 12. The method of any one of embodiments 1-11, wherein the antibody moiety is stable at acidic or neutral pH.

Embodiment 13. The method of any one of embodiments 1-12, wherein the antibody moiety has a melting temperature (Tm) of about 55-70° C.

Embodiment 14. The method of any one of embodiments 1-13, wherein the antibody moiety is selected from the group consisting of a single-chain Fv (scFv), a diabody, a Fab, a Fab', a F(ab')$_2$, an Fv fragment, a disulfide stabilized Fv fragment (dsFv), a (dsFv)$_2$, and a $V_H$H.

Embodiment 15. The method of any one of embodiments 1-14, wherein the antibody moiety is an scFv.

Embodiment 16. The method of embodiment 15, wherein the scFv comprises one or more engineered disulfide bonds.

Embodiment 17. The method of embodiment 16, wherein the scFv comprises a first engineered cysteine residue at position 44 of $V_H$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

Embodiment 18. The method of any one of embodiments 1-13, wherein the antibody moiety is an scFv fused to an Fc fragment.

Embodiment 19. The method of embodiment 18, wherein the Fc fragment is a human IgG1 Fc fragment.

Embodiment 20. The method of embodiment 18 or 19, wherein the Fc fragment has H310A and H435Q mutations, wherein the amino acid positions are based on the Kabat numbering system.

Embodiment 21. The method of any one of embodiments 15-20, wherein the scFv comprises from the N-terminus to the C-terminus: a heavy chain variable region ($V_H$), an optional peptide linker, and a light chain variable region ($V_L$).

Embodiment 22. The method of any one of embodiments 15-20, wherein the scFv comprises from the N-terminus to the C-terminus: a $V_L$, an optional peptide linker, and a $V_H$.

Embodiment 23. The method of embodiment 21 or 22, wherein the scFv comprises a peptide linker comprising the amino acid sequence of SEQ ID NO: 47 or 48.

Embodiment 24. The method of any one of embodiments 1-23, wherein the immune checkpoint ligand is PD-L1 or a PD-L1 like ligand.

Embodiment 25. The method of embodiment 24, wherein the immune checkpoint ligand is PD-L1.

Embodiment 26. The method of embodiment 25, wherein the antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46; or the antibody moiety specifically binds PD-L1 competitively with an anti-PD-L1 antibody comprising: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46.

Embodiment 27. The method of any one of embodiments 2-26, wherein the tissue of interest is negative for the immune checkpoint ligand based on an immunohistochemistry (IHC) assay or another assay.

Embodiment 28. The method of any one of embodiments 2-27, wherein the tissue of interest has a low expression level of the immune checkpoint ligand.

Embodiment 29. The method of any one of embodiments 2-28, wherein the tissue of interest only expresses the immune checkpoint ligand upon infiltration of immune cells.

Embodiment 30. The method of any one of embodiments 1-29, wherein the method comprises imaging the individual over a period of time.

Embodiment 31. The method of any one of embodiments 1-30, wherein the radionuclide is selected from the group consisting of $^{64}Cu$, $^{18}F$, $^{67}Ga$, $^{68}Ga$, $^{111}In$, $^{177}Lu$, $^{90}Y$, $^{89}Zr$, $^{61}Cu$, $^{62}Cu$, $^{67}Cu$, $^{19}F$, $^{66}Ga$, $^{72}Ga$, $^{44}Sc$, $^{47}Sc$, $^{86}Y$, $^{88}Y$ and $^{45}Ti$.

Embodiment 32. The method of embodiment 31, wherein the radionuclide is $^{68}Ga$.

Embodiment 33. The method of embodiment 31 or 32, wherein the antibody moiety is conjugated to a chelating compound that chelates the radionuclide.

Embodiment 34. The method of embodiment 33, wherein the chelating compound is 1,4,7-triazacyclononane-1,4,7-trisacetic acid (NOTA), 1,4,7,10-tetraazacyclododecane-1,4,7,10-tetraacetic acid (DOTA) or derivatives thereof.

Embodiment 35. The method of embodiment 34, wherein the chelating compound is NOTA.

Embodiment 36. The method of any one of embodiments 1-35, further comprising preparing the imaging agent by labeling the antibody moiety with the radionuclide.

Embodiment 37. The method of any one of embodiments 1-36, wherein the non-invasive imaging technique comprises single photon emission computed tomography (SPECT) imaging or positron emission tomography (PET) imaging.

Embodiment 38. The method of embodiment 37, wherein the non-invasive imaging technique comprises computed tomography imaging, magnetic resonance imaging, chemical luminescence imaging, or electrochemical luminescence imaging.

Embodiment 39. The method of any one of embodiments 1-38, wherein the imaging agent is administered intravenously, intraperitoneally, intramuscularly, subcutaneously, or orally.

Embodiment 40. The method of any one of embodiments 1-39, wherein the imaging is carried out between about 10 minutes to about 24 hours after the administration of the imaging agent.

Embodiment 41. The method of any one of embodiments 1-40, further comprising administering to the individual an antibody moiety not labeled with a radionuclide prior to the administration of the imaging agent.

Embodiment 42. The method of any one of embodiments 1-41, wherein the individual has a solid tumor.

Embodiment 43. The method of embodiment 42, wherein the solid tumor is selected from the group consisting of colon tumor, melanoma, kidney tumor, ovarian tumor, lung tumor, breast tumor, and pancreatic tumor.

Embodiment 44. The method of any one of embodiments 1-43, wherein the individual has a hematological malignancy.

Embodiment 45. The method of embodiment 44, wherein the hematological malignancy is selected from the group consisting of leukemia, lymphoma, acute lymphoblastic leukemia (ALL), acute non-lymphoblastic leukemia (ANLL), chronic lymphocytic leukemia (CLL), chronic myeloid leukemia (CML), non-Hodgkin lymphoma, and Hodgkin lymphoma.

Embodiment 46. The method of any one of embodiments 1-41, wherein the individual has an infectious disease, autoimmune disease, or metabolic disease.

Embodiment 47. A method of diagnosing an individual having a disease or condition, comprising: (a) determining the distribution of an immune checkpoint ligand in the individual using the method of any one of embodiments 1-46; and (b) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest.

Embodiment 48. A method of treating an individual having a disease or condition, comprising: (a) diagnosing the individual using the method of embodiment 47; and (b)

administering to the individual an effective amount of a therapeutic agent targeting the immune checkpoint ligand or receptor thereof, if the individual is diagnosed as positive for the immune checkpoint ligand.

Embodiment 49. The method of embodiment 48, wherein the therapeutic agent is an inhibitor of the immune checkpoint ligand or receptor thereof.

Embodiment 50. The method of embodiment 48, wherein the therapeutic agent is a radiolabeled molecule specifically binding the immune checkpoint ligand or receptor thereof.

Embodiment 51. The method of any one of embodiments 48-50, wherein the immune checkpoint ligand is PD-L1, and wherein the individual is administered with an antibody specifically binding PD-1 or PD-L1.

Embodiment 52. The method of any one of embodiments 48-50, wherein the immune checkpoint ligand is a PD-L1 like ligand.

Embodiment 53. An isolated anti-PD-L1 antibody agent comprising an antibody moiety comprising a heavy chain variable region ($V_H$) comprising a heavy chain complementarity determining region (HC-CDR)1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43, or a variant thereof comprising up to about 5 amino acid substitutions; and a light chain variable region ($V_L$) comprising a light chain complementarity determining region (LC-CDR)1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46, or a variant thereof comprising up to about 5 amino acid substitutions.

Embodiment 54. The isolated anti-PD-L1 antibody agent of embodiment 53, wherein the antibody moiety comprises: a $V_H$ comprising a HC-CDR1 comprising the amino acid sequence of SEQ ID NO: 41, a HC-CDR2 comprising the amino acid sequence of SEQ ID NO: 42, and a HC-CDR3 comprising the amino acid sequence of SEQ ID NO: 43; and a $V_L$ comprising a LC-CDR1 comprising the amino acid sequence of SEQ ID NO: 44, a LC-CDR2 comprising the amino acid sequence of SEQ ID NO: 45, and a LC-CDR3 comprising the amino acid sequence of SEQ ID NO: 46.

Embodiment 55. An isolated anti-PD-L1 antibody agent comprising an antibody moiety comprising a $V_H$ comprising a HC-CDR1, a HC-CDR2, and a HC-CDR3 of SEQ ID NO: 1; and a $V_L$ comprising a LC-CDR1, a LC-CDR2, and a LC-CDR3 of SEQ ID NO: 3.

Embodiment 56. The isolated anti-PD-L1 antibody agent of any one of embodiment 53-55, wherein the antibody moiety comprises: a $V_H$ comprising an amino acid sequence having at least about 80% sequence identity to the amino acid sequence of any one of SEQ ID NOs: 1, 5, 9, 11, and 13; and a $V_L$ comprising an amino acid sequence having at least about 80% sequence identity to the amino acid sequence of any one of SEQ ID NOs: 3, 7, 15, 17 and 19.

Embodiment 57. The isolated anti-PD-L1 antibody agent of embodiment 56, wherein the antibody moiety comprises: (a) a $V_H$ comprising the amino acid sequence of SEQ ID NO: 9, and a $V_L$ comprising the amino acid sequence of SEQ ID NO: 15; (b) a $V_H$ comprising the amino acid sequence of SEQ ID NO: 9, and a $V_L$ comprising the amino acid sequence of SEQ ID NO: 17; (c) a $V_H$ comprising the amino acid sequence of SEQ ID NO: 9, and a $V_L$ comprising the amino acid sequence of SEQ ID NO: 19; (d) a $V_H$ comprising the amino acid sequence of SEQ ID NO: 11, and a $V_L$ comprising the amino acid sequence of SEQ ID NO: 15; (e) a $V_H$ comprising the amino acid sequence of SEQ ID NO: 11, and a $V_L$ comprising the amino acid sequence of SEQ ID NO: 17; (f) a $V_H$ comprising the amino acid sequence of SEQ ID NO: 11, and a $V_L$ comprising the amino acid sequence of SEQ ID NO: 19; (g) a $V_H$ comprising the amino acid sequence of SEQ ID NO: 13, and a $V_L$ comprising the amino acid sequence of SEQ ID NO: 15; (h) a $V_H$ comprising the amino acid sequence of SEQ ID NO: 13, and a $V_L$ comprising the amino acid sequence of SEQ ID NO: 17; or (i) a $V_H$ comprising the amino acid sequence of SEQ ID NO: 13, and a $V_L$ comprising the amino acid sequence of SEQ ID NO: 19.

Embodiment 58. The isolated anti-PD-L1 antibody agent of any one of embodiments 53-57, wherein the antibody moiety is humanized.

Embodiment 59. The isolated anti-PD-L1 antibody agent of any one of embodiments 53-58, wherein the antibody moiety comprises an scFv.

Embodiment 60. The isolated anti-PD-L1 antibody agent of embodiment 59, wherein the scFv comprises a first engineered cysteine residue at position 44 of $V_1$ and a second engineered cysteine residue at position 100 of $V_L$, or a first engineered cysteine residue at position 105 of $V_H$ and a second engineered cysteine residue at position 43 of $V_L$, wherein the first engineered cysteine residue and the second engineered cysteine residue form a disulfide bond, and wherein the amino acid positions are based on the Kabat numbering system.

Embodiment 61. The isolated anti-PD-L1 antibody agent of embodiment 59 or 60, wherein the scFv comprises an amino acid sequence having at least about 80% sequence identity to the amino acid sequence of any one of SEQ ID NOs: 25, 27, 29, 31, 33, 35, 37 and 39.

Embodiment 62. The isolated anti-PD-L1 antibody agent of embodiment 61, wherein the scFv comprises the amino acid sequence of any one of SEQ ID NOs: 25, 27, 29, 31, 33, 35, 37 and 39.

Embodiment 63. The isolated anti-PD-L1 antibody agent of any one of embodiments 59-62, wherein the antibody moiety is an scFv.

Embodiment 64. The isolated anti-PD-L1 antibody agent of any one of embodiments 59-62, wherein the antibody moiety is an scFv fused to an Fc fragment.

Embodiment 65. The isolated anti-PD-L1 antibody agent of embodiment 64, wherein the Fc fragment is a human IgG1 Fc fragment.

Embodiment 66. The isolated anti-PD-L1 antibody agent of embodiment 64 or 65, wherein the Fc fragment has H310A and H435Q mutations, wherein the amino acid positions are based on the Kabat numbering system.

Embodiment 67. An anti-PD-L1 antibody agent comprising an antibody moiety that specifically binds PD-L1 competitively with the antibody moiety in the anti-PD-L1 antibody agent of any one of embodiments 53-66.

Embodiment 68. An imaging agent comprising an antibody moiety labeled with a radionuclide, wherein the antibody moiety specifically binds an immune checkpoint ligand.

Embodiment 69. The imaging agent of embodiment 68, wherein the immune checkpoint ligand is PD-L1 or a PD-L1 like ligand.

Embodiment 70. An imaging agent comprising the isolated anti-PD-L1 antibody agent of any one of embodiments 53-67, wherein the antibody moiety is labeled with a radionuclide.

Embodiment 71. The imaging agent of any one of embodiments 68-70, wherein the radionuclide is selected from the group consisting of $^{64}$Cu, $^{18}$F, $^{67}$Ga, $^{68}$Ga, $^{111}$In, $^{177}$Lu, $^{90}$Y, $^{89}$Zr, $^{61}$Cu, $^{62}$Cu, $^{67}$Cu, $^{19}$F, $^{66}$Ga, $^{72}$Ga, $^{44}$Sc, $^{47}$Sc, $^{86}$Y, $^{88}$Y and $^{45}$Ti.

Embodiment 72. The imaging agent of embodiment 71, wherein the radionuclide is $^{68}$Ga.

Embodiment 73. The imaging agent of embodiment 71 or 72, wherein the antibody moiety is conjugated to a chelating compound that chelates the radionuclide.

Embodiment 74. The imaging agent of embodiment 73, wherein the chelating compound is NOTA, DOTA, or derivatives thereof.

Embodiment 75. The imaging agent of embodiment 74, wherein the chelating compound is NOTA.

Embodiment 76. A method of preparing an imaging agent targeting an immune checkpoint ligand, comprising: (a) conjugating a chelating compound to an antibody moiety specifically binding the immune checkpoint ligand to provide an antibody moiety conjugate; (b) contacting a radionuclide with the antibody moiety conjugate, thereby providing the imaging agent.

Embodiment 77. The method of embodiment 76, wherein the immune checkpoint ligand is PD-L1 or a PD-L1 like ligand.

Embodiment 78. A method of preparing an imaging agent targeting PD-L1, comprising: (a) conjugating a chelating compound to the antibody moiety in the isolated anti-PD-L1 antibody agent of any one of embodiments 53-67 to provide an anti-PD-L1 conjugate; and (b) contacting a radionuclide with the anti-PD-L1 antibody conjugate, thereby providing the imaging agent.

Embodiment 79. The method of any one of embodiments 76-78, wherein the chelating compound is conjugated to a lysine of the antibody moiety.

Embodiment 80. An isolated nucleic acid encoding the isolated anti-PD-L1 antibody agent of any one of embodiments 53-67.

Embodiment 81. A vector comprising the isolated nucleic acid of embodiment 80.

Embodiment 82. An isolated host cell comprising the isolated anti-PD-L1 antibody agent of any one of embodiments 53-67, the isolated nucleic acid of embodiment 80, or the vector of embodiment 81.

Embodiment 83. A pharmaceutical composition comprising the isolated anti-PD-L1 antibody agent of any one of embodiments 53-67.

Embodiment 84. A kit comprising the isolated anti-PD-L1 antibody agent of any one of embodiments 53-67 or the imaging agent of any one of embodiments 68-75.

Embodiment 85. A kit comprising: (a) an antibody moiety specifically binding an immune checkpoint ligand; and (b) a chelating compound.

Embodiment 86. The kit of embodiment 85, further comprising a radionuclide.

Embodiment 87. A kit comprising: (a) an imaging agent comprising an antibody moiety labeled with a radionuclide, wherein the antibody moiety specifically binds an immune checkpoint ligand; and (b) an antibody moiety not labeled with a radionuclide.

EXAMPLES

The examples below are intended to be purely exemplary of the invention and should therefore not be considered to limit the invention in any way. The following examples and detailed description are offered by way of illustration and not by way of limitation.

Example 1: Preparation and Characterization of Monoclonal Antibodies Against Human PD-L1

Immunization 8-10 weeks old female PD-L1 deficient mice (H Dong et al. Immunity. 2004 March; 20(3):327-36) were immunized subcutaneously (s.c.) at multiple sites with 200 µl of emulsion comprising 100 µg of hPD-L1mIg fusion protein and complete Freund's adjuvant (CFA) (Sigma-Aldrich). Each animal received two or three boosts with emulsion comprising the same concentration of hPD-L1mIg fusion protein formulated in incomplete Freund's adjuvant (IFA) (Sigma-Aldrich). Blood samples were collected from the animals two weeks after each immunization for serum titer testing. Upon achieving a sufficient titer, the animals received a booster injection with 60 µg of the PD-L1mIg fusion protein in PBS through intraperitoneal injection (i.p.). The animals were sacrificed and their spleens were harvested aseptically 5 days after the booster injection.

Whole spleen was dissociated into single-cell suspensions. Red blood cells were lysed using the ACK buffer. The spleen cells were then mixed with SP2/0-Ag14 myeloma cells (from ATCC) at a 1:1 ratio in 50 ml conical centrifuge tubes. After centrifugation, the supernatant was discarded and cell fusion was induced with 50% polyethylene glycol (Roche). The fused cells were cultured for 8-10 days in the HAT selection medium. The contents in the supernatant were analyzed for their ability to bind to hPD-1-expressing cells using ELISA, and the positive clones were further confirmed using flow cytometry analysis. Subcloning of the positive hybridoma was performed using the limiting dilution technique for 5 times to achieve a pure monoclonal culture.

Characterization of the Anti-hPD-L1 Monoclonal Antibody

Binding Specificity of the Anti-hPD-L1 Monoclonal Antibody

Figure 1B:
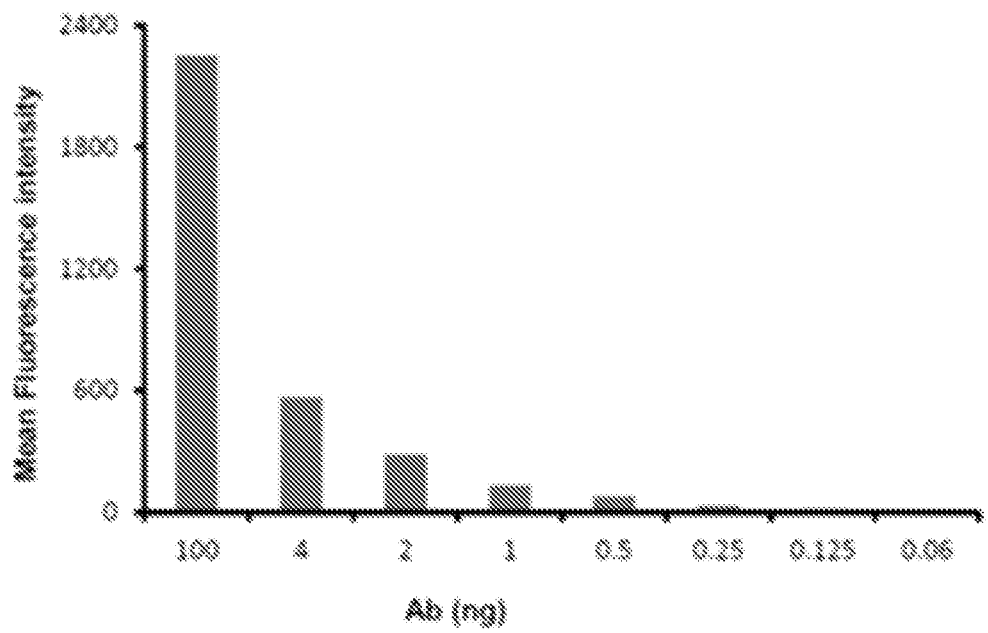

The binding specificity of the anti-hPD-L1 mAb was determined using hPD-L1 transfected CHO cells (CHO/hPD-L1 cells) by flow cytometry (FACSVerse, BD Biosciences). Specifically, CHO/hPD-L1 cells were incubated with increasing amounts of the anti-hPD-L1 mAb 5B7 (0.06 ng, 0.125 ng, 0.25 ng, 0.5 ng, 1 ng, 2 ng, 4 ng, and 100 ng) on ice for 30 minutes. The cells were then washed and further incubated with anti-mIgG-APC (eBioscience) prior to flow cytometry analysis. As shown in FIGS. 1A and 1B, the anti-hPD-L1 mAb 5B7 bound to hPD-L1 with high specificity in a dose-dependent manner.

The isotype of the monoclonal antibody was determined to be IgG1κ using the Mouse Immunoglobulin Isotyping Kit (BD Biosciences).

Species Cross-Reactivity

Figure 2A:
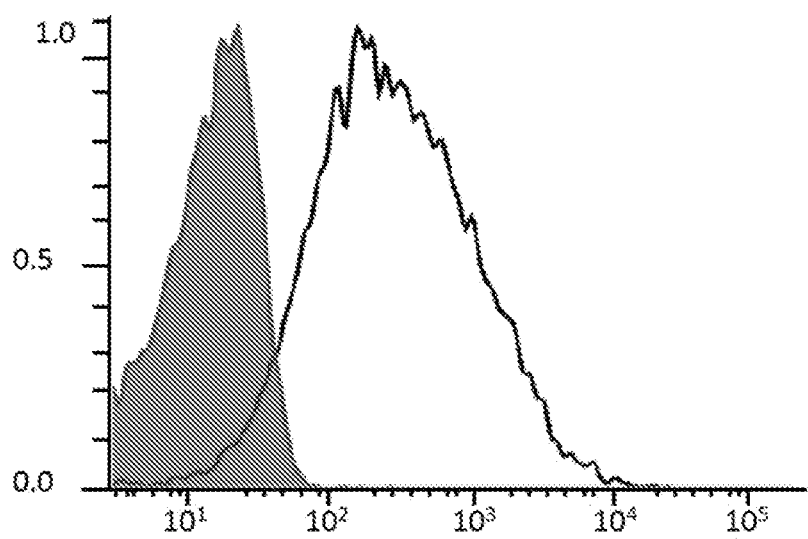
FIGS. 2A and 2B show the binding affinity of the anti-hPD-L1 monoclonal antibody to CHO cells expressing hPD-L1 protein or mPD-L1 protein.
Figure 2B:
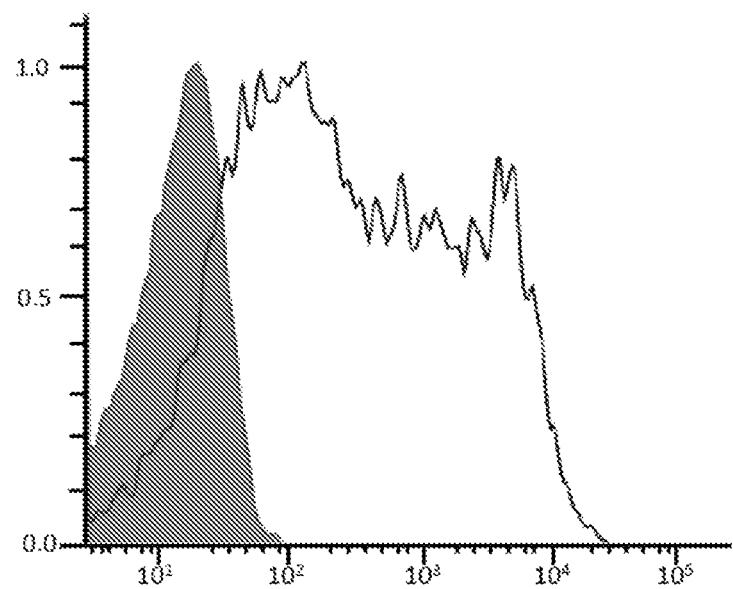

CHO cells transfected with mouse PD-L1 (CHO/mPD-L1) were used to assess the species cross-reactivity of the anti-hPD-L1 mAb with mouse PD-L1. The cells were incubated with the anti-hPD-L1 mAb prior to flow cytometry analysis. FIG. 2A shows the binding specificity of the anti-hPD-L1 mAb to human PD-L1. As shown in FIG. 2B, the anti-hPD-L1 mAb also binds to mouse PD-L1.

Sequencing of Anti-hPD-L1 Antibody-Producing Hybridoma Cells

To sequence antibody-producing hybridoma cells, 1×10$^7$ hybridoma cells were harvested and washed with PBS. Messenger RNAs were extracted from hybridomas using RNeasy Mini Kit (Qiagen). RACE-Ready first-Strand cDNAs were synthesized using SMARTer RACE cDNA Amplification Kit (Clontech). Following reverse transcription, 5' RACE PCR reactions were performed with ready cDNA as template and with 5' universal primer (UPM) provided by the kit and 3'gene specific primers (GSP1) designed using the mouse IgG1 heavy chain variable region and light chain variable region sequences. RACE products were determined by gel electrophoresis analysis. PCR products were then cloned into a T vector using Zero Blunt TOPO PCR Cloning Kit (Invitrogen). After transformation, the plasmids were verified by sequencing analysis. Sequences of the heavy chain variable region and light chain variable region were analyzed using VBASE2 (worldwide wweb.vbase2.org), and listed in Table 3.

Example 2: Humanization and Characterization of Anti-hPD-L1 Antibodies

Humanization of Anti-hPD-L1 Antibodies

Humanization was performed based on the heavy chain variable region (VH) and light chain variable region (VL) sequences from anti-hPD-L1 hybridoma cells. As an initial step, a mouse-human chimeric mAb comprising the parental mouse VH and VL sequences, the human IgG constant region and the human κchain was generated. Upon characterization of the chimeric antibody, three VH and three VL humanized sequences were designed and used to generate nine humanized antibodies. The VH and VL sequences of the chimeric and humanized anti-hPD-L1 antibodies are listed in Table 2.

Characterization of Humanized Anti-hPD-L1 Antibodies

Binding Activities of Humanized Anti-hPD-L1 Antibodies

Figure 3:
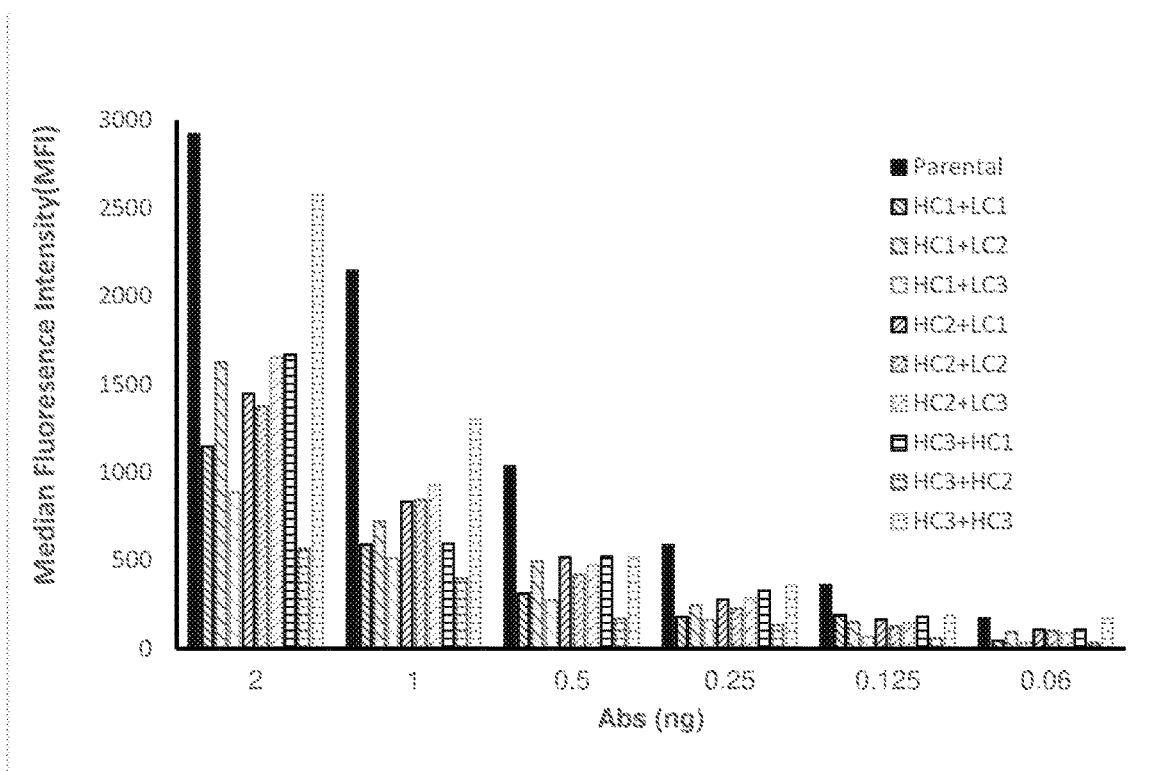
FIG. 3 shows the binding affinities of humanized anti-hPD-L1 antibodies to PD-L1 as compared to the parental mouse antibody.

To examine the binding activities of the humanized antibodies as compared to the parental chimeric antibody, CHO/hPD-L1 cells were incubated with the serially diluted parental chimeric antibody or humanized antibodies. The binding affinities were analyzed using flow cytometry, and the results showed that some humanized antibodies demonstrated higher binding affinities to hPD-L1 as compared to the parental chimeric antibody, while other humanized antibodies demonstrated similar or slightly lower binding affinities as compared to the parental chimeric antibody (FIG. 3).

Binding Affinities and Kinetics of the Humanized Anti-hPD-L1 Antibodies

Figure 4:
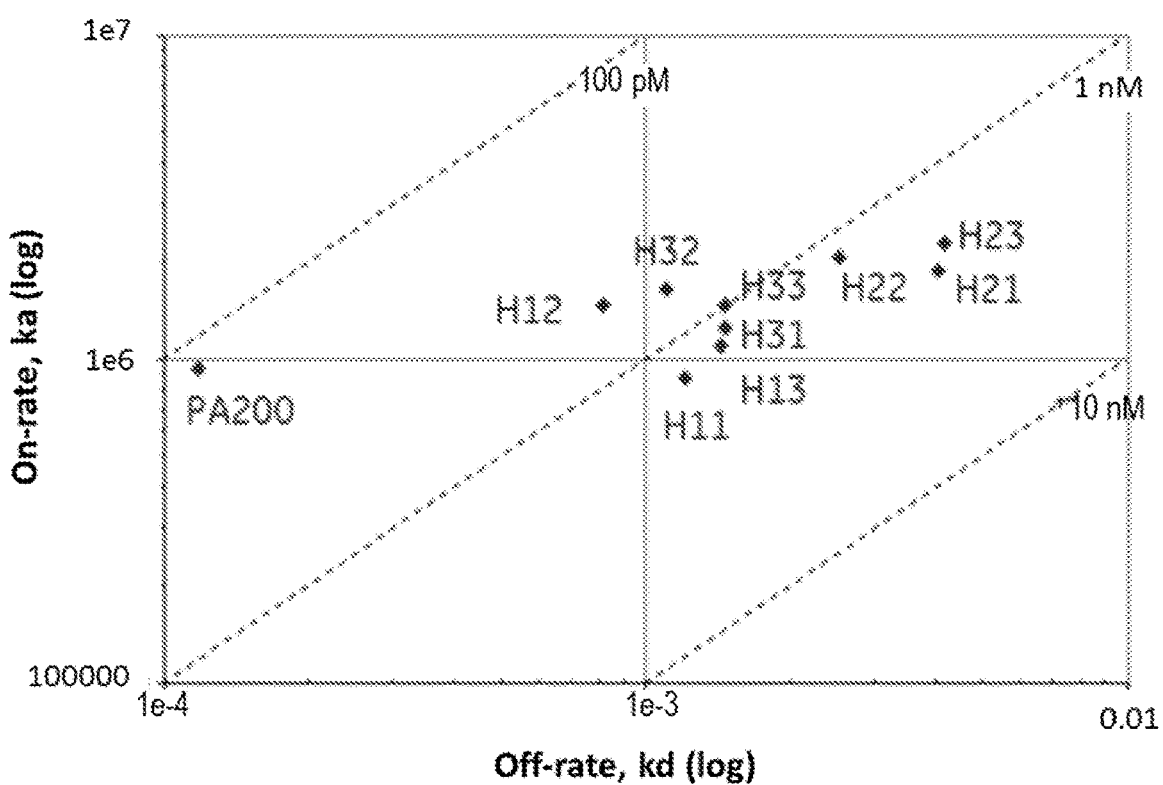
FIG. 4 shows binding affinity and kinetics profiles of humanized antibodies as compared to the parental mouse antibody.

The binding affinities and kinetics between the humanized anti-hPD-L1 mAbs and the hPD-L1 protein were assessed with Biacore T200 (GE Healthcare Life Sciences). The hPD-L1mIg protein was immobilized on the sensor chip CM5 by amine coupling. The parental and humanized antibodies were injected at a concentration gradient of 1, 2, 4, 8, 16, and 32 nM. Binding kinetic parameters, including association rate ($K_{on}$), dissociation rate ($K_{off}$), and affinity constant ($K_D$) were determined by full kinetic analysis. As shown in Table 7, there were no significant differences in the association rate ($K_{on}$) among the parental antibody and the humanized antibodies. As shown in Table 7 and FIG. 4, the antibodies with dissociation rates ($K_{off}$) from the lowest to the highest were: parental (PA200), H1+L2 (H12), H3+L2 (H32), H1+L1 (H11), H1+L3 (H13), H3+L1 (H31), H3+L3 (H33), H2+L2 (H22), H2+L1 (H21), and H2+L3 (H23). As shown in Table 7, the antibodies with affinity constant (KD) from the highest to the lowest were: parental, H1+L2, H3+L2, H3+L3, H3+L1, H2+L2, H1+L3, H1+L1, H2+L3, and H2+L1.

TABLE 7

$K_{on}$, $K_{off}$ and $K_D$ values of the parental and humanized antibodies

| Antibody | $K_{on}$ (1/Ms) | $K_{off}$ (1/s) | $K_D$ (M) |
| --- | --- | --- | --- |
| anti-PD-L1 parental | 9.243E+5 | 1.180E−4 | 1.276E−10 |
| anti-PD-L1 HC1 + LC1 | 8.686E+5 | 0.001200 | 1.381E−9 |
| anti-PD-L1 HC1 + LC2 | 1.456E+6 | 8.114E−4 | 5.572E−10 |
| anti-PD-L1 HC1 + LC3 | 1.100E+6 | 0.001430 | 1.301E−9 |
| anti-PD-L1 HC2 + LC1 | 1.863E+6 | 0.004058 | 2.178E−9 |
| anti-PD-L1 HC2 + LC2 | 2.049E+6 | 0.002515 | 1.227E−9 |
| anti-PD-L1 HC2 + LC3 | 2.265E+6 | 0.004171 | 1.841E−9 |
| anti-PD-L1 HC3 + LC1 | 1.250E+6 | 0.001464 | 1.171E−9 |
| anti-PD-L1 HC3 + LC2 | 1.646E+6 | 0.001096 | 6.659E−10 |
| anti-PD-L1 HC3 + LC3 | 1.461E+6 | 0.001465 | 1.003E−9 |

Figure 5:
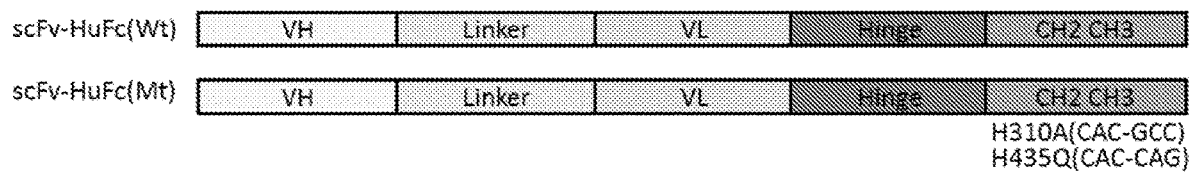
FIG. 5 shows a schematic diagram of the construct design for scFv-HuFc(Wt) and scFv-HuFc(Mt).

Example 3: Preparation and Characterization of Anti-hPD-L1 scFv-hFc Antibodies Sequence Design and Synthesis of scFv-hFc Antibodies The heavy chain variable region (VH) and light chain variable region (VL) of the humanized anti-hPD-L1 antibody variant 2 was used to generate the scFv-hFc antibody. Specifically, the heavy chain and light chain were connected by a linker, which was followed by a hinge sequence (GACAAGACCCACACCTGCCCTCCCTGCCCC, SEQ ID NO: 50) and a human immunoglobulin IgG1 Fc portion (CH2-CH3 region). Additionally, H310A (i.e., CAC to GCC) and H435Q (i.e., CAC to CAG) mutations were introduced into the CH2 and CH3 regions for rapid clearance of the antibody in vivo (FIG. 5). The sequences of the scFv-hFc antibodies with the wild type CH2-CH3 regions (scFv-hFc Wt) and with the mutant CH2-CH3 regions (scFv-hFc Mt) are shown in Table 6.

The DNA sequences of scFv-hFc Wt and scFv-hFc Mt were cloned into pcDNA3.3 vectors respectively and used to transiently transfected ExPi 293 cells. The proteins from the cell culture supernatant were purified with protein G sepharose column (GE healthcare) for functional analysis.

Characterization of scFv-hFc Antibodies

Figure 6:
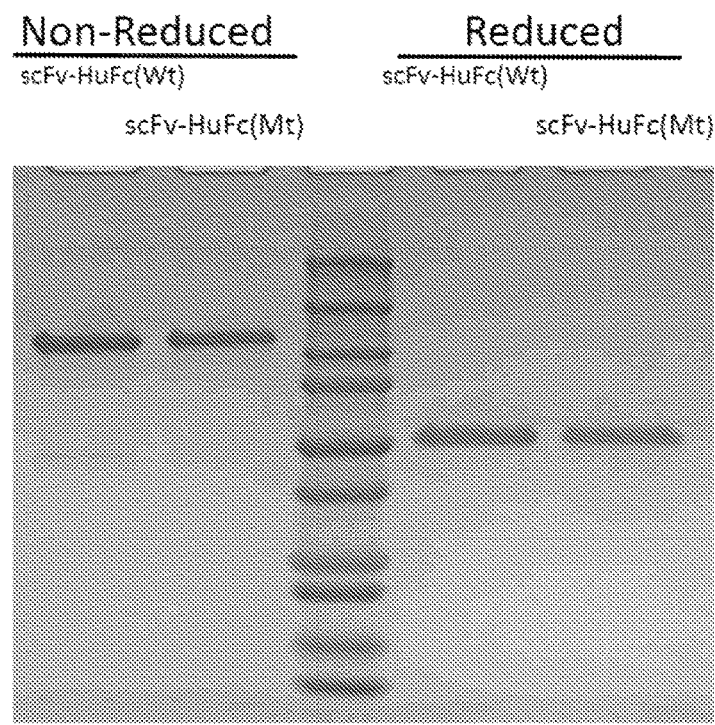
FIG. 6 shows the SDS-PAGE results for scFv-HuFc(Wt) and scFv-HuFc(Mt) in both the reduced and non-reduced conditions.
Figure 7:
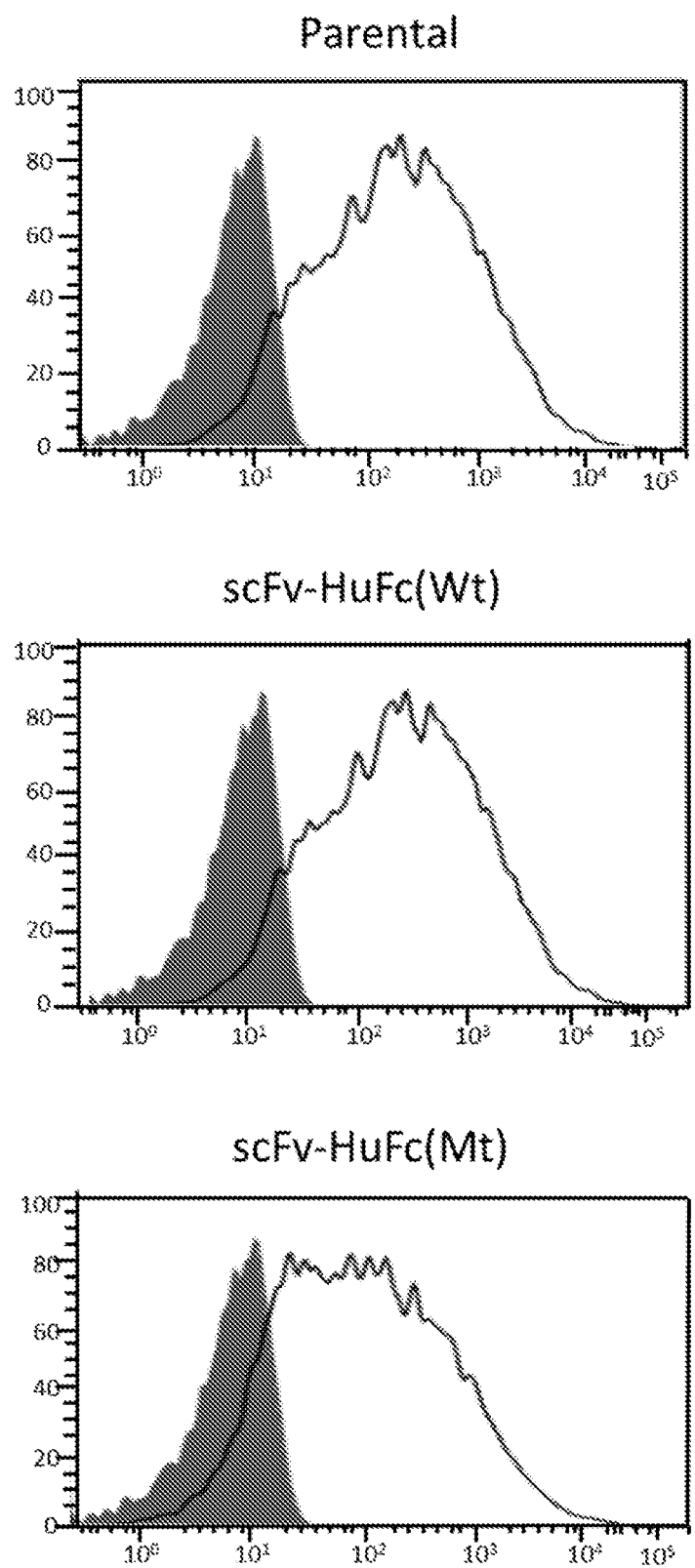
FIG. 7 shows histograms demonstrating the binding affinities of scFv-HuFc(Wt) and scFv-HuFc(Mt) to PD-L1 as compared to that of the parental antibody.

The anti-hPD-L1 scFv-hFc Wt and scFv-hFc Mt antibodies were identified by SDS Page Gel Electroporation. As shown in FIG. 6, the scFv-hFc antibodies were identified in both the reduced and non-reduced conditions on the SDS-PAGE gel. The binding affinities of the scFv-hFc antibodies to hPD-L1, as compared to that of the parental antibody were examined by FACS and the results are shown in FIG. 7. As shown in the histograms, both scFv-hFc Wt and scFv-hFc Mt demonstrated similar binding affinities as the parental antibody. The binding affinities and kinetics of the scFv-hFc antibodies (scFv-hFc Wt and scFv-hFc Mt) to hPD-L1, as compared to that of the parental antibody (anti-PD-L1 IgG1), were further analyzed using the Fortebio Octet system. Table 8 shows the binding affinities and kinetics parameters of anti-PD-L1 IgG1, anti-PD-L1 IgG1-C52W (i.e., an anti-PD-L1 antibody having an IgG1 Fc region with a C52W mutation), scFv-hFc Mt and scFv-hFc Wt.

TABLE 8

Binding kinetics parameters of anti-hPD-L1 scFv-hFc
and parental control antibodies

| Sample | $K_D$ (M) | $K_{on}$ (1/Ms) | $K_{off}$ (1/s) | $R^2$ |
|---|---|---|---|---|
| anti-PD-L1 IgG1 | 1.54E−11 | 1.77E+5 | 2.72E−5 | 0.9834 |
| anti-PD-L1 IgG1 C52W | 3.40E−10 | 1.33E+5 | 4.53E−4 | 0.9732 |
| anti-PD-L1 scFv-hFc Wt | 3.48E−10 | 6.98E+6 | 2.43E−4 | 0.97 |
| anti-PD-L1 scFv-hFc Mt | 2.32E−10 | 1.66E+6 | 3.85E−4 | 0.9812 |

Figure 8A:
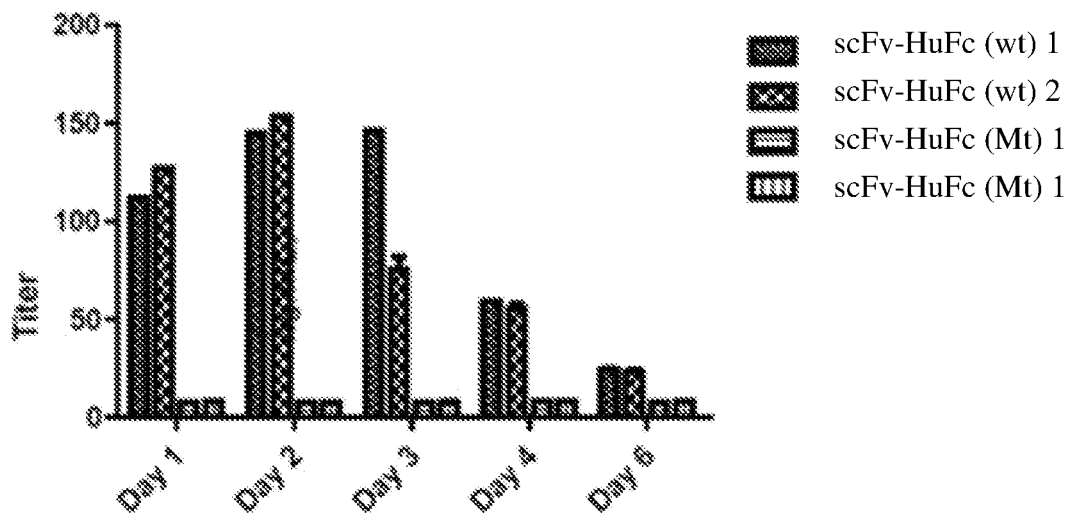
FIGS. 8A and 8B show serum titers of anti-hPD-L1 antibodies and hIgG following intravenous injections of anti-hPD-L1 scFv-HuFc fusion proteins scFv-hFc Wt and scFv-hFc Mt.
Figure 8B:
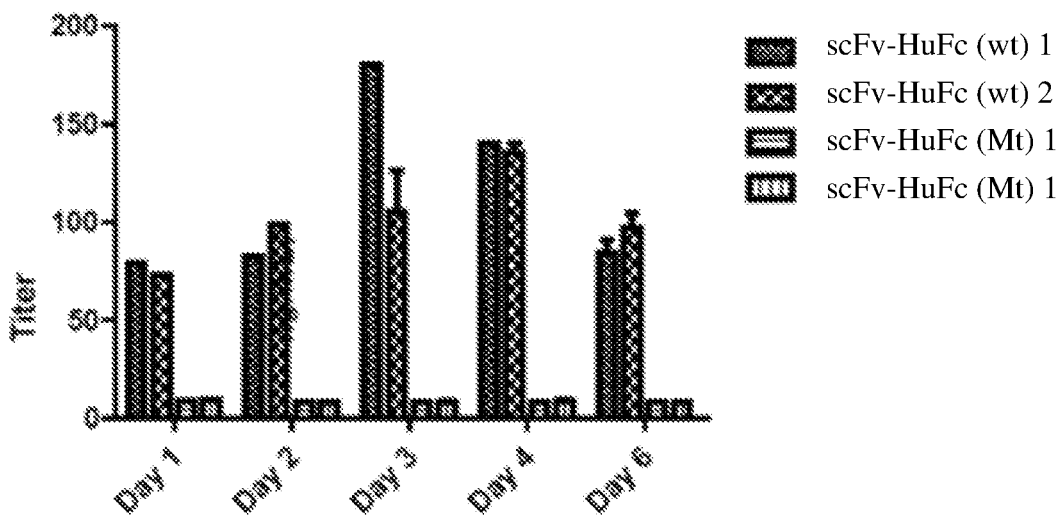

Pharmacokinetics studies were performed by injection of scFv-hFc Wt and scFv-hFc Mt antibodies in vivo, followed by measuring of the serum titers of the scFv-hFc antibodies and hIgG on Day 1, 2, 3, 4 and 6 after injection. As shown in FIGS. 8A and 8B, scFv-hFc Wt showed higher serum titer of the antibody and of hIgG as compared to scFv-hFc Mt.

Example 4: Generation and Characterization of Anti-PD-L1 scFv

Generation and Small-Scale Expression of Humanized Anti-PD-L1 scFv

Schematic diagrams of the construct designs for anti-hPD-L1 scFvs, the parental humanized IgG1 positive control antibody and a negative control scFv are shown in FIG. 9. Specifically, fragments containing VH and VL antigen binding domains from the humanized anti-hPD-L1 antibody and a peptide linker in between were artificially synthesized, which included both orientations (i.e., VH-linker-VL and VL-linker-VH). The (Gly4-Ser)4 (SEQ ID NO: 47) peptide and GSTSGSGKPGSGEGSTKG (SEQ ID NO: 48) peptide linker were used in the construction of all scFvs. In addition, sc-dsFvs were also constructed by introducing single mutations at VH44/VL100 or VH105/VL43 (according to the Kabat numbering system). The fragments containing VH and VL also included restriction endonuclease HindIII and EcoRI recognition sites at the 5' and 3' ends, respectively, as well as a His tag sequence at the C-terminal. The fragments containing VH and VL were fused with either human IgG1 heavy chain CH1-CH2-CH3 or IgG1 light chain CL, at the 5' end by overlapping PCR. The fused heavy chain and light chain were then cloned into the corresponding HindIII and EcoRI recognition sites of the pCDNA3.1(+) expression vector. A total of eight scFvs were designed and synthesized. The scFvs comprise the sequences shown in Table 5. In addition, each scFv comprises a His tag fused to the C-terminus via a short peptide linker (i.e., SEQ ID NO: 51). Constructs for the parental humanized IgG1 positive control antibody and a negative control scFv (irr-control scFv) were also synthesized.

Figure 10:
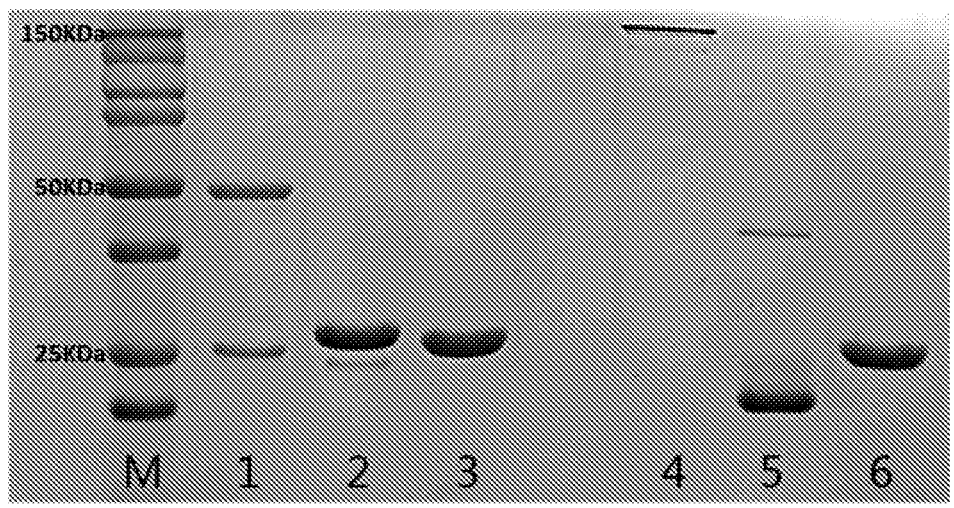
FIG. 10 shows SDS-PAGE results for scFv (PD-L1), the parental humanized IgG1 positive control antibody, and the negative control scFv under both reduced and non-reduced conditions.

The constructs were transiently transfected into expiCHO cells. A one-time feed was added 18 hours later and the supernatant was harvested after culturing for 5 consecutive days. The proteins from the supernatant were purified by protein L sepharose column (GE healthcare) and superdex-75 increase column (GE healthcare) for functional analysis. The parental humanized IgG1 positive control antibody and the negative control scFv were similarly transfected and purified. The titers of the scFvs were measured by Fortebio Octet. The concentrations of the final purified scFvs were determined by Nanodrop. The sc-dsFv with the highest yield of 50 mg/L was chosen for isotype labelling, and is referred to as scFv (PD-L1). FIG. 10 shows the SDS-PAGE results of scFv (PD-L1), the parental humanized IgG1 positive control antibody, and the negative control scFv, under both reduced and non-reduced conditions.

Characterization of scFv (PD-L1)

PD-L1 Binding Activity of scFv (PD-L1) as Measured by FACS

Figure 11:
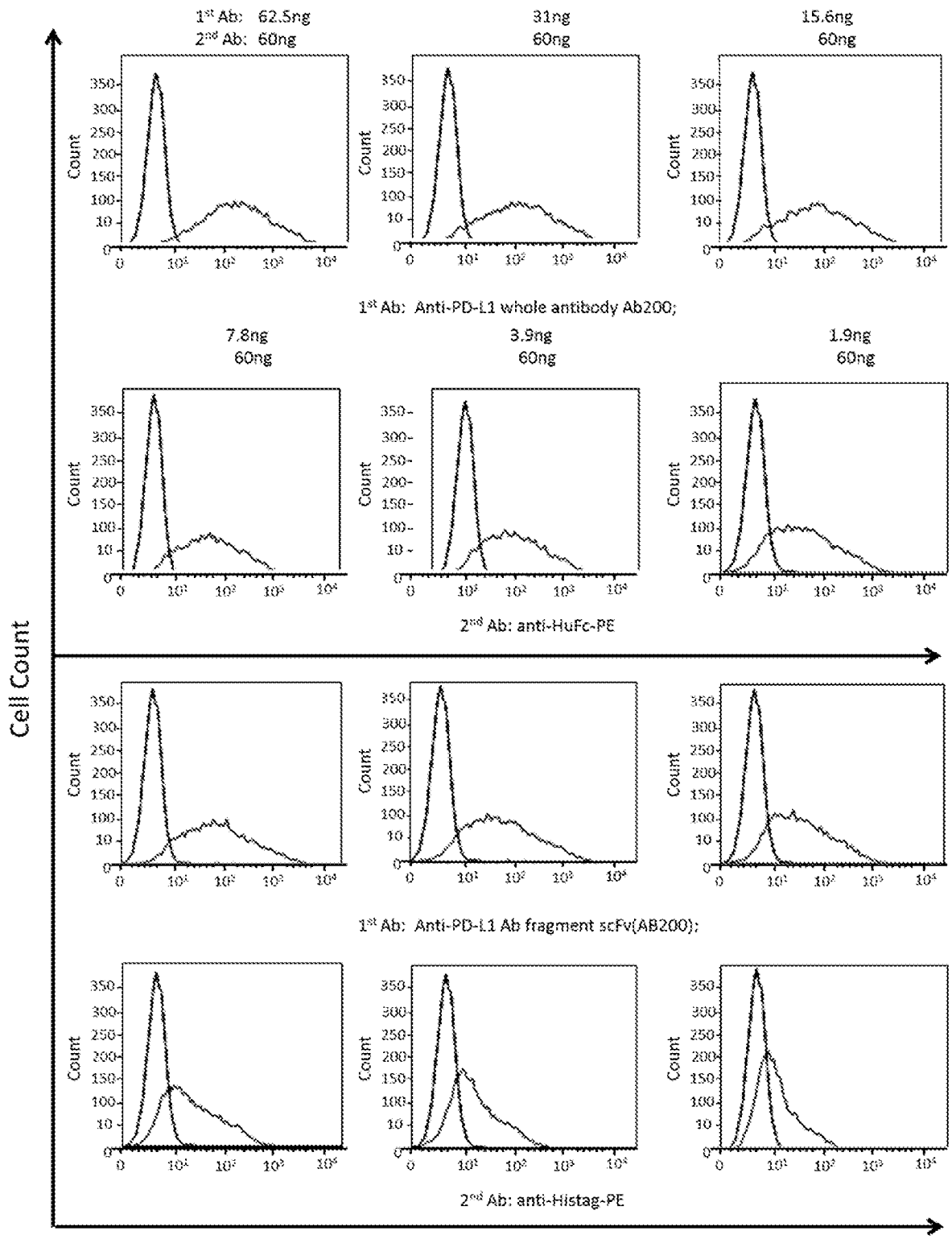
FIG. 11 shows the binding affinity of the parental humanized IgG1 positive control antibody and scFv (PD-L1) to PD-L1 at various concentrations.

CHO/PD-L1 stable cells were harvested and washed twice with FACS buffer (1×PBS with 1% FBS). Cells were then stained with the parental humanized IgG1 positive control antibody (anti-PD-L1 IgG1), or scFv (PD-L1) at various dilutions for 30 minutes on ice. Cells were then washed twice with FACS buffer and further stained with either 60 ng of PE-conjugated anti-human Fc antibody (anti-HuFc-PE, BD), or with 60 ng of PE-conjugated anti-His tag antibody (anti-Histag-PE, eBioscience), for 30 minutes. Cells were washed twice with FACS buffer and suspended in 300 mL of FACS buffer. As shown by the histograms in FIG. 11, the binding activity of both the parental humanized IgG1 positive control antibody (anti-PD-L1 IgG1) and scFv (PD-L1) demonstrated a concentration-dependent pattern.

PD-L1 Binding Affinity of scFv (PD-L1) as Measured by ForteBio Octet RED96

All samples were prepared in PBS buffer (pH=7.4). The biotin-labeled hPD-L1-mouse Fc fusion protein was loaded onto SA sensors at a pre-determined loading threshold. scFv (PD-L1) was applied to the sensors at a concentration gradient of 3.125 nM-50 nM. Background subtraction was used to correct for sensor drifting. The data was fit to a 1:1 binding model using ForteBio's data analysis software in order to obtain the association ($K_{on}$) and dissociation ($K_{off}$) rates. The $K_D$ values were calculated based on $K_{off}/K_{on}$. As shown in Table 9, the binding affinity of scFv (PD-L1) was similar to that of the parental humanized IgG1 positive control antibody.

TABLE 9

Binding affinity analysis of scFv (PD-L1) and the parental
humanized IgG1 positive control antibody

| Sample | $K_D$ (M) | $K_{off}$ (1/s) | $K_{on}$ (1/Ms) | $R^2$ |
|---|---|---|---|---|
| Anti-Human PD-L1 IgG1 | 6.92E−09 | 2.25E−04 | 3.26E+04 | 0.9993 |
| scFv (PD-L1) | 7.11E−09 | 7.01E−04 | 9.85E+04 | 0.995 |

Figure 12:
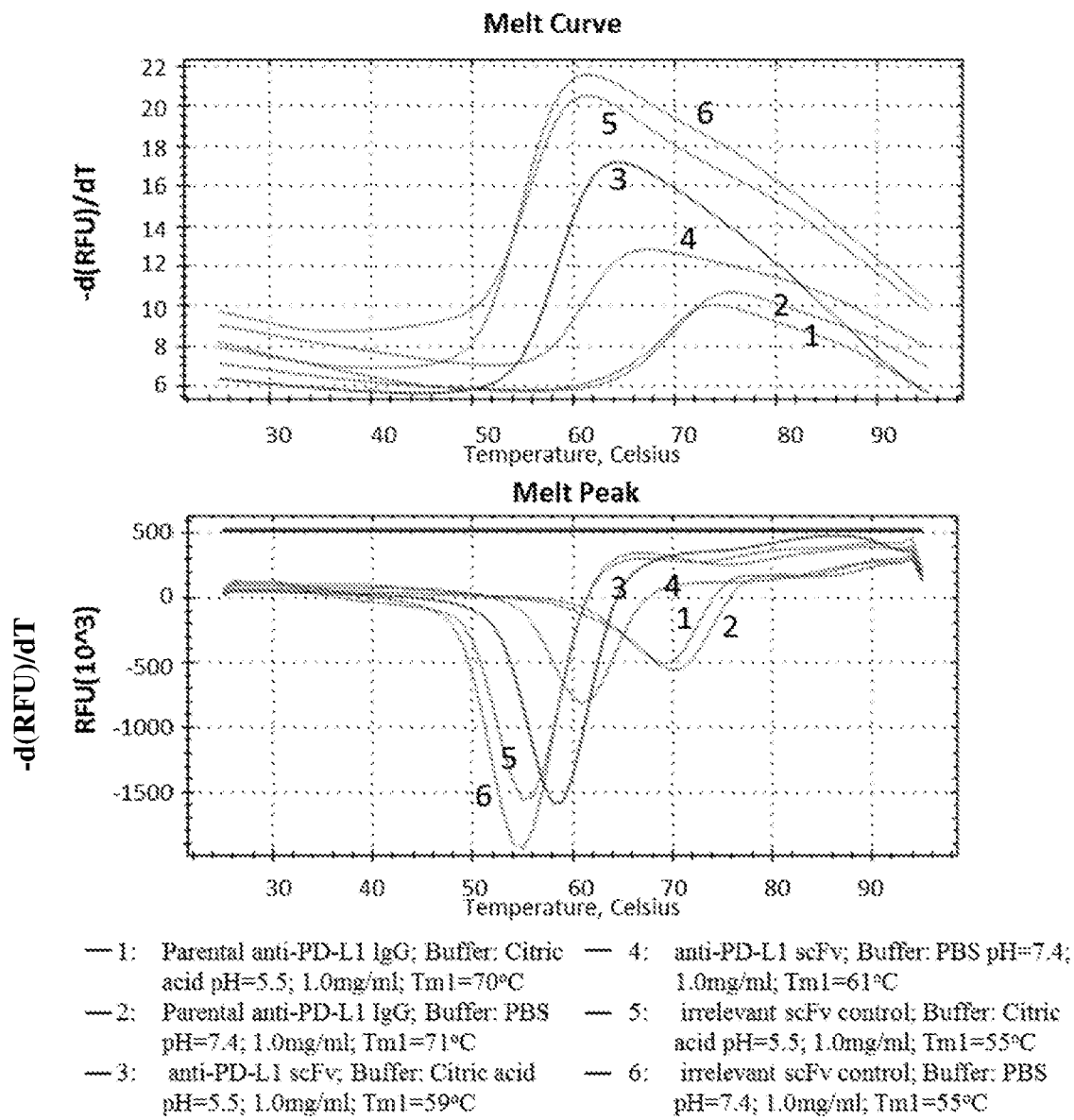
FIG. 12 shows the temperatures of hydrophobic exposure of scFv (PD-L1), the parental humanized IgG1 positive control antibody, and the negative control scFv, as measured by Differential Scanning Fluorimetry (DSF).
Figure 13A:
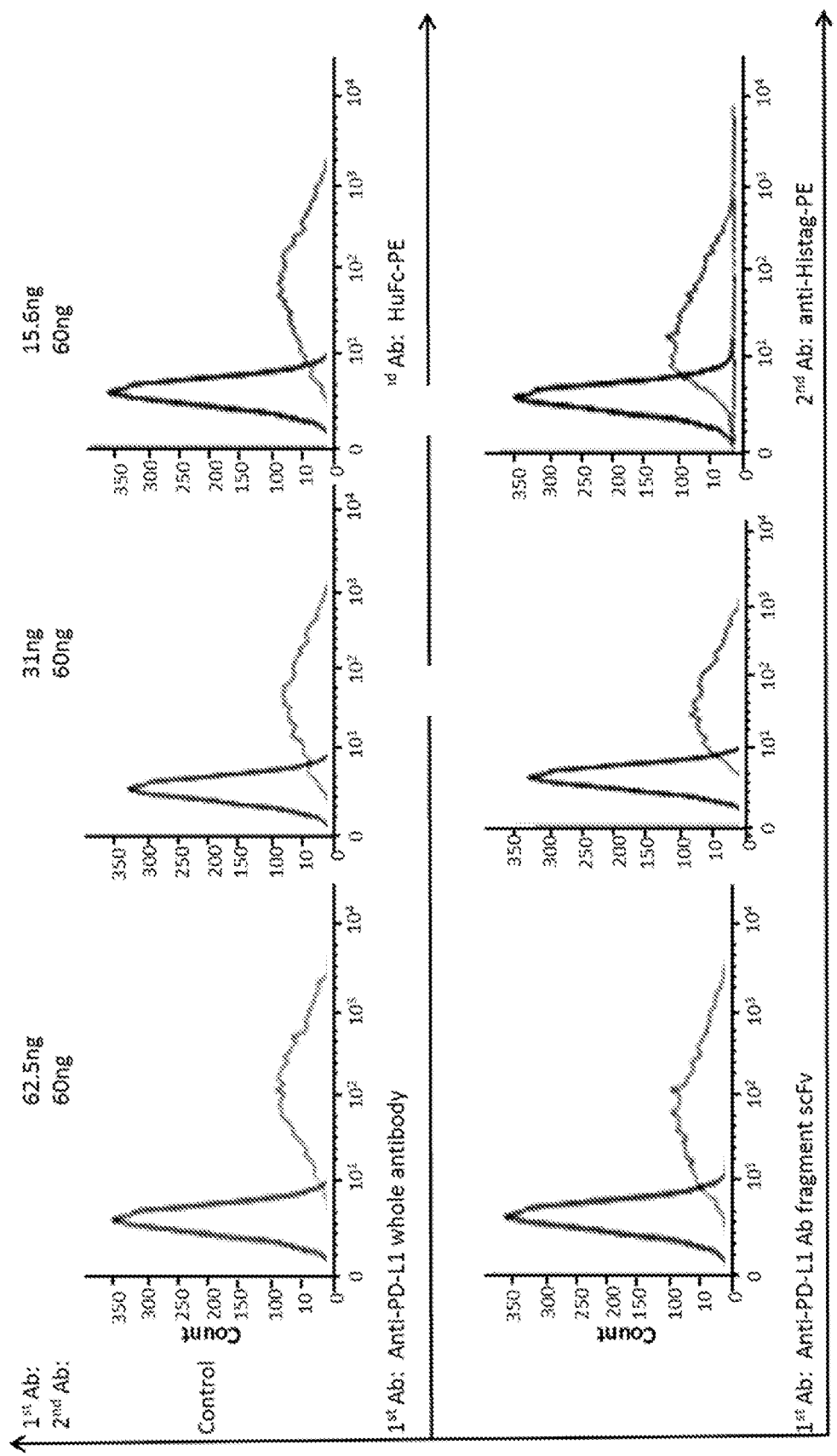
FIGS. 13A-13D show the binding affinities of full-length anti-PD-L1 antibody and scFv (PD-L1) to PD-L1 under a high temperature (40° C.) and high pH (pH=7.4) condition (FIGS. 13A and 13B) as compared to a low temperature (4° C.) and acidic pH (pH=5.5) condition (FIGS. 13C and 13D).
Figure 13B:
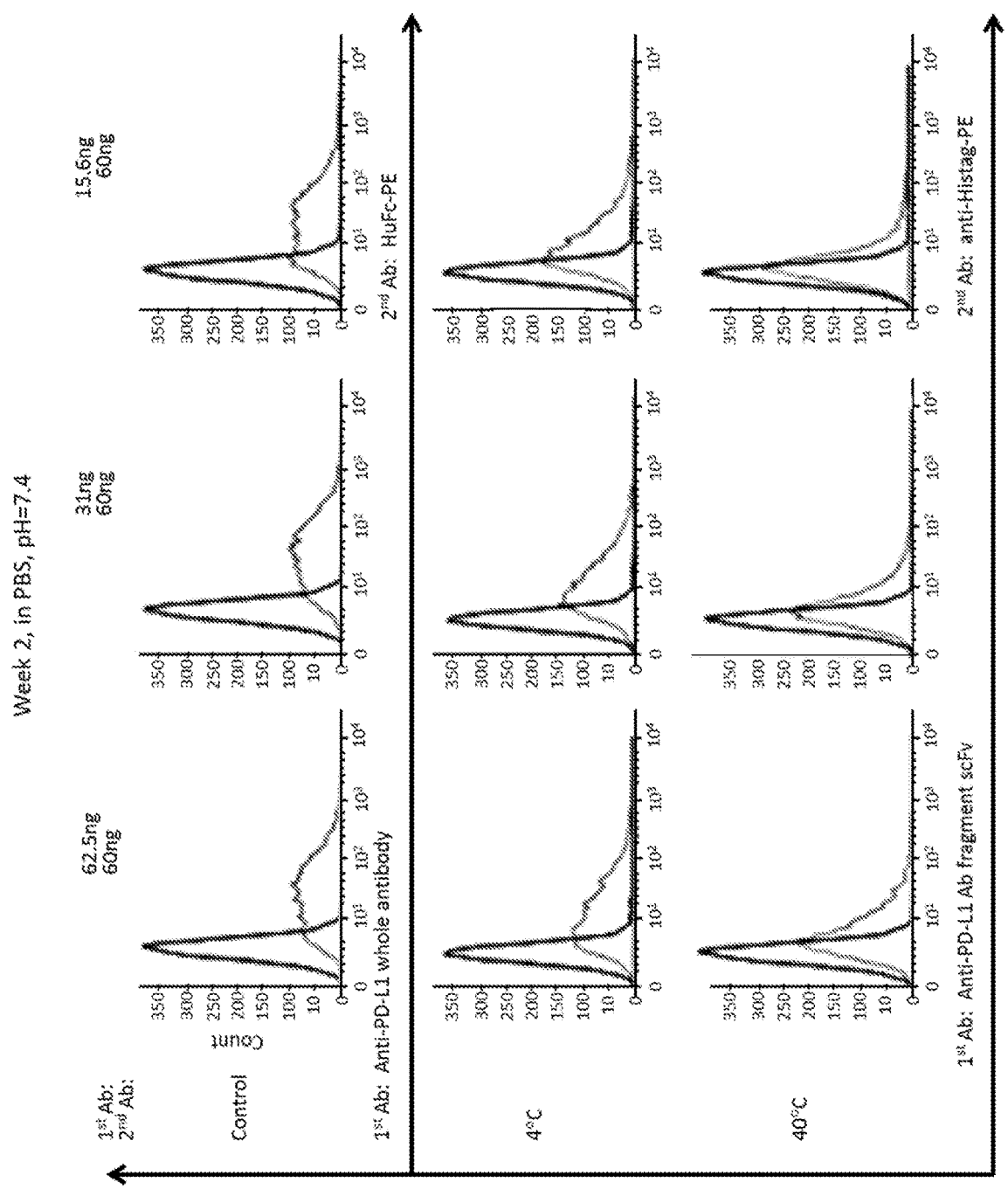
Figure 13C:
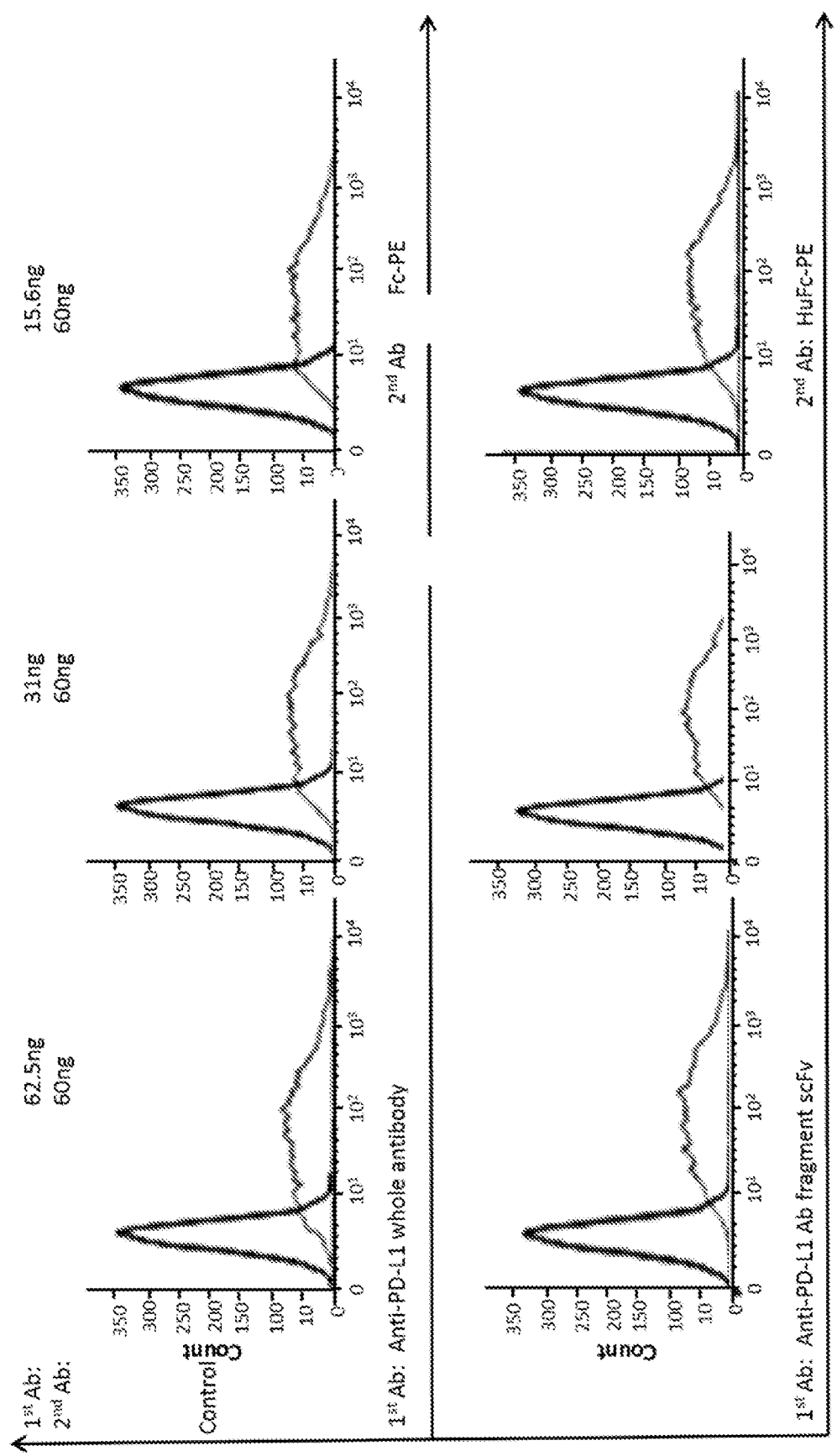
Figure 13D:
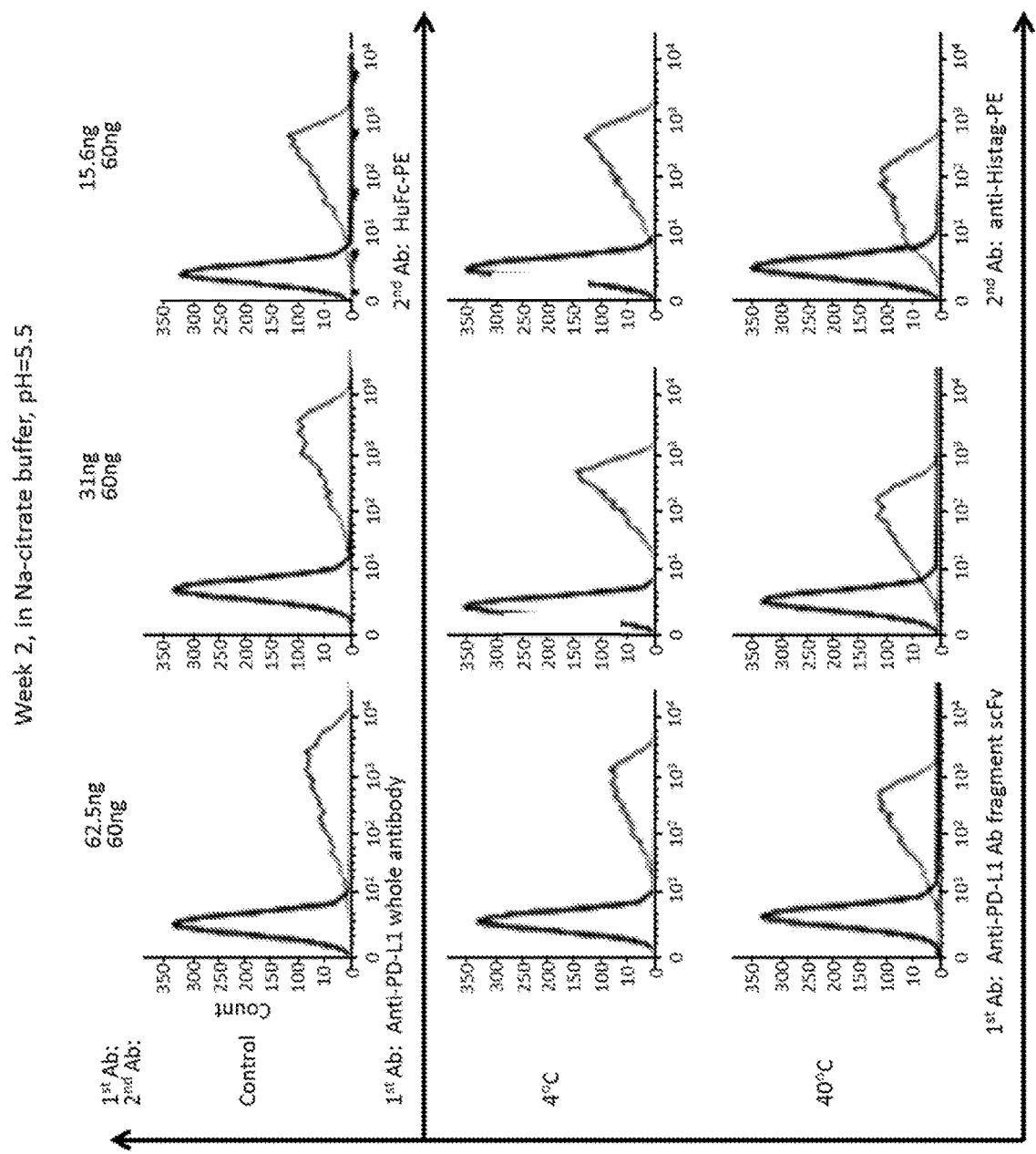

Temperature of Hydrophobic Exposure of scFv (PD-L1) as Measured by Differential Scanning Fluorimetry (DSF)

scFv (PD-L1), the parental humanized IgG1 positive control antibody, and the negative control scFv (irr-control scFv) were expressed and purified as described above. Two buffer conditions (1×PBS at pH 7.4 and Na-Citrate buffer at pH5.5) were used and were achieved via buffer exchange of a concentrated protein stock using Hitrap G25 columns (GE Healthcare). Following buffer change, the protein concentration of the eluate was determined on a Nanodrop (Thermofisher). The final concentrations of scFv (PD-L1) and irr-control scFv were 1 mg/ml, and the concentration of the parental humanized IgG1 positive control antibody was 0.5 mg/ml. Immediately before use, the SYPRO Orange stock solution (5000×) was diluted with the corresponding buffer to a concentration of 25×. The diluted dye was then added to the protein samples to achieve a final working concentration of 5×SYPRO Orange. The CFX96 Real-Time PCR system (Bio-Rad Laboratories) was used to measure SYPRO Orange signals. The excitation/emission filter settings were determined according to the "FRET" channel compatible with the SYPRO Orange fluorescence signal. The samples were exposed to a temperature gradient from 25° C. to 95° C. at a heating rate of 1° C./min with 0.5° C. increments. The −d(RFU)/dT curves representing the change in SYPRO Orange signals over the temperature gradient are shown in FIG. 12. The first trough of the −d(RFU)/dT curve was defined as the temperature of hydrophobic exposure (Tm1 or Th), and was calculated by the CFX MANAGER™ software using the mathematical second derivative method. As shown in FIG. 12, scFv (PD-L1) exhibited a Tm1 of 61° C., the parental humanized IgG1 positive control antibody exhibited a Tm1 of 62° C., while the negative control scFv exhibited a Tm1 of 54° C. scFv (PD-L1) exhibited similar thermo-stability as the parental antibody in both the PBS buffer and the Na-Citrate buffer.

Stability of scFv (PD-L1) at Low Temperature and Acidic pH Conditions

A 40° C. accelerated stability test was performed on scFv (PD-L1) and the parental humanized IgG1 positive control antibody. Briefly, the scFv (PD-L1) and control antibodies were placed in either a 4° C. or a 40° C. stability test chamber (Memmert ICH110L) at a concentration of 1 mg/mL. Every two weeks, samples were removed from the chambers and their binding affinity to PD-L1 was measured using FACS. As shown in FIGS. 13A-13D, the binding affinity of scFv (PD-L1) dramatically reduced over time under the high temperature (40° C.) and high pH (pH 7.4) condition. scFv (PD-L1) exhibited relatively stable characteristics at the low temperature (4° C.) and acidic pH (pH 5.5) condition.

Example 5: Radio-Labeling of Anti-hPD-L1 scFv and Characterization of Radio-Labeled Anti-hPD-L1 scFv Preparation of $^{68}$Ga-NOTA-Anti-PD-L1 Antibody Moieties The experiments described below used an anti-hPD-L1 scFv as an example to prepare an imaging agent for detection of human PD-L1. Imaging agents having other anti-hPD-L1 antibody moieties were prepared using similar experimental procedure by replacing the anti-hPD-L1 scFv below with another anti-hPD-L1 antibody moiety (e.g., scFv, scFv-Fc, or full-length antibody).

Coupling of Anti-hPD-L1 scFv and NOTA scFv antibodies were formulated at a concentration of 2.318 mg/mL (buffered in 20 mM citric acid/sodium citrate/sodium chloride, +0.8% (m/v), pH 5.5). 400 µL of 0.05M NaHCO$_3$—Na$_2$CO$_3$ (pH 8.7) was added to the scFv antibody solution, followed by centrifugation at 16000 rpm for 20 minutes. The supernatant was removed to achieve a final volume of 100 µL. The above steps were repeated one more time and the final 100 µL solution was transferred to a 1.5 mL centrifuge tube. 2.64 µL of p-SCN-Bn-NOTA was added to the centrifuge tube at a final concentration of 927 µM, followed by incubation for one hour at 37° C.

The NAP-5 column was pre-balanced with PBS before the scFv/NOTA solution was added to the column. The column was then washed with 0.4 mL of PBS and eluted with 0.5 mL of PBS. The eluate was aliquoted into 0.05 mL portions and stored at −20° C.

Labeling NOTA-Anti-PD-L1 scFv with $^{68}$Ga $^{68}$Ga was washed with 0.05N HCl to a final concentration of 21 mCi/mL. 46.5 µL of 1.25M sodium acetate was then added to arrive at a final pH of 4. 50 µL of NOTA-anti-PD-L1 scFv (0.05 mg/ml) was added to 350 uL $^{68}$Ga, followed by incubation for 10 min at 25° C. The labeling rate of $^{68}$Ga-NOTA-anti-PD-L1 scFv was determined using the thin layer chromatography paper. When 0.1M citrate was used as the expansion agent the labeling rate was determined to be 17%. When PBS was used as the expansion agent, the labeling rate was determined to be 100%.

Purification of $^{68}$Ga-NOTA-Anti-PD-L1 ScFv

Purification of $^{68}$Ga-NOTA-PD-L1 scFv was performed by first balancing the NAP-5 column with PBS, followed by adding 400 µL of $^{68}$Ga-NOTA-anti-PD-L1 scFv. The column was then washed with 400 µL of PBS, followed by elution with another 400 µL of PBS.

Quality Control of $^{68}$Ga-NOTA-Anti-PD-L1 scFv

Figure 14:
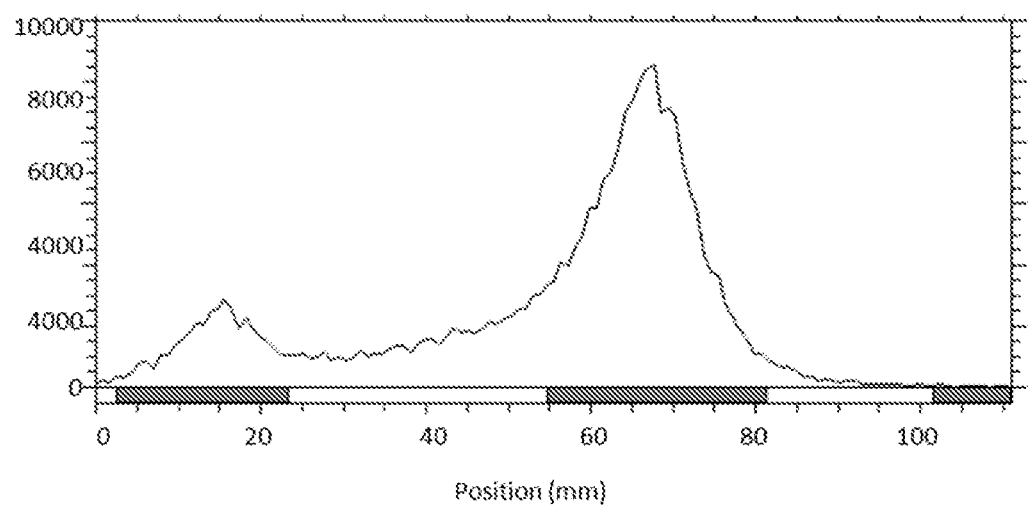
FIG. 14 shows the yield of $^{68}$Ga-NOTA-scFv as measured using instant thin layer chromatography on Silica Gel.
Figure 15:
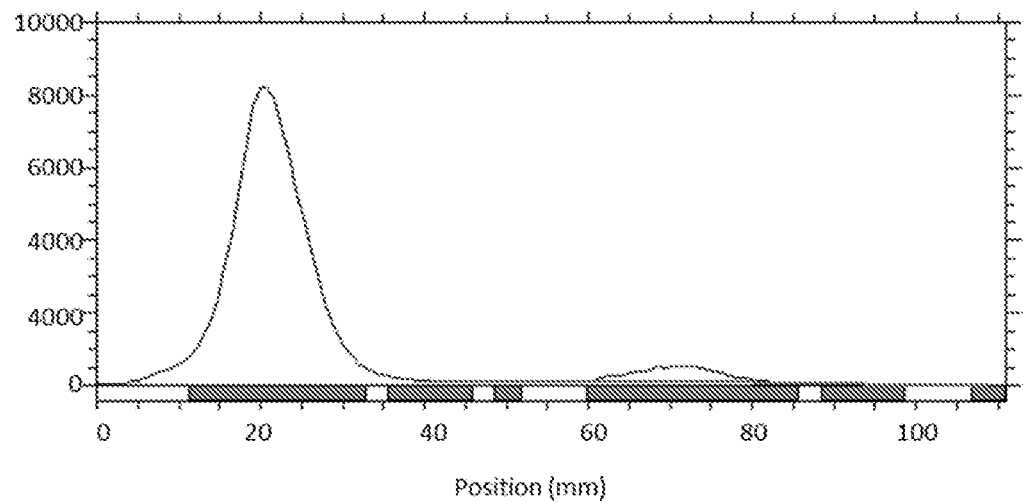
FIG. 15 shows the purity of $^{68}$Ga-NOTA-scFv as measured using instant thin layer chromatography on Silica Gel.

The radiochemical purity of the purified $^{68}$Ga-NOTA-anti-PD-L1 scFv was measured using instant thin layer chromatography-Silica-Gel (ITLC-SG) with 0.1M sodium citrate as the developing agent, with the origin point being the labeled product, and the front edge of the developing agent being dissociated $^{68}$Ga. As shown in FIGS. 14 and 15, the yield of $^{68}$Ga-NOTA-anti-PD-L1 scFv was 17%, and the purity was 93.5%.

Figure 16:
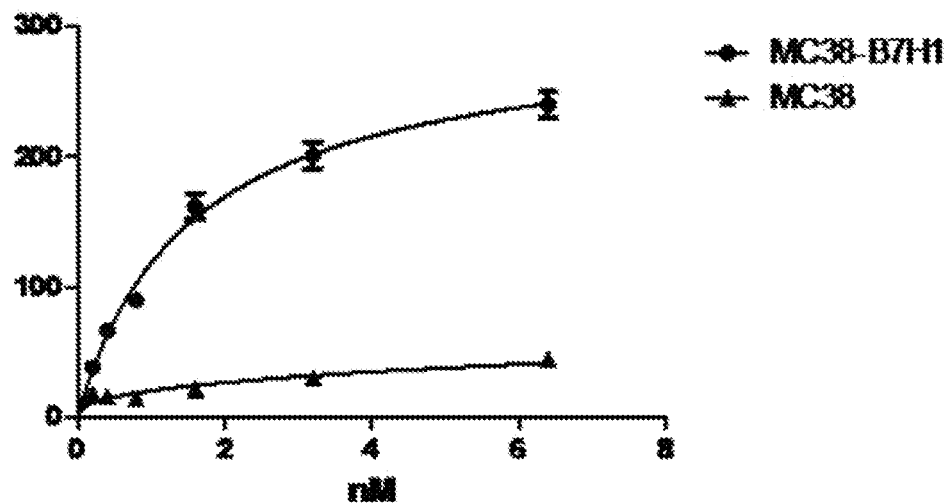
FIG. 16 shows the binding affinity of $^{68}$Ga-NOTA-scFv to MC38-PD-L1 cells as compared to MC38 cells.

$^{68}$Ga-NOTA-Anti-PD-L1 scFv Specific Binding to Human PD-L1 In Vitro $^{68}$Ga-NOTA-anti-PD-L1 scFv cell binding assay. MC38 and MC38-PD-L1 cells were each plated in 12 wells of a 24-well plate at a density of 2.5×10$^5$ cells/well. Cells were cultured for overnight at 37° C. On the next day, $^{68}$Ga-NOTA-anti-PD-L1 scFv was added to the wells at final concentrations of 0.20, 0.40, 0.80, 1.60, 3.20 and 6.40 nM (each concentration had two duplicates), and the cells were incubated at 37° C. for 1 hour. After three washes with ice-cold PBS, the cells were lysed with 0.1M NaOH, and radioactivity was measured using a gamma counting instrument. The K$_D$ value of $^{68}$Ga-NOTA-anti-PD-L1 scFv was calculated using the GraphPad Prism software. As shown in FIG. 16, $^{68}$Ga-NOTA-anti-PD-L1 scFv exhibited much higher binding affinity for MC38-PD-L1 (also referred to as "MC38-B7H1") cells as compared to MC38 cells with the K$_D$ value for MC38-PD-L1 binding being 1.53±0.44 nM.

$^{68}$Ga-NOTA-anti-PD-L1 scFv Competitive Binding Assay. MC38 cells were plated in 8 wells and MC38-PD-L1 cells were plated in 16 wells of a 24-well plate, at a density of 2.5×10$^5$ cells/well. On the next day, anti-PD-L1 IgG1 was added at final concentrations of 20, 40, 80, and 160 nM. Anti-PD-L1 IgG1 and $^{68}$Ga-NOTA-anti-PD-L1 scFv were added in duplicates at final concentrations of 0.20, 0.40, 0.80, 1.60, 3.20 and 6.40 nM. The cells were incubated at 37° C. for 1 hour. After three washes with ice cold PBS, the cells were lysed with 0.1M NaOH and radioactivity was measured using a gamma counting instrument.

Figure 17:
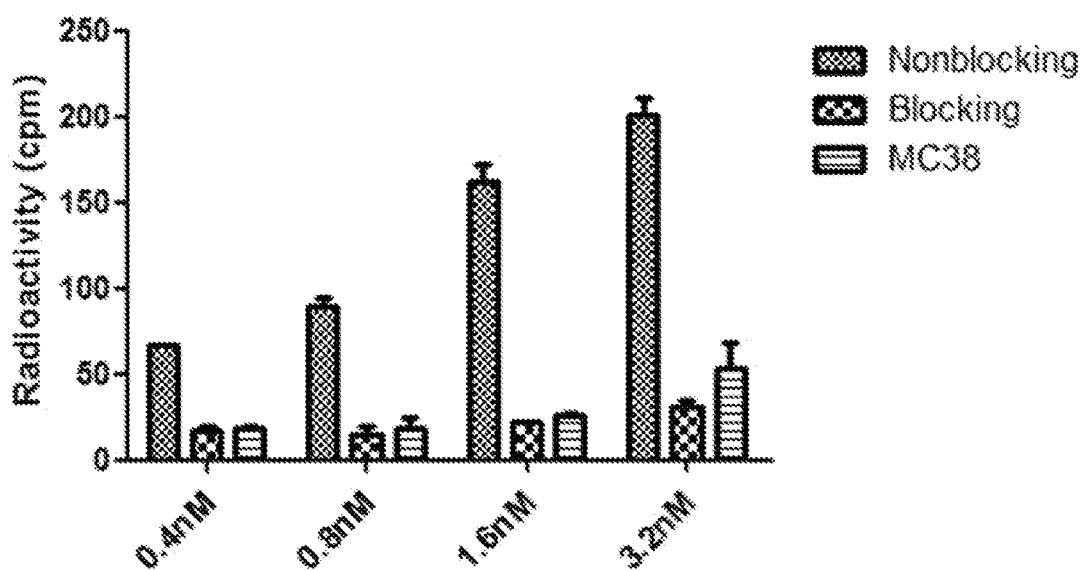
FIG. 17 shows the blocking effect of anti-PD-L1 IgG1 on the binding of $^{68}$Ga-NOTA-anti-PD-L1 scFv to MC38-PD-L1 cells at various concentrations.

As shown in FIG. 17, anti-PD-L1 IgG1 blocked the binding of $^{68}$Ga-NOTA-anti-PD-L1 scFv to MC38-PD-L1 cells. This result demonstrated that binding of $^{68}$Ga-NOTA-anti-PD-L1 scFv to human PD-L1 was specific.

In Vivo Live Imaging of $^{68}$Ga-NOTA-Anti-PD-L1 scFv

In Vivo Live Imaging Assay

MC38 cells and MC38-PD-L1 cells were cultured and counted after trypsin digestion. 1×10$^6$ MC38-PD-L1 cells were injected into the right axilla of five 6-8 week old female mice, and 1×10$^6$ MC38 cells were injected into the left axilla of the same mice. Another five 6-8 week old female mice were injected only with 1×10$^6$ MC38-PD-L1 cells into the right axilla. The tumors reached a diameter of about 0.5 cm after 6 days, at which point the animals received 200 uCi $^{68}$Ga-NOTA-anti-PD-L1 scFv via tail vein injection. Live imaging was carried out 0.5 hour, 1 hour and 2 hours post injection with an exposure time of 5 minutes.

Figure 18:
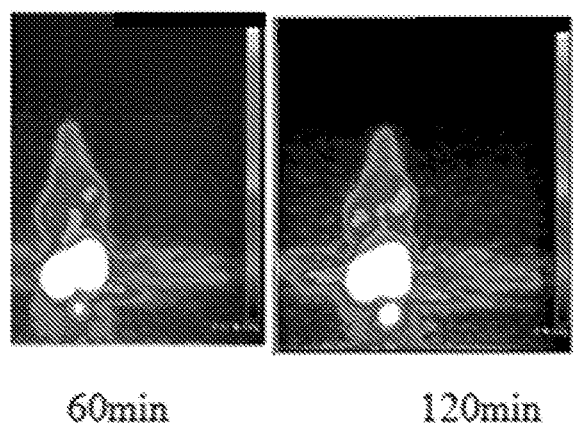
FIG. 18 shows in vivo imaging of tumors induced by injections of MC38-PD-L1 and MC38 cells using $^{68}$Ga-NOTA-anti-PD-L1 scFv.

The maximum exposure images taken at 1 hour and 2 hours post injection are shown in FIG. 18. Tumors in the right axilla (injected with MC38-PD-L1 cells) showed stronger expression as compared to tumors in the left axilla (injected with MC38 cells). Tumors in the left axilla were more visible at 2 hours after injection, as compared to 1 hour after injection. Low uptake and exposure was observed in liver and heart tissues, while high uptake was observed in kidney.

Figure 19:
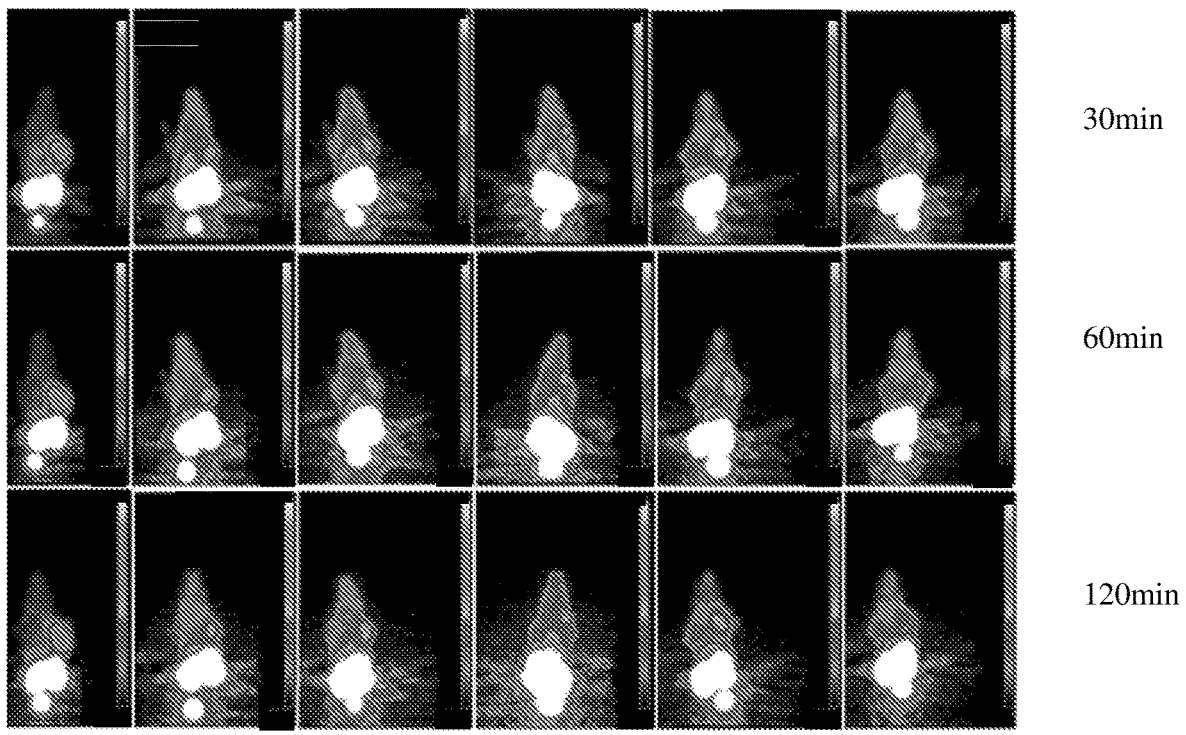
FIG. 19 shows in vivo imaging of tumors induced by injections of MC38-PD-L1 and MC38 cells using $^{68}$Ga-NOTA-anti-PD-L1 scFv.

FIG. 19 shows in vivo imaging results of animals #1-#6 at 0.5 hours, 1 hour and 2 hours after injection of $^{68}$Ga-NOTA-anti-PD-L1 scFv. Animals #1-#4 received MC38-PD-L1 cells in the right axilla only, while animals #5 and #6 also received MC38 cells in the left axilla in addition to MC38-PD-L1 cells in the right axilla. The results showed that radioactive signal was detectable by 0.5 hours, and the uptake by the kidney did not decrease significantly over time. Animal #1 showed clear imaging and may be related to the specific growth status of the tumor.

Binding Competition In Vivo Imaging Assay

Figure 20:
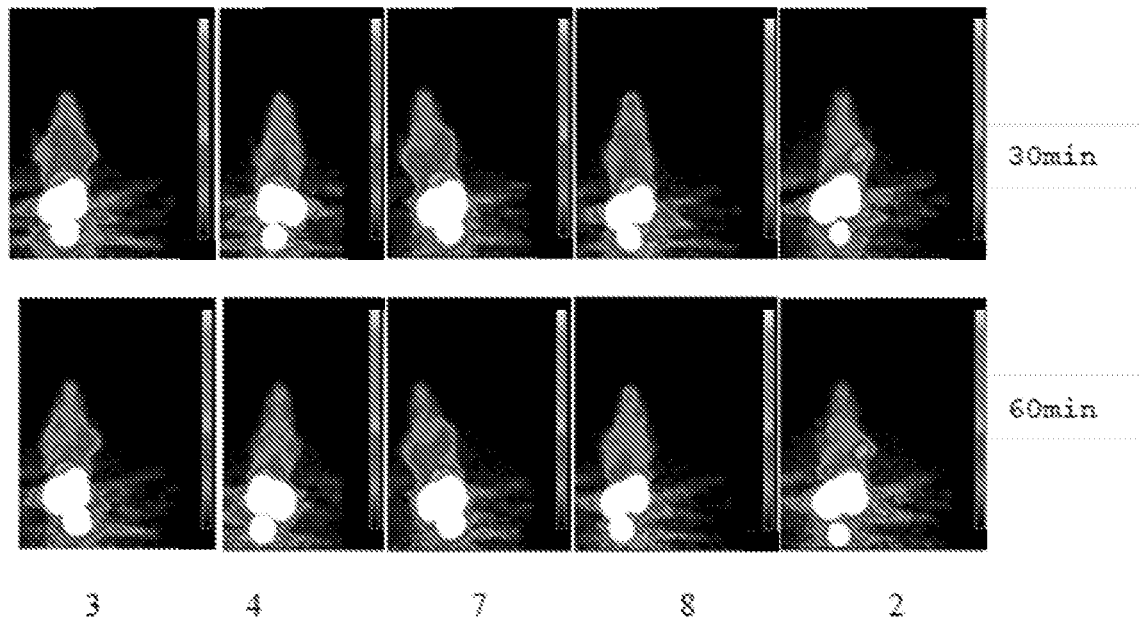
FIG. 20 shows in vivo imaging results demonstrating the competition between unlabeled anti-PD-L1 IgG1 and $^{68}$Ga-NOTA-anti-PD-L1 scFv for binding to PD-L1.

MC38 cells and MC38-PD-L1 cells were cultured and counted after trypsin digestion. 1×10$^6$ MC38-PD-L1 cells were injected into the right axilla of five 6-8 week old female mice (#2, #3, #4, #7 and #8). 1×10$^6$ MC38 cells were also injected into the left axilla of mice #7 and #8. The tumors reached a diameter of about 0.5 cm after 6 days. Animals #3, #4, #7 and #8 received both the unlabeled antibody anti-PD-L1 IgG1 and 140 uCi of $^{68}$Ga-NOTA-anti-PD-L1 scFv via tail vein injections. The unlabeled antibody anti-PD-L1 IgG1 was injected at a concentration that was 50 times of the concentration of $^{68}$Ga-NOTA-anti-PD-L1 scFv. Animal #2 received 140 uCi of $^{68}$Ga-NOTA-anti-PD-L1 scFv only as control. Live imaging was carried out 0.5 hour, 1 hour and 2 hours post injection with an exposure time of 5 minutes. As shown in FIG. 20, animal #2 showed binding of $^{68}$Ga-NOTA-anti-PD-L1 scFv to B7H1 (PD-L1), whereas unlabeled ab-220 antibody when injected at a concentration 50 times that of $^{68}$Ga-NOTA-anti-PD-L1 scFv blocked the binding of $^{68}$Ga-NOTA-anti-PD-L1 scFv to B7H1 (PD-L1).

Comparison Between 68Ga-NOTA-Anti-PD-L1 scFv and 68Ga-NOTA-Anti-PD-L1 scFv-Fc

MC38 cells and MC38-PD-L1 cells were cultured and counted after trypsin digestion. 1×10$^6$ MC38-PD-L1 cells were injected into the right axilla of five 6-8 week old female mice, and 1×10$^6$ MC38 cells were injected into the left axilla of the same mice. The tumors reached a diameter of about 0.5 cm after 6 days, at which point the animals received 200 μCi $^{68}$Ga-NOTA-anti-PD-L1 scFv, unlabeled anti-PD-L1 scFv with 200 μCi $^{68}$Ga-NOTA-anti-PD-L1 scFv, or 200 μCi $^{68}$Ga-NOTA-anti-PD-L1 scFv-Fc via tail vein injection. Live imaging was carried out 0.5 hour, 1 hour and 2 hours post injection with an exposure time of 5 minutes. For mice injected with $^{68}$Ga-NOTA-anti-PD-L1 scFv-Fc, images were taken with normal camera sensitivity setting, and a reduced camera sensitivity setting (¼ of normal conditions).

Figure 21:
FIG. 21 shows in vivo imaging results of tumors in mice 30 minutes after injection of $^{68}$Ga-NOTA-anti-PD-L1 scFv, unlabeled anti-PD-L1 scFv and $^{68}$Ga-NOTA-anti-PD-L1 scFv, $^{68}$Ga-NOTA-anti-PD-L1 scFv-Fc(wt) at normal camera sensitivity setting, and $^{68}$Ga-NOTA-anti-PD-L1 scFv-Fc (wt) at % of normal camera sensitivity setting.

FIG. 21 shows a side-by-side comparison of imaging results at 30 minutes after injection of the imaging agents. From left to right of the figure shows imaging results of a mouse injected with $^{68}$Ga-NOTA-anti-PD-L1 scFv, a mouse injected with unlabeled anti-PD-L1 scFv and $^{68}$Ga-NOTA-anti-PD-L1 scFv, a mouse injected with $^{68}$Ga-NOTA-anti-PD-L1 scFv-Fc(wt) at normal camera sensitivity setting, and the same mouse injected with $^{68}$Ga-NOTA-anti-PD-L1 scFv-Fc(wt) at a reduced camera sensitivity setting.

Figure 22:
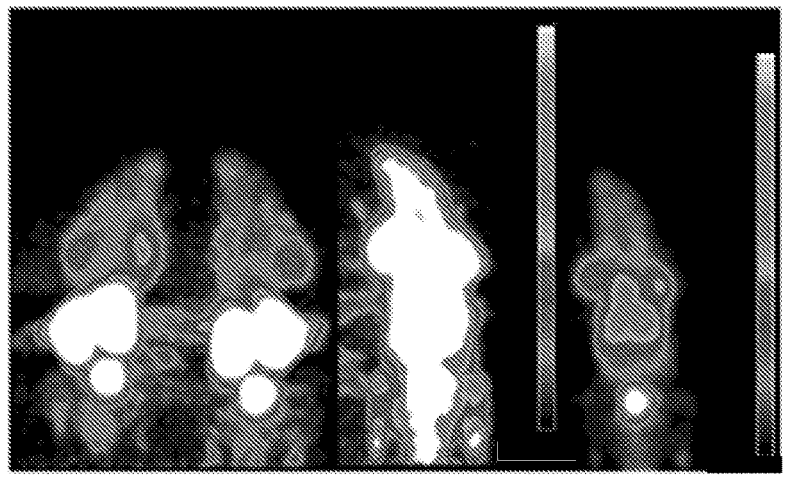
FIG. 22 shows in vivo imaging results of tumors in mice 1 hour (top panel) or 2 hours (bottom panel) after injection of $^{68}$Ga-NOTA-anti-PD-L1 scFv, unlabeled anti-PD-L1 scFv and $^{68}$Ga-NOTA-anti-PD-L1 scFv, $^{68}$Ga-NOTA-anti-PD-L1 scFv-Fc(wt) at normal camera sensitivity setting, and $^{68}$Ga-NOTA-anti-PD-L1 scFv-Fc(wt) at % of normal camera sensitivity setting.
Figure 22:
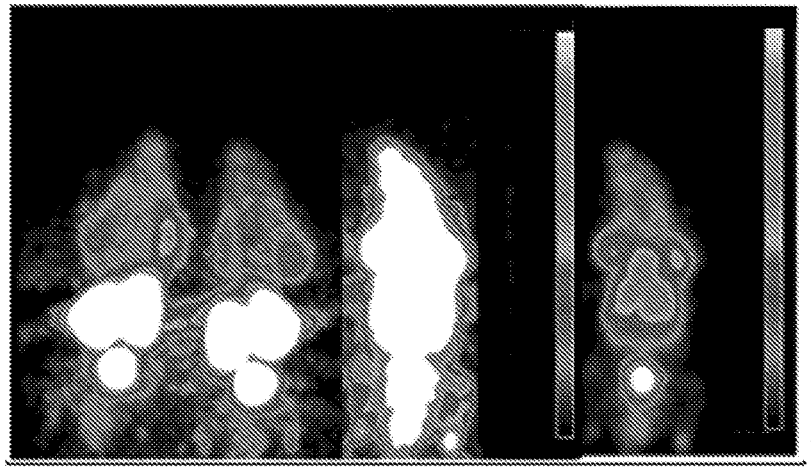

FIG. 22 shows a side-by-side comparison of imaging results at 60 minutes (top panel) and 120 minutes (bottom panel) after injection of the imaging agents. From left to right of the figure shows imaging results of a mouse injected with $^{68}$Ga-NOTA-anti-PD-L1 scFv, a mouse injected with unlabeled anti-PD-L1 scFv and $^{68}$Ga-NOTA-anti-PD-L1 scFv, a mouse injected with $^{68}$Ga-NOTA-anti-PD-L1 scFv-Fc(wt) at normal camera sensitivity setting, and the same mouse injected with $^{68}$Ga-NOTA-anti-PD-L1 scFv-Fc(wt) at a reduced camera sensitivity setting.

What is claimed is:

1. A method of determining the distribution of an immune checkpoint ligand in an individual, comprising:
  (a) administering to the individual an imaging agent comprising an antibody moiety labeled with a radionuclide, wherein the antibody moiety specifically binds the immune checkpoint ligand, wherein the antibody moiety comprises a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46;
  (b) imaging the imaging agent in the individual with a non-invasive imaging technique; and
  (c) determining the expression level of the immune checkpoint ligand in a tissue of interest in the individual based on signals emitted by the imaging agent from the tissue.

2. A method of diagnosing an individual having a disease or condition, wherein the disease or condition is associated with an abnormal immune response, comprising:
  (a) determining the distribution of an immune checkpoint ligand in the individual by administering to the individual an imaging agent comprising an antibody moiety labeled with a radionuclide, wherein the antibody moiety specifically binds the immune checkpoint ligand, wherein the antibody moiety comprises a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46; and imaging the imaging agent in the individual with a non-invasive imaging technique; and (b) diagnosing the individual as positive for the immune checkpoint ligand if signal of the imaging agent is detected at a tissue of interest, or diagnosing the individual as negative for the immune checkpoint ligand if signal of the imaging agent is not detected at a tissue of interest.

3. A method of treating an individual having a disease or condition, wherein the disease or condition is associated with an abnormal immune response, comprising:

(a) diagnosing the individual using the method of claim 2; and (b) administering to the individual an effective amount of a therapeutic agent targeting the immune checkpoint ligand, if the individual is diagnosed as positive for the immune checkpoint ligand.

4. An isolated anti-PD-L1 antibody agent comprising an antibody moiety comprising a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46.

5. The isolated anti-PD-L1 antibody agent of claim 4, wherein the antibody moiety comprises: a VH comprising an amino acid sequence having at least 80% sequence identity to an amino acid sequence of any one of SEQ ID NOs: 1, 5, 9, 11, and 13; and a VL comprising an amino acid sequence having at least 80% sequence identity to an amino acid sequence of any one of SEQ ID NOs: 3, 7, 15, 17 and 19.

6. The isolated anti-PD-L1 antibody agent of claim 4, wherein the antibody moiety comprises an scFv.

7. The isolated anti-PD-L1 antibody agent of claim 6, wherein the scFv comprises a first cysteine residue at position 44 of VH and a second cysteine residue at position 100 of VL, or a first cysteine residue at position 105 of VH and a second cysteine residue at position 43 of VL, wherein the first cysteine residue and the second cysteine residue form a disulfide bond, and wherein the amino acid positions are based on the Kabat numbering system.

8. The isolated anti-PD-L1 antibody agent of claim 6, wherein the scFv comprises an amino acid sequence having at least 80% sequence identity to the amino acid sequence of any one of SEQ ID NOs: 25, 27, 29, 31, 33, 35, 37 and 39.

9. The isolated anti-PD-L1 antibody agent of claim 6, wherein the antibody moiety is an scFv.

10. The isolated anti-PD-L1 antibody agent of claim 6, wherein the antibody moiety is an scFv fused to an Fc fragment.

11. The isolated anti-PD-L1 antibody agent of claim 10, wherein the Fc fragment is a human IgG1 Fc fragment.

12. The isolated anti-PD-L1 antibody agent of claim 11, wherein the Fc fragment has H310A and H435Q mutations, wherein the amino acid positions are based on the Kabat numbering system.

13. An anti-PD-L1 antibody agent comprising an antibody moiety that specifically binds PD-L1 competitively with the antibody moiety in the anti-PD-L1 antibody agent of claim 4.

14. An imaging agent comprising an antibody moiety labeled with a radionuclide, wherein the antibody moiety specifically binds an immune checkpoint ligand, and wherein the antibody moiety comprises a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46.

15. An imaging agent comprising the isolated anti-PD-L1 antibody agent of claim 4, wherein the antibody moiety is labeled with a radionuclide.

16. A method of preparing an imaging agent targeting PD-L1, comprising:

(a) conjugating a chelating compound to the antibody moiety in the isolated anti-PD-L1 antibody agent of claim 4 provide an anti-PD-L1 conjugate;

(b) contacting a radionuclide with the anti-PD-L1 antibody conjugate, thereby providing the imaging agent.

17. An isolated nucleic acid encoding the isolated anti-PD-L1 antibody agent of claim 4.

18. A kit comprising:

(a) an antibody moiety specifically binding an immune checkpoint ligand, wherein the antibody moiety comprises a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46; and (b) a chelating compound.

19. A kit comprising:

(a) an imaging agent comprising an antibody moiety labeled with a radionuclide, wherein the antibody moiety specifically binds an immune checkpoint ligand, wherein the antibody moiety comprises a heavy chain variable region (VH) comprising a heavy chain complementarity determining region (HC-CDR)1 comprising an amino acid sequence of SEQ ID NO: 41, a HC-CDR2 comprising an amino acid sequence of SEQ ID NO: 42, and a HC-CDR3 comprising an amino acid sequence of SEQ ID NO: 43; and a light chain variable region (VL) comprising a light chain complementarity determining region (LC-CDR)1 comprising an amino acid sequence of SEQ ID NO: 44, a LC-CDR2 comprising an amino acid sequence of SEQ ID NO: 45, and a LC-CDR3 comprising an amino acid sequence of SEQ ID NO: 46; and (b) an antibody moiety not labeled with a radionuclide.

20. The isolated anti-PD-L1 antibody agent of claim 4, wherein the antibody moiety comprises:

(a) a VH comprising an amino acid sequence of SEQ ID NO: 1; and a VL comprising an amino acid sequence of SEQ ID NO: 3;

(b) a VH comprising an amino acid sequence of SEQ ID NO: 1; and a VL comprising an amino acid sequence of SEQ ID NO: 7;
(c) a VH comprising an amino acid sequence of SEQ ID NO: 1; and a VL comprising an amino acid sequence of SEQ ID NO: 15;
(d) a VH comprising an amino acid sequence of SEQ ID NO: 1; and a VL comprising an amino acid sequence of SEQ ID NO: 17;
(e) a VH comprising an amino acid sequence of SEQ ID NO: 1; and a VL comprising an amino acid sequence of SEQ ID NO: 19;
(f) a VH comprising an amino acid sequence of SEQ ID NO: 5; and a VL comprising an amino acid sequence of SEQ ID NO: 3;
(g) a VH comprising an amino acid sequence of SEQ ID NO: 5; and a VL comprising an amino acid sequence of SEQ ID NO: 7;
(h) a VH comprising an amino acid sequence of SEQ ID NO: 5; and a VL comprising an amino acid sequence of SEQ ID NO: 15;
(i) a VH comprising an amino acid sequence of SEQ ID NO: 5; and a VL comprising an amino acid sequence of SEQ ID NO: 17;
(j) a VH comprising an amino acid sequence of SEQ ID NO: 5; and a VL comprising an amino acid sequence of SEQ ID NO: 19;
(k) a VH comprising an amino acid sequence of SEQ ID NO: 9; and a VL comprising an amino acid sequence of SEQ ID NO: 3;
(l) a VH comprising an amino acid sequence of SEQ ID NO: 9; and a VL comprising an amino acid sequence of SEQ ID NO: 7;
(m) a VH comprising an amino acid sequence of SEQ ID NO: 9; and a VL comprising an amino acid sequence of SEQ ID NO: 15;
(n) a VH comprising an amino acid sequence of SEQ ID NO: 9; and a VL comprising an amino acid sequence of SEQ ID NO: 17;
(o) a VH comprising an amino acid sequence of SEQ ID NO: 9; and a VL comprising an amino acid sequence of SEQ ID NO: 19;
(p) a VH comprising an amino acid sequence of SEQ ID NO: 11; and a VL comprising an amino acid sequence of SEQ ID NO: 3;
(q) a VH comprising an amino acid sequence of SEQ ID NO: 11; and a VL comprising an amino acid sequence of SEQ ID NO: 7;
(r) a VH comprising an amino acid sequence of SEQ ID NO: 11; and a VL comprising an amino acid sequence of SEQ ID NO: 15;
(s) a VH comprising an amino acid sequence of SEQ ID NO: 11; and a VL comprising an amino acid sequence of SEQ ID NO: 17;
(t) a VH comprising an amino acid sequence of SEQ ID NO: 11; and a VL comprising an amino acid sequence of SEQ ID NO: 19;
(u) a VH comprising an amino acid sequence of SEQ ID NO: 13; and a VL comprising an amino acid sequence of SEQ ID NO: 3;
(v) a VH comprising an amino acid sequence of SEQ ID NO: 13; and a VL comprising an amino acid sequence of SEQ ID NO: 7;
(w) a VH comprising an amino acid sequence of SEQ ID NO: 13; and a VL comprising an amino acid sequence of SEQ ID NO: 15;
(x) a VH comprising an amino acid sequence of SEQ ID NO: 13; and a VL comprising an amino acid sequence of SEQ ID NO: 17; or
(y) a VH comprising an amino acid sequence of SEQ ID NO: 13; and a VL comprising an amino acid sequence of SEQ ID NO: 19.

21. The isolated anti-PD-L1 antibody agent of claim 4, wherein the antibody moiety comprises: a VH comprising an amino acid sequence of SEQ ID NO: 9; and a VL comprising an amino acid sequence of SEQ ID NO: 17.

\* \* \* \* \*